United States Patent [19]

Kim et al.

[11] Patent Number: 4,552,696
[45] Date of Patent: Nov. 12, 1985

[54] CARBAPENEM ANTIBIOTICS

[75] Inventors: Choung U. Kim, Manlius; Peter F. Misco, Jr., Syracuse, both of N.Y.

[73] Assignee: Bristol-Myers Company, New York, N.Y.

[21] Appl. No.: 471,379

[22] Filed: Mar. 8, 1983

Related U.S. Application Data

[63] Continuation-in-part of Ser. No. 366,910, Apr. 9, 1982, abandoned.

[51] Int. Cl.$^4$ .................... C07D 487/04; A61K 31/40
[52] U.S. Cl. ............................................. 260/245.2 T
[58] Field of Search ................. 260/245.2 T, 245.2 R; 424/274; 514/210

[56] References Cited

U.S. PATENT DOCUMENTS 4,235,920  11/1980  Christensen et al. ............... 424/274

Primary Examiner—Nicholas S. Rizzo
Attorney, Agent, or Firm—David M. Morse

[57] ABSTRACT

Disclosed are novel carbapenem derivatives characterized by a 2-substituent of the formula

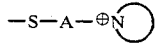

in which A represents cyclopentylene, cyclohexylene or $C_2$–$C_6$ alkylene optionally substituted by one or more $C_1$–$C_4$ alkyl groups and

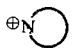

represents a quaternized nitrogen-containing aromatic heterocycle. Such derivatives are useful as potent antibacterial agents. Also disclosed are processes for the preparation of such derivatives and novel intermediates utilized in these processes.

5 Claims, No Drawings

CARBAPENEM ANTIBIOTICS

CROSS-REFERENCE TO RELATED APPLICATIONS

This application is a continuation-in-part of our co-pending application Ser. No. 366,910 filed Apr. 9, 1982 now abandoned.

BACKGROUND OF THE INVENTION

1. Field of the Invention

The present invention is directed to new carbapenem derivatives in which the 2-substituent has the formula

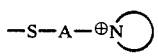

in which A represents a straight or branched chain alkylene group or a cyclopentylene or cyclohexylene group and

represents a quaternized nitrogen-containing aromatic heterocycle.

2. Description of the Prior Art

A number of β-lactam derivatives containing the carbapenem nucleus

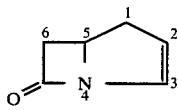

have been disclosed in the literature. These carbapenem derivatives have been reported to possess utility as antibacterial agents and/or β-lactamase inhibitors.

The initial carbapenem compounds were natural products such as thienamycin of the formula

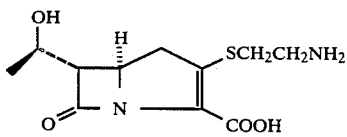

obtained by fermentation of *Streptomyces cattleya* (U.S. Pat. No. 3,950,357). Thienamycin is an exceptionally potent broad-spectrum antibiotic which possesses notable activity against various Pseudomonas species, organisms which have been notoriously resistant to β-lactam antibiotics.

Other natural products containing the carbapenem nucleus include olivanic acid derivatives such as antibiotic MM 13902 of the formula

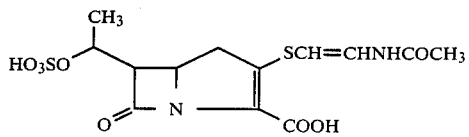

disclosed in U.S. Pat. No. 4,113,856, antibiotic MM 17880 of the formula

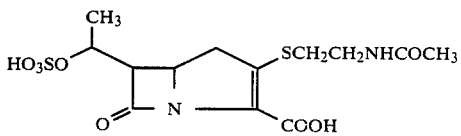

disclosed in U.S. Pat. No. 4,162,304, antibiotic MM 4550A of the formula

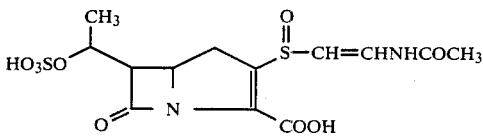

disclosed in U.S. Pat. No. 4,172,129 and antibiotic 890A9 of the formula

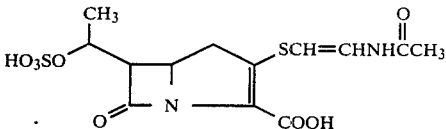

disclosed in U.S. Pat. No. 4,264,735. In addition to the natural products, the compound desacetyl 890A10 of the formula

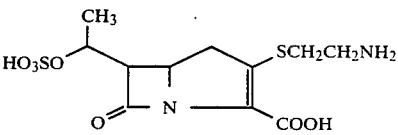

is disclosed in U.S. Pat. No. 4,264,734 as being prepared by an enzymatic deacylation of the corresponding N-acetyl compound. Various derivatives of the naturally-occurring olivanic acids have also been synthesized, e.g. the compounds of the formula

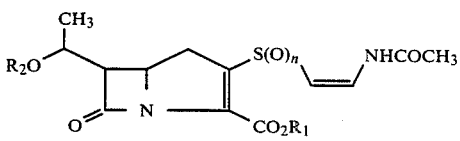

wherein $CO_2R_1$ is a free, salted or esterified carboxyl group, n is 0 or 1 and $R_2$ is H, an acyl group or a group of the formula $R_3O_3S$ wherein $R_3$ is a salting ion or a methyl or ethyl group, disclosed in European Patent Application No. 8885.

U.S. Pat. No. 4,235,922 (see also European Patent Application 2058) discloses the carbapenem derivative of the formula while U.K. Patent Application No. 1,598,062 reports isolation of the compound from a Streptomyces fermentation broth.

Carbapenems which are unsubstituted in the 6-position have also been synthesized. Thus, U.S. Pat. No. 4,210,661 discloses compounds of the formula wherein $R_2$ is phenyl or substituted phenyl, U.S. Pat. No. 4,267,177 discloses compounds of the formula wherein $R_1$ is an optionally substituted pyridyl group, U.S. Pat. No. 4,255,441 discloses compounds of the formula wherein $R_2$ and $R_3$ are H or alkyl and $R_4$ is NH—$CO_nR_6$ in which $R_6$ is alkyl, phenyl or substituted phenyl and n is 1 or 2, and U.S. Pat. No. 4,282,236 discloses compounds of the formula wherein $R_1$ is H or alkyl and $R_2$ is CN or $CO_2R_3$ in which $R_3$ is H, alkyl, aryl or aralkyl.

Carbapenems of the general formula wherein $R^1$ is H or acyl and $R^8$ is H or substituted or unsubstituted: alkyl, alkenyl, alkynyl, cycloalkyl, cycloalkylalkyl, alkylcycloalkyl, aryl, aralkyl, aralkenyl, aralkynyl, heteroaryl, heteroaralkyl, heterocyclyl or heterocyclylalkyl, are disclosed in U.S. Pat. No. 4,218,463. There is no disclosure of any heteroaralkyl $R^8$ substituents of the type in which A is alkylene and is a quaternized nitrogen-containing aromatic heterocycle.

The natural product thienamycin has the absolute configuration 5R, 6S, 8R. This isomer, as well as the remaining seven thienamycin isomers, may be obtained via total synthesis as disclosed in U.S. Pat. No. 4,234,596. Total synthesis procedures for thienamycin are also disclosed, for example, in U.S. Pat. Nos. 4,287,123, 4,269,772, 4,282,148, 4,273,709, 4,290,947 and European Patent Application No. 7973. A key intermediate in the disclosed synthetic methods is wherein pNB represents p-nitrobenzyl.

Because of the exceptional biological activity of thienamycin, a large number of derivatives have been prepared and disclosed in the literature. Among these are (1) N-formimidoyl thienamycin of the formula disclosed in Europen Patent Application No. 6639; (2) N-heterocyclic derivatives of thienamycin having the formula and -continued

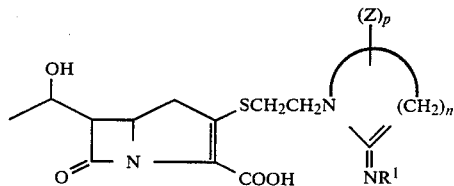

wherein: the bifunctional ring may contain additional unsaturation in the ring; and wherein n is an integer selected from 1-6; p is 0, 1 or 2; $R^1$ is H, alkyl or aryl; and Z is imino, oxo, H, amino or alkyl, disclosed in U.S. Pat. No. 4,189,493; (3) substituted N-methylene derivatives of thienamycin having the formula

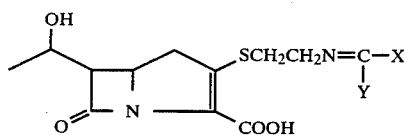

wherein X and Y are H, R, OR, SR or $NR^1R^2$ in which R is substituted or unsubstituted: alkyl, alkenyl, alkynyl, cycloalkyl, cycloalkylalkyl, aryl, aralkyl, heteroaryl, heteroaralkyl, heterocyclyl or heterocyclylalkyl, and $R^1$ and $R^2$ are H or R, disclosed in U.S. Pat. No. 4,194,047; (4) compounds of the formula

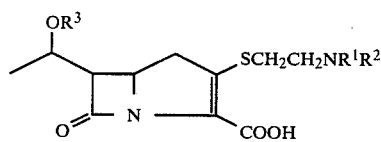

wherein $R^3$ is aryl, alkyl, acyl or aralkyl and $R^1$ and $R^2$ are independently selected from H and acyl (including acyl of the type

in which $R^{11}$ may inter alia be alkyl substituted by a quaternary ammonium group, e.g.

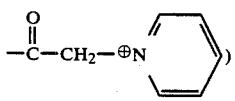

disclosed in U.S. Pat. No. 4,226,870; (5) compounds of the formula

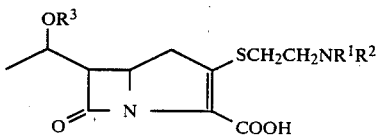

wherein $R^3$ is H, acyl or an univalent optionally substituted hydrocarbon radical; $R^1$ is optionally substituted alkyl, alkenyl, alkynyl, cycloalkyl, cycloalkenyl, cycloalkenylalkyl, cycloalkylalkyl, aryl, aralkyl, heteroaryl or heteroaralkyl and $R^2$ is acyl (including acyl of the type

in which R is alkyl substituted by a quaternary ammonium group, e.g.

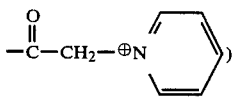

disclosed in U.K. Patent No. 1,604,276 (see also U.S. Pat. No. 4,235,917); (6) Compounds of the formula

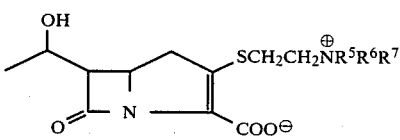

wherein $R^5$, $R^6$ and $R^7$ are independently selected from H and substituted or unsubstituted: alkyl, alkenyl, alkynyl, cycloalkyl, cycloalkenyl, cycloalkenylalkyl, cycloalkylalkyl, aryl, aralkyl, heteroaryl or heteroaralkyl, are disclosed in U.S. Pat. No. 4,235,920; (7) compounds of the formula

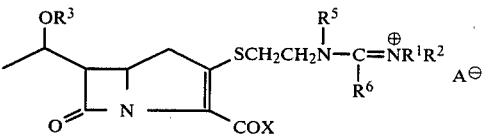

wherein each of $R^1$ and $R^2$, independently of the other, is a radical of the type defined for R, a hydrogen atom, or a nitro, hydroxyl, $C_{1-6}$ alkoxyl, amino, $C_{1-6}$ alkylamino, di($C_{1-6}$ alkyl)amino or tri($C_{1-6}$ alkylamino) radical, an extra anion being present in the latter case; or $R^1$ and $R^2$ are joined together to form, together with the nitrogen atom to which they are attached, a substituted or unsubstituted monocyclic or bicyclic heteroaryl or heterocyclyl residue containing 4–10 ring atoms, one or more of which may be an additional hetero atom selected from oxygen, sulphur and nitrogen; R is a cyano group or a substituted or unsubstituted carbamoyl, carboxyl, ($C_{1-10}$ alkoxy)carbonyl, $C_{1-10}$ alkyl, $C_{2-10}$ alkenyl, $C_{2-10}$ alkynyl, $C_{3-10}$ cycloalkyl, $C_{4-12}$ cycloalkylalkyl, $C_{5-12}$ cycloalkylalkenyl, $C_{3-10}$ cycloalkenyl, $C_{5-12}$ cycloalkenylalkyl, $C_{4-12}$ cycloalkenylalkyl, $C_{6-10}$ aryl, $C_{7-16}$ aralkyl, $C_{8-16}$ aralkenyl, $C_{8-16}$ aralkynyl or monocyclic or bicyclic heteroaryl, heteroaralkyl, heterocyclyl or heterocyclylalkyl comprising 4 to 10 ring atoms one or more of which is a hetero atom selected from oxygen, sulphur and nitrogen and in which the alkyl residue of the heteroaralkyl or heterocyclylalkyl radical contains from 1 to 6 carbon atoms; the substituent or substituents on R, $R^1$, $R^2$ or on the ring formed by joining $R^1$ and $R^2$ are chlorine; bromine; iodine; fluorine; azido; $C_{1-4}$ alkyl; mercapto; sulpho; phosphono; cyanothio (-SCN); nitro; cyano; amino; hydrazin; amino or hydrazino having up to three $C_{1-6}$ alkyl substituents; hydroxy; $C_{1-6}$ alkoxy; $C_{1-6}$ alkylthio; carboxyl; oxo;

(C$_{1-6}$ alkoxy)carbonyl; C$_{2-10}$ acyloxy; carbamoyl; (C$_{1-14}$ alkyl) carbamoyl or di(C$_{1-4}$ alkyl) carbamoyl; R$_3$ is a hydrogen atom, an acyl radical or a radical of the type defined for R$^4$; R$^4$ is C$_{1-10}$ alkyl; substituted carbonylmethyl; C$_{1-6}$ alkoxy)-(C$_{1-6}$ alkyl), (C$_{3-6}$ cycloalkoxy)-(C$_{1-6}$ alkyl); C$_{2-12}$ alkanoyloxyalkyl; partially or completely halogenated C$_{1-6}$ alkyl in which the halogen(s) is/are chlorine, bromine or fluorine; aminoalkyl; C$_{2-10}$ alkenyl; C$_{2-10}$ alkynyl; acyl; C$_{3-14}$ alkoxycarbonylalkyl; C$_{4-21}$ dialkylaminoacetoxyalkyl; C$_{2-13}$ alkanoylaminoalkyl; ar-(C$_{1-3}$ alkyl) in which the aryl residue contains from 6 to 10 carbon atoms; monocyclic or bicyclic heteroaralkyl or heterocyclylalkyl containing 4 to 10 ring atoms, 1 to 3 carbon atoms in the alkyl residue, and 1-4 hetero atoms selected from oxygen, sulphur and/or nitrogen; nuclear-substituted aralkyl or heteroaralkyl in which the substituent is chlorine, fluorine, bromine, iodine or C$_{1-6}$ alkyl; aryl or nuclear-substituted aryl containing 6 to 10 ring carbon atoms and in which any nuclear substituent is hydroxy, C$_{1-6}$ alkyl, chlorine, fluorine or bromine; aralkoxyalkyl; C$_{2-12}$ alkylthioalkyl; C$_{4-12}$ cycloalkylthioalkyl; (C$_{2-10}$ acylthio)-(C$_{1-6}$ alkyl); or phenylalkenyl in which alkenyl has 2-6 carbon atoms; R$^5$ is substituted or unsubstituted C$_{1-10}$ alkyl; C$_{2-10}$ alkenyl or alkynyl; ring substituted and unsubstituted cycloalkyl, cycloalkenyl, cycloalkenylalkyl, and cycloalkyl-alkyl having 3-6 ring carbon atoms and up to 6 carbon atoms in any chain; C$_{6-10}$ aryl; aralkyl having 6-10 ring carbon atoms and 1-6 carbon atoms in the alkyl chain; monocyclic or bicyclic heteroaryl or heteroaralkyl containing 4-10 ring atoms, one or more of which is oxygen, nitrogen or sulphur, and 1-6 carbon atoms in the alkyl chain; and the ring or chain substituent(s) is/are chlorine, bromine, iodine, fluorine, azido, cyano, amino, C$_{1-6}$ alkylamino, di(C$_{1-6}$ alkyl)amino or tri(C$_{1-6}$ alkylamino) radical, an extra anion being present in the latter case, hydroxy, C$_{1-6}$ alkoxy, C$_{1-6}$ alkylthioalkyl; carboxyl; oxo, (C$_{1-6}$ alkoxy)carbonyl; C$_{2-10}$ acyloxy; carbamoyl; (C$_{1-4}$ alkyl)carbamoyl; di(C$_{1-4}$ alkyl)carbamoyl; cyanothio (—SCN) or nitro; R$^6$ is hydrogen, hydroxy, mercapto, R, —OR, —SR or NR$^1$R$^2$, where R, R$^1$ and R$^2$ are as defined above;

X is hydroxy, mercapto, amino, acyloxy —OR$^4$, —SR$^4$, —NHR$^4$, $$-\underset{\underset{R^4}{|}}{N}-R^4,$$

—OM, —OQ or, when the compound is in zwitterionic form, —O$^-$, in which case A$^-$ is absent;

A, when the compound is not in zwitterionic form, is a counter ion;

M is a pharmaceutically acceptable cation; and

Q is a blocking group as herein defined, are disclosed in U.K. Patent No. 1,604,275; and (8) compounds of the formula

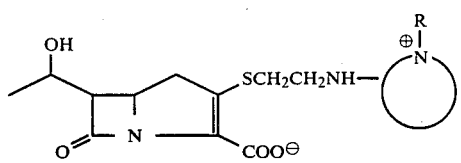

wherein

attached to the amino nitrogen group of thienamycin represents a mono- or polycyclic N-containing heterocyclic group and R is H, substituted or unsubstituted: alkyl, aryl, alkenyl, heterocyclylalkenyl, aralkenyl, heterocyclylalkyl, aralkyl, —NR$_2$, COOR, CONR$_2$, —OR, or CN, are disclosed in European Patent Application 21082. Among the compounds disclosed in U.S. Pat. No. 4,235,920 is

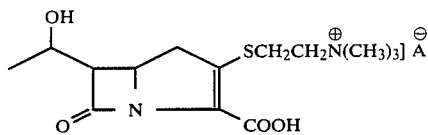

wherein A is a pharmaceutically acceptable anion. The abovementioned quaternary amine derivative is also described in Recent Advances in the Chemistry of β-Lactam Antibiotics, Royal Society of Chemistry, London, 1981, pg 240–254, where its antibacterial activity on average is reported as approximately ½ to ⅔ that of thienamycin.

Carbapenem derivatives having a wide variety of 6-substituents in addition to those mentioned above have also been synthesized. Thus, for example, (1) European Patent Application 40408 discloses compounds of the formula

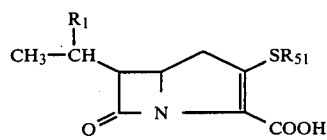

wherein R$_1$ is H, methyl or hydroxyl and R$_{51}$ is a monovalent organic group including inter alia heterocyclicmethyl; (2) European Patent Application 8514 discloses compounds of the formula

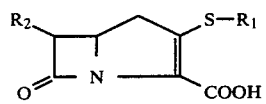

wherein R$_1$ is an optionally substituted pyrimidinyl group and R$_2$ is hydrogen or a group CR$_3$R$_4$R$_5$ wherein R$_3$ is hydrogen or hydroxy, R$_4$ is hydrogen or alkyl and R$_5$ is hydrogen, alkyl, benzyl or phenyl, or R$_5$ and R$_4$ together form a carbocyclic ring; (3) European Patent Application 38869 discloses compounds of the formula

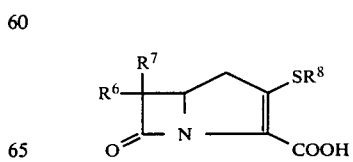

wherein R$^6$, R$^7$, and R$^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl; wherein the substituent or substituents relative to the above-named radicals are selected from the group consisting of:

—X° halo (chloro, bromo, fluoro)
—OH hydroxy
—$OR^1$ alkoxy, aryloxy

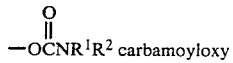
—$OCNR^1R^2$ carbamoyloxy

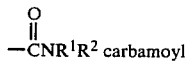
—$CNR^1R^2$ carbamoyl

—$NR^1R^2$ amino

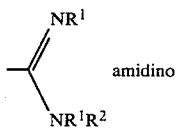
amidino

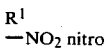
—$NO_2$ nitro

—$\overset{\oplus}{N}(R^1)_3$ tri-substituted amino ($R^1$ group independently chosen)

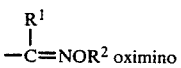
—C=$NOR^2$ oximino

—$SR^1$ alkyl- and arylthio
—$SO_2NR^1R^2$ sulfonamido

—$NHCNR^1R^2$ ureido

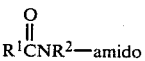
$R^1CNR^2$—amido

—$CO_2H$ carboxy
—$CO_2R^1$ carboxylate

—$CR^1$ acyl

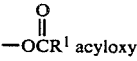
—$OCR^1$ acyloxy

—SH mercapto

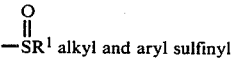
—$SR^1$ alkyl and aryl sulfinyl

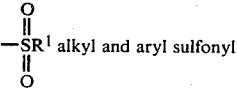
—$SR^1$ alkyl and aryl sulfonyl

—CN cyano
—$N_3$ azido wherein, relative to the above listed substituents on $R^6$, $R^7$, and $R^8$, the groups $R^1$ and $R^2$ are independently selected from: hydrogen, alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl and wherein the hetero atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms. (See also European Patent Application Nos. 1627, 1628, 10317, 17992, 37080, 37081 and 37082); (4) European Patent Application 24832 discloses compounds of the formula

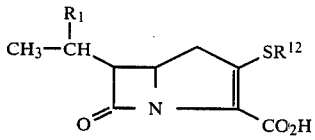

wherein $R^1$ is H or a group selected from OH, $OSO_3H$ or a salt or $C_{1-4}$ alkyl ester thereof, $OR^2$, $SR^3$, $OCOR^2$, $OCO_2R^3$ or $OCONHR^3$, where $R^2$ is a $C_{1-6}$ alkyl group or an optionally substituted benzyl group and $R^3$ is a $C_{1-6}$ alkyl group or an optionally substituted benzyl or phenyl group and $R^{12}$ is $C_{1-6}$ alkyl, $C_{2-6}$ alkenyl, $C_{3-6}$ alkynyl wherein the triple bond is not present on the carbon adjacent to the sulfur atom, aralkyl, $C_{1-6}$ alkanoyl, aralkanoyl, aryloxyalkanoyl or arylcarbonyl, any of such $R^{12}$ groups being optionally substituted, as antibacterial agents.

European Patent Application No. 44,170 discloses carbapenem derivatives of the formula

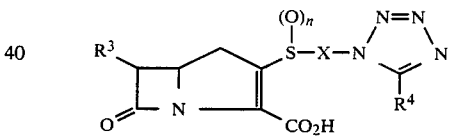

wherein $R^3$ is hydrogen or an organic group bonded via a carbon atom to the carbapenem ring, n is 0 or 1, X is a saturated or unsaturated hydrocarbon radical optionally substituted by bromo or chloro, and $R^4$ is a $C_1$-$C_6$ alkyl, $C_2$-$C_6$ alkenyl, $C_1$-$C_{10}$ aralkyl or aryl group, any of such groups $R^4$ being optionally substituted. There is no disclosure, however, of any compounds wherein the tetrazole ring is bonded to X via a quaternized nitrogen atom, i.e. a positively charged nitrogen which is not attached to a hydrogen atom.

European Patent Application 38,869 mentioned above discloses synthesis of the carbapenem derivatives via intermediates of the general formula

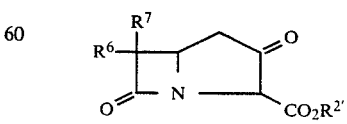

wherein $R^6$ and $R^7$ are as defined above and $R_2'$ is a readily removable carboxyl protecting group. Also disclosed as intermediates are compounds of the formula

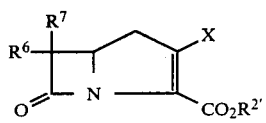

wherein X is described as a leaving group.

While, as indicated above, the prior art has described carbapenem derivatives having a 2-substituent of the general formula

wherein A represents an alkylene group and Het represents a heteroaromatic group, there has been no disclosure of which applicants are aware teaching carbapenems wherein Het is a radical of the formula

in which

represents a quaternized nitrogen-containing aromatic heterocycle bonded to the alkylene or cycloalkylene carbon via the quaternary nitrogen atom. As mentioned above, the carbapenem having

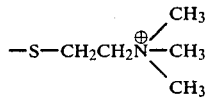

as the 2-substituent has also been reported.

Despite the vast number of carbapenem derivatives disclosed in the literature, there is still a need for new carbapenems since known derivatives may be improved upon in terms of spectrum of activity, potency, stability and/or toxic side effects.

SUMMARY OF THE INVENTION

The present invention provides a novel series of carbapenem derivatives characterized by a 2-substituent of the formula

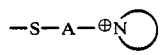

wherein A is straight or branched chain alkylene or is a cyclopentylene or cyclohexylene group and

represents a quaternized nitrogen-containing aromatic heterocycle. More specifically, the present invention provides carbapenem derivatives of the formula

I

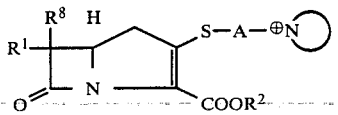

wherein $R^8$ is hydrogen and $R^1$ is selected from the group consisting of hydrogen; substituted and unsubstituted: alkyl, alkenyl and alkynyl, having from 1-10 carbon atoms; cycloalkyl and cycloalkylalkyl, having 3-6 carbon atoms in the cycloalkyl ring and 1-6 carbon atoms in the alkyl moieties; phenyl; aralkyl, aralkenyl and aralkynyl wherein the aryl moiety is phenyl and the aliphatic portion has 1-6 carbon atoms; heteroaryl, heteroaralkyl, heterocyclyl and heterocyclylalkyl wherein the hetero atom or atoms in the above-named heterocyclic moieties are selected from the group consisting of 1-4 oxygen, nitrogen or sulfur atoms and the alkyl moieties associated with said heterocyclic moieties have 1-6 carbon atoms; wherein the substituent or substituents relative to the above-named radicals are selected from the group consisting of $C_1$-$C_6$ alkyl optionally substituted by amino, halo, hydroxy or carboxyl halo
—$OR^3$

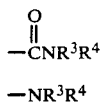

—$NR^3R^4$

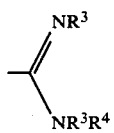

—$SO_2NR^3R^4$

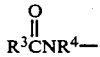

—$CO_2R^3$

=O

—$SR^3$

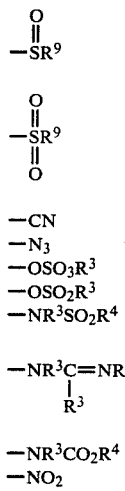

—CN
—N₃
—OSO₃R³
—OSO₂R³
—NR³SO₂R⁴

$$-NR^3C=NR^4$$
$$\quad\quad |$$
$$\quad\quad R^3$$

—NR³CO₂R⁴
—NO₂ wherein, relative to the above-named substituents, the groups R³ and R⁴ are independently selected from hydrogen; alkyl, alkenyl and alkynyl, having from 1–10 carbon atoms; cycloalkyl, cycloalkylalkyl and alkylcycloalkyl, having 3–6 carbon atoms in the cycloalkyl ring and 1–6 carbon atoms in the alkyl moieties; phenyl; aralkyl, aralkenyl and aralkynyl wherein the aryl moiety is phenyl and the aliphatic portion has 1–6 carbon atoms; and heteroaryl, heteroaralkyl, heterocyclyl and heterocyclylalkyl wherein the hetero atom or atoms in the above-named heterocyclic moieties are selected from the group consisting of 1–4 oxygen, nitrogen or sulfur atoms and the alkyl moieties associated with said heterocyclic moieties have 1–6 carbon atoms, or R³ and R⁴ taken together with the nitrogen to which at least one is attached may form a 5- or 6-membered nitrogen-containing heterocyclic ring; R⁹ is as defined for R³ except that it may not be hydrogen; or wherein R¹ and R⁸ taken together represent C₂–C₁₀ alkylidene or C₂–C₁₀ alkylidene substituted by hydroxy; A is cyclopentylene, cyclohexylene or C₂–C₆ alkylene optionally substituted by one or more C₁–C₄ alkyl groups; R² is hydrogen, an anionic charge or a conventional readily removable carboxyl protecting group, providing that when R² is hydrogen or a protecting group, there is also present a counter anion; and

represents a substituted or unsubstituted mono-, bi- or polycyclic aromatic heterocyclic radical containing at least one nitrogen in the ring and attached to A through a ring nitrogen, thereby forming a quaternary ammonium group; and pharmaceutically acceptable salts thereof. The compounds of formula I are potent antibacterial agents or intermediates useful in the preparation of such agents.

Also provided by the invention are novel intermediates of the formula

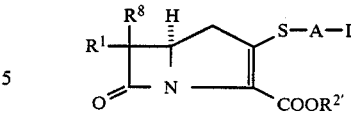

wherein R²' is a conventional readily removable carboxyl protecting group and R¹, R⁸ and A are as defined above.

Also included in the invention are processes for preparing the novel carbapenem derivatives described above and pharmaceutical compositions containing the biologically active carbapenem derivatives in combination with pharmaceutically acceptable carriers or diluents.

DETAILED DESCRIPTION

The novel compounds of general formula I above contain the carbapenem nucleus

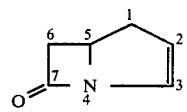

and may thus be named as 1-carba-2-penem-3-carboxylic acid derivatives. Alternatively, the compounds may be considered to have the basic structure

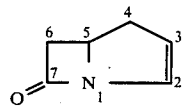

and named as 7-oxo-1-azabicyclo(3.2.0)hept-2-ene-2-carboxylic acid derivatives. While the present invention includes compounds wherein the relative stereochemistry of the 5,6-protons is cis as well as trans, the preferred compounds have the 5R,6S (trans) stereochemistry as in the case of thienamycin.

The compounds of formula I may be unsubstituted in the 6-position or substituted by substituent groups previously disclosed for other carbapenem derivatives. More specifically, R⁸ may be hydrogen and R¹ may be hydrogen or a non-hydrogen substituent disclosed, for example, in European Patent Application No. 38,869 (see definition of R₆). Alternatively, R⁸ and R¹ taken together may be C₂–C₁₀ alkylidene or C₂–C₁₀ alkylidene substituted, for example, by hydroxy.

To elaborate on the definitions for R¹ and R⁸:

(a) The aliphatic "alkyl", "alkenyl" and "alkynyl" groups may be straight or branched chain having 1–10 carbon atoms; preferred are 1–6, most preferably 1–4, carbon groups; when part of another substituent, e.g. as in cycloalkylalkyl, or heteroaralkyl or aralkenyl, the alkyl, alkenyl and alkynyl group preferably contains 1–6, most preferably 1–4, carbon atoms.

(b) "heteroaryl" includes mono-, bi- and polycyclic aromatic heterocyclic groups containing 1–4 O, N or S atoms; preferred are 5- or 6-membered heterocyclic rings such as thienyl, furyl, thiadiazolyl, oxadiazolyl, triazolyl, isothiazolyl, thiazolyl, imidazolyl, isoxazolyl, tetrazolyl, oxazolyl, pyridyl, pyrazinyl, pyrimidinyl, pyridazinyl, pyrrolyl, pyrazolyl, etc.

(c) "heterocyclyl" includes mono-, bi- and polycyclic saturated or unsaturated non-aromatic heterocyclic groups containing 1–4 O, N or S atoms; preferred are 5- or 6-membered heterocyclic rings such as morpholinyl, piperazinyl, piperidyl, pyrazolinyl, pyrazolidinyl, imidazolinyl, imidazolidinyl, pyrrolinyl, pyrrolidinyl, etc.

(d) "halo" includes chloro, bromo, fluoro and iodo and is preferably chloro or bromo.

The term "conventional readily removable carboxyl protecting group" refers to a known ester group which has been employed to block a carboxyl group during the chemical reaction steps described below and which can be removed, if desired, by methods which do not result in any appreciable destruction of the remaining portion of the molecule, e.g. by chemical or enzymatic hydrolysis, treatment with chemical reducing agents under mild conditions, irradiation with ultraviolet light or catalytic hydrogenation. Examples of such ester protecting groups include benzhydryl, p-nitrobenzyl, 2-naphthylmethyl, allyl benzyl, trichloroethyl, silyl such as trimethylsilyl, phenacyl, p-methoxybenzyl, acetonyl, o-nitrobenzyl, 4-pyridylmethyl and $C_1$–$C_6$ alkyl such as methyl, ethyl or t-butyl. Included within such protecting groups are those which are hydrolyzed under physiological conditions such as pivaloyloxymethyl, acetoxymethyl, phthalidyl, indanyl and methoxymethyl. Particularly advantageous carboxyl protecting groups are p-nitrobenzyl which may be readily removed by catalytic hydrogenolysis and allyl which can be removed by $Pd(P\phi_3)_4$-catalyzed reaction.

The pharmaceutically acceptable salts referred to above include the nontoxic acid addition salts, e.g. salts with mineral acids such as hydrochloric, hydrobromic, hydroiodic, phosphoric, sulfuric, etc. and salts with organic acids such as maleic, acetic, citric, succinic, benzoic, tartaric, fumaric, mandelic, ascorbic, lactic, gluconic and malic. Compounds of formula I in the form of acid addition salts may be written as

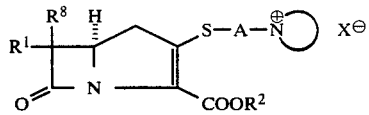

$R^2$=H or protecting group where $X^\ominus$ represents the acid anion. The counter anion $X^\ominus$ may be selected so as to provide pharmaceutically acceptable salts for therapeutic administration but, in the case of intermediate compounds of formula I, $X^\ominus$ may also be a toxic anion. In such a case the ion can be subsequently removed or substituted by a pharmaceutically acceptable anion to form an active end product for therapeutic use. When acidic or basic groups are present in the $R^1$ group or on the

radical, the present invention may also include suitable base or acid salts of these functional groups, e.g. acid addition salts in the case of a basic group and metal salts (e.g. sodium, potassium, calcium and aluminum), the ammonium salt and salts with nontoxic amines (e.g. trialkylamines, procaine, dibenzylamine, 1-ephenamine, N-benzyl-$\beta$-phenethylamine, N,N'-dibenzylethylenediamine, etc.) in the case of an acidic group.

Compounds of formula I wherein $R^2$ is hydrogen, an anionic charge or a physiologically hydrolyzable ester group together with pharmaceutically acceptable salts thereof are useful as antibacterial agents. The remaining compounds of formula I are valuable intermediates which can be converted into the above-mentioned biologically active compounds.

A preferred embodiment of the present invention comprises compounds of formula I wherein $R^8$ is hydrogen and $R^1$ is hydrogen; $CH_3CH_2$—

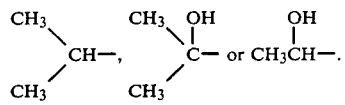

Among this subclass, the preferred compounds are those in which $R^1$ is

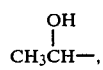

most preferably compounds having the absolute configuration 5R, 6S, 8R.

Another preferred embodiment comprises compounds of formula I in which $R^1$ and $R^8$ taken together form an alkylidene radical of the formula

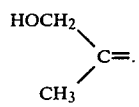

The alkylene or cycloalkylene substituent A in the compounds of Formula I may be $C_2$–$C_6$ alkylene (straight chain) optionally substituted by one or more (preferably 1 or 2) $C_1$–$C_4$ alkyl groups or it may be cyclopentylene or cyclohexylene. The alkylene A substituent is preferably straight or branched chain alkylene of from 2 to 6 carbon atoms. A cycloalkylene A substituent is preferably cyclopentylene of the formula

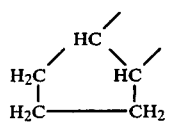

or cyclohexylene of the formula

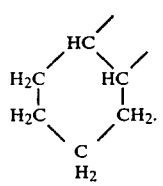

A preferred embodiment comprises those compounds in which A is

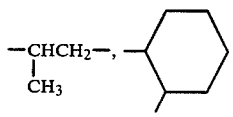

or —(CH$_2$)$_n$— in which n is 2, 3 or 4 and a particularly preferred embodiment comprises those compounds where A is —CH$_2$CH$_2$—, —CH$_2$CH$_2$CH$_2$—,

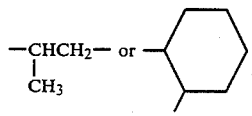

The

substituent of formula I may be a substituted or unsubstituted mono-, bi- or polycyclic heteroaryl radical containing at least one nitrogen in the ring and attached to A through a ring nitrogen, thereby forming a quaternary ammonium group. The heteroaryl radical may be optionally substituted by such substituents as C$_1$–C$_4$ alkyl, C$_1$–C$_4$ alkyl substituted by hydroxy, amino, carboxy or halo, C$_3$–C$_6$ cycloalkyl, C$_1$–C$_4$ alkoxy, C$_1$–C$_4$ alkylthio, amino, C$_1$–C$_4$ alkylamino, di(C$_1$–C$_4$ alkyl)amino, halo, C$_1$–C$_4$ alkanoylamino, C$_1$–C$_4$ alkanoyloxy, carboxy,

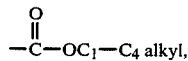

hydroxy, amidino, guanidino, trifluoromethyl, phenyl, phenyl substituted by one, two or three amino, halo, hydroxyl, trifluoromethyl, C$_1$–C$_4$ alkyl or C$_1$–C$_4$ alkoxy groups, heteroaryl and heteroaralkyl in which the hetero atom or atoms in the above-named heterocyclic moieties are selected from the group consisting of 1–4 O, N or S atoms and the alkyl moiety associated with heteroaralkyl has 1–6 carbon atoms.

The heteroaryl radical attached to substituent A is preferably a 5- or 6-membered aromatic heterocyclic radical containing a quaternized nitrogen atom (which is directly bonded to a carbon atom of the alkylene or cycloalkylene radical) and, optionally, one or more additional hetero atoms selected from O, N or S. While, in general, any heteroaryl radical bonded to substituent A via a quaternized nitrogen atom is found to produce biologically active carbapenem derivatives, a preferred embodiment comprises compounds of formula I in which

represents a radical selected from the group consisting of

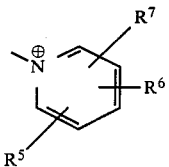

(a)

wherein R$^5$, R$^6$ and R$^7$ are independently selected from hydrogen; C$_1$–C$_4$ alkyl; C$_1$–C$_4$ alkyl substituted by hydroxy, amino, carboxy or halo; C$_3$–C$_6$ cycloalkyl; C$_1$–C$_4$ alkoxy; C$_1$–C$_4$ alkylthio; amino; C$_1$–C$_4$ alkylamino; di(C$_1$–C$_4$ alkyl)amino; halo; C$_1$–C$_4$ alkanoylamino; C$_1$–C$_4$ alkanoyloxy; carboxy;

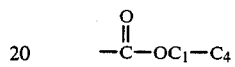

alkyl; hydroxy; amidino; guanidino; trifluoromethyl; phenyl; phenyl substituted by one, two or three amino, halo, hydroxyl, trifluoromethyl, C$_1$–C$_4$ alkyl or C$_1$–C$_4$ alkoxy groups; and heteroaryl and heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms; or wherein two of R$^5$, R$^6$ or R$^7$ taken together may be a fused saturated carbocyclic ring, a fused aromatic carbocyclic ring, a fused saturated heterocyclic ring or a fused heteroaromatic ring;

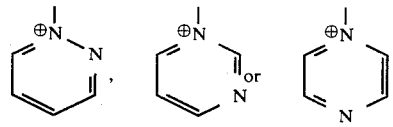

(b)

optionally substituted on a carbon atom by one or more substituents independently selected from C$_1$–C$_4$ alkyl; C$_1$–C$_4$ alkyl substituted by hydroxy, amino, carboxy or halogen; C$_3$–C$_6$ cycloalkyl; C$_1$–C$_4$ alkoxy; C$_1$–C$_4$ alkylthio; amino; C$_1$–C$_4$ alkylamino; di(C$_1$–C$_4$ alkyl)amino; halo; C$_1$–C$_4$ alkanoylamino; C$_1$–C$_4$ alkanoyloxy; carboxy;

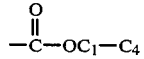

alkyl; hydroxy; amidino; guanidino; trifluoromethyl; phenyl; phenyl substituted by one, two or three amino, halo, hydroxyl, trifluoromethyl, C$_1$–C$_4$ alkyl or C$_1$–C$_4$ alkoxy groups; and heteroaryl or heteroaralkyl in which the heteroatom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or optionally substituted so as to form a fused carbocyclic or heterocyclic ring;

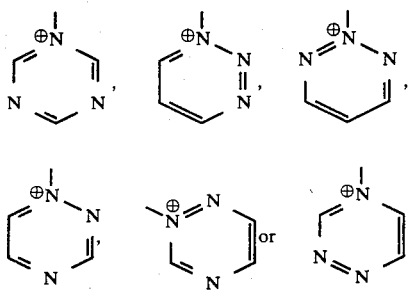

optionally substituted on a carbon atom by one or more substituents independently selected from $C_1$-$C_4$ alkyl; $C_1$-$C_4$ alkyl substituted by hydroxy, amino, carboxy or halogen; $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo; $C_1$-$C_4$ alkanoylamino; $C_1$-$C_4$ alkanoyloxy; carboxy;

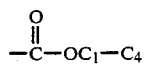

alkyl; hydroxy; amidino; guanidino; trifluoromethyl; phenyl; phenyl substituted by one, two or three amino, halo, hydroxyl, trifluoromethyl, $C_1$-$C_4$ alkyl or $C_1$-$C_4$ alkoxy groups; and heteroaryl or heteroaralkyl in which the heteroatom or atoms in the above-named heterocyclic moieties are selected from the group consisting of 1-4 oxygen, nitrogen or sulfur atoms and the alkyl moiety associated with said heteroaralkyl moiety has 1-6 carbon atoms, or optionally substituted so as to form a fused carbocyclic or heterocyclic ring;

(d)

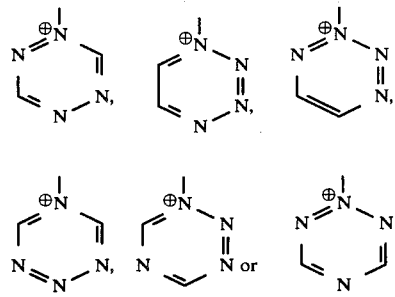

optionally substituted on a carbon atom by one or more substituents independently selected from $C_1$-$C_4$ alkyl; $C_1$-$C_4$ alkyl substituted by hydroxy, amino, carboxy or halogen; $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo; $C_1$-$C_4$ alkanoylamino; $C_1$-$C_4$ alkanoyloxy; carboxy;

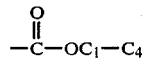

alkyl; hydroxy; amidino; guanidino; trifluoromethyl; phenyl; phenyl substituted by one, two or three amino, halo, hydroxyl, trifluoromethyl, $C_1$-$C_4$ alkyl or $C_1$-$C_4$ alkoxy groups; and heteroaryl or heteroaralkyl in which the heteroatom or atoms in the above-named heterocyclic moieties are selected from the group consisting of 1-4 oxygen, nitrogen or sulfur atoms and the alkyl moiety associated with said heteroaralkyl moiety has 1-6 carbon atoms, or optionally substituted so as to form a fused carbocyclic or heterocyclic ring;

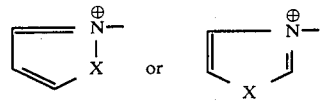

wherein X is O, S or NR in which R is $C_1$-$C_4$ alkyl or phenyl, said radical being optionally substituted on a carbon atom by one or more substituents independently selected from $C_1$-$C_4$ alkyl; $C_1$-$C_4$ alkyl substituted by hydroxy, amino, carboxy or halogen; $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo; $C_1$-$C_4$ alkanoylamino; $C_1$-$C_4$ alkanoyloxy; carboxy;

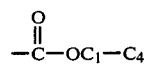

alkyl; hydroxy; amidino; guanidino; trifluoromethyl; phenyl; phenyl substituted by one, two or three amino, halo, hydroxyl, trifluoromethyl, $C_1$-$C_4$ alkyl or $C_1$-$C_4$ alkoxy groups; and heteroaryl or heteroaralkyl in which the heteroatom or atoms in the above-named heterocyclic moieties are selected from the group consisting of 1-4 oxygen, nitrogen or sulfur atoms and the alkyl moiety associated with said heteroaralkyl moiety has 1-6 carbon atoms, or optionally substituted so as to form a fused carbocyclic or heterocyclic ring;

(f)

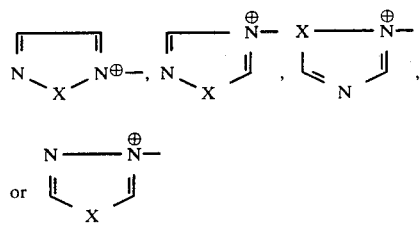

wherein X is O, S or NR in which R is $C_1$-$C_4$ alkyl or phenyl, said radical being optionally substituted on a carbon atom by one or more substituents independently selected from $C_1$-$C_4$ alkyl; $C_1$-$C_4$ alkyl substituted by hydroxy, amino, carboxy or halogen; $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; halo; $C_1$-$C_4$ alkanoylamino; $C_1$-$C_4$ alkanoyloxy; carboxy;

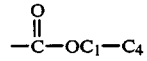

alkyl; hydroxy; amidino; guanidino; trifluoromethyl; phenyl; phenyl substituted by one, two or three amino, halo, hydroxyl, trifluoromethyl, $C_1$-$C_4$ alkyl or $C_1$-$C_4$ alkoxy groups; and heteroaryl or heteroaralkyl in which the heteroatom or atoms in the above-named heterocyclic moieties are selected from the group consisting of 1-4 oxygen, nitrogen or sulfur atoms and the alkyl moiety associated with said heteroaralkyl moiety has 1-6 carbon atoms; and

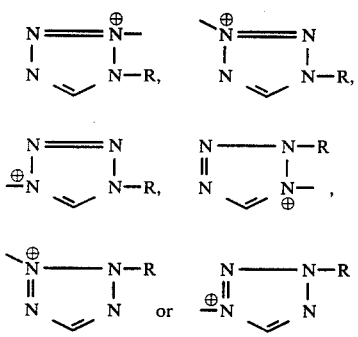

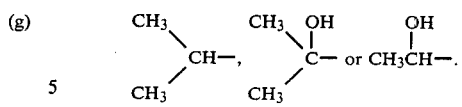

wherein R is $C_1$-$C_4$ alkyl or phenyl, said radical being optionally substituted on the carbon atom by a substituent selected from $C_1$-$C_4$ alkyl; $C_1$-$C_4$ alkyl substituted by hydroxy; amino, carboxy or halogen; $C_3$-$C_6$ cycloalkyl; $C_1$-$C_4$ alkoxy; $C_1$-$C_4$ alkylthio; amino; $C_1$-$C_4$ alkylamino; di($C_1$-$C_4$ alkyl)amino; $C_1$-$C_4$ alkanoylamino; carboxy;

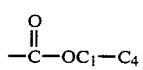

alkyl; hydroxy; amidino; guanidino; trifluoromethyl; phenyl, phenyl substituted by one, two or three amino, halo, hydroxyl, trifluoromethyl, $C_1$-$C_4$ alkyl or $C_1$-$C_4$ alkoxy groups; and heteroaryl or heteroaralkyl in which the hetero atom or atoms in the above-named heterocyclic moieties are selected from the group consisting of 1-4 oxygen, nitrogen or sulfur atoms and the alkyl moiety associated with said heteroaralkyl moiety has 1-6 carbon atoms.

Within the above subclass, the preferred compounds are those in which A is

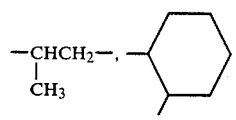

or —$(CH_2)_n$— in which n is 2, 3 or 4, most preferably those in which A is —$CH_2CH_2$—, —$CH_2CH_2CH_2$—,

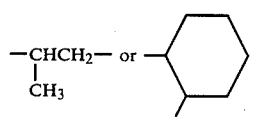

and wherein either (a) $R^1$ and $R^8$ taken together represent

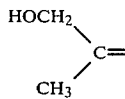

or (b) $R^8$ is hydrogen and $R^1$ represents hydrogen, $CH_3CH_2$—,

Particularly preferred are the compounds wherein $R^8$ is hydrogen and $R^1$ is

preferably compounds having the absolute configuration 5R, 6S, 8R.

A particularly preferred embodiment of the present invention comprises compounds of formula I wherein

represents a radical of the formula

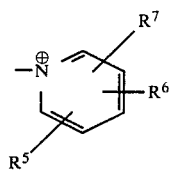

in which $R^5$, $R^6$ and $R^7$ are independently selected from the group consisting of hydrogen, $C_1$-$C_4$ alkyl, $C_1$-$C_4$ alkoxy, $C_1$-$C_4$ alkyl substituted by a hydroxy group, $C_1$-$C_4$ alkylthio, amino, carboxy and carbamoyl. Within this subclass, the preferred compounds are those wherein A is

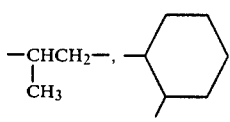

or —$(CH_2)_n$— in which n is 2, 3 or 4, most preferably those in which A is —$CH_2CH_2$—, —$CH_2CH_2CH_2$—,

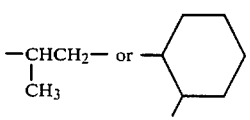

and wherein either (a) $R^1$ and $R^8$ taken together represent

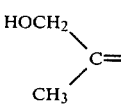

or (b) $R^8$ is hydrogen and $R^1$ represents hydrogen, $CH_3CH_2$—,

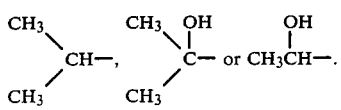

Particularly preferred are the compounds wherein $R^8$ is hydrogen and $R^1$ is

preferably compounds having the absolute configuration 5R, 6S, 8R.

Another preferred embodiment comprises the compounds of formula I wherein

represents a radical of the formula

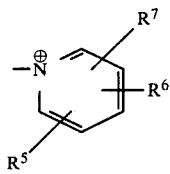

in which $R^5$, $R^6$ and $R^7$ are independently selected from the group consisting of hydrogen, $C_1$-$C_4$ alkyl, $C_1$-$C_4$ alkoxy, $C_1$-$C_4$ alkyl substituted by a hydroxy group, $C_1$-$C_4$ alkylthio and amino. Within this subclass, the preferred compounds are those wherein A is

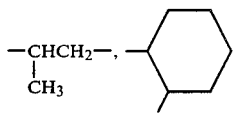

or —$(CH_2)_n$ in which n is 2, 3 or 4, most preferably those in which A is —$CH_2CH_2$—, —$CH_2CH_2CH_2$—,

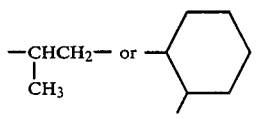

and wherein either (a) $R^1$ and $R^8$ taken together represent

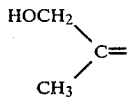

or (b) $R^8$ is hydrogen and $R^1$ represents hydrogen, $CH_3CH_2$—,

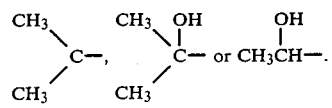

Particularly preferred are the compounds wherein $R^8$ is hydrogen and $R^1$ is

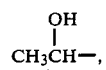

preferably compounds having the absolute configuration 5R, 6S, 8R.

Another preferred embodiment of the present invention comprises compounds of formula I wherein

represents a radical of the formula

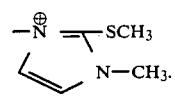

Within this subclass, the preferred compounds are those wherein A is

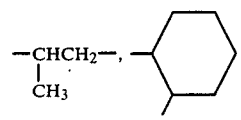

or —$(CH_2)_n$— in which n is 2, 3 or 4, most preferably those in which A is —$CH_2CH_2$—, —$CH_2CH_2CH_2$—,

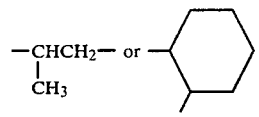

and wherein either (a) $R^1$ and $R^8$ taken together represent

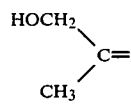

or (b) $R^8$ is hydrogen and $R^1$ represents hydrogen, $CH_3CH_2$—,

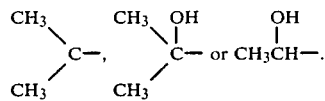

Particularly preferred are the compounds wherein $R^8$ is hydrogen and $R^1$ is

preferably compounds having the absolute configuration 5R, 6S, 8R.

Another preferred embodiment of the present invention comprises compounds of formula I wherein

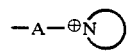

represents a pyridinium radical. Within this subclass, the preferred compounds are those wherein A is

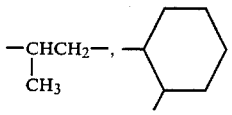

or —(CH$_2$)$_n$ in which n is 2, 3 or 4, most preferably those in which A is —CH$_2$CH$_2$—, —CH$_2$CH$_2$CH$_2$—,

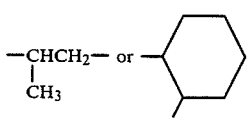

and wherein either (a) R$^1$ and R$^8$ taken together represent

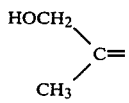

or (b) R$^8$ is hydrogen and R$^1$ represents hydrogen, CH$_3$CH$_2$—,

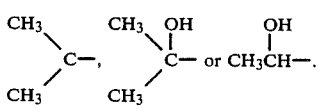

Particularly preferred are the compounds wherein R$^8$ is hydrogen and R$^1$ is

preferably compounds having the absolute configuration 5R, 6S, 8R.

The most preferred embodiments of the present invention comprise the compounds of the formula

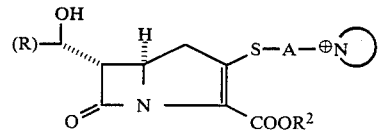

wherein

—A—$\overset{\oplus}{N}$⟨ ⟩ represents

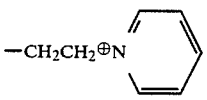 (1)

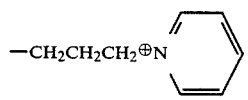 (2)

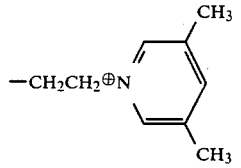 (3)

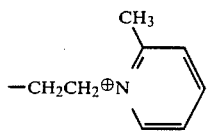 (4)

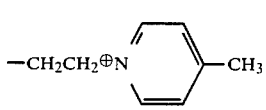 (5)

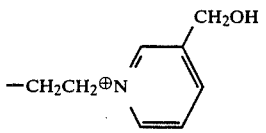 (6)

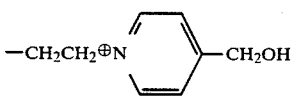 (7)

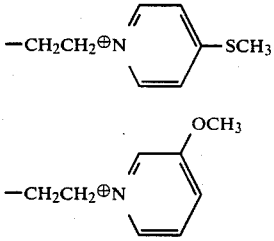 (8)

(9)

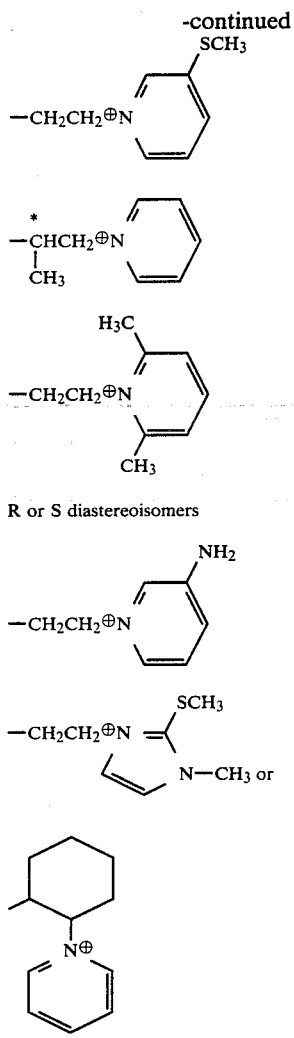

R or S diastereoisomers

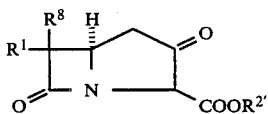

R,R or S,S diastereoisomers at the two assymetric carbons of the cyclohexyl ring and $R^2$ is hydrogen, an anionic charge or a conventional readily removable carboxyl protecting group, providing that when $R^2$ is hydrogen or a protecting group, there is also present a counter anion, and pharmaceutically acceptable acid addition salts thereof.

The carbapenem derivatives of general formula I are prepared from starting materials of the formula

III wherein $R^1$ and $R^8$ are defined above and wherein $R^{2'}$ represents a conventional readily removable carboxyl protecting groups. Compounds of formula III have been disclosed, for example, in European Patent Application No. 38,869 (compound 7) and may be prepared by the general methods described therein.

One process for preparing compounds I from starting materials III may be summarized by the following reaction scheme:

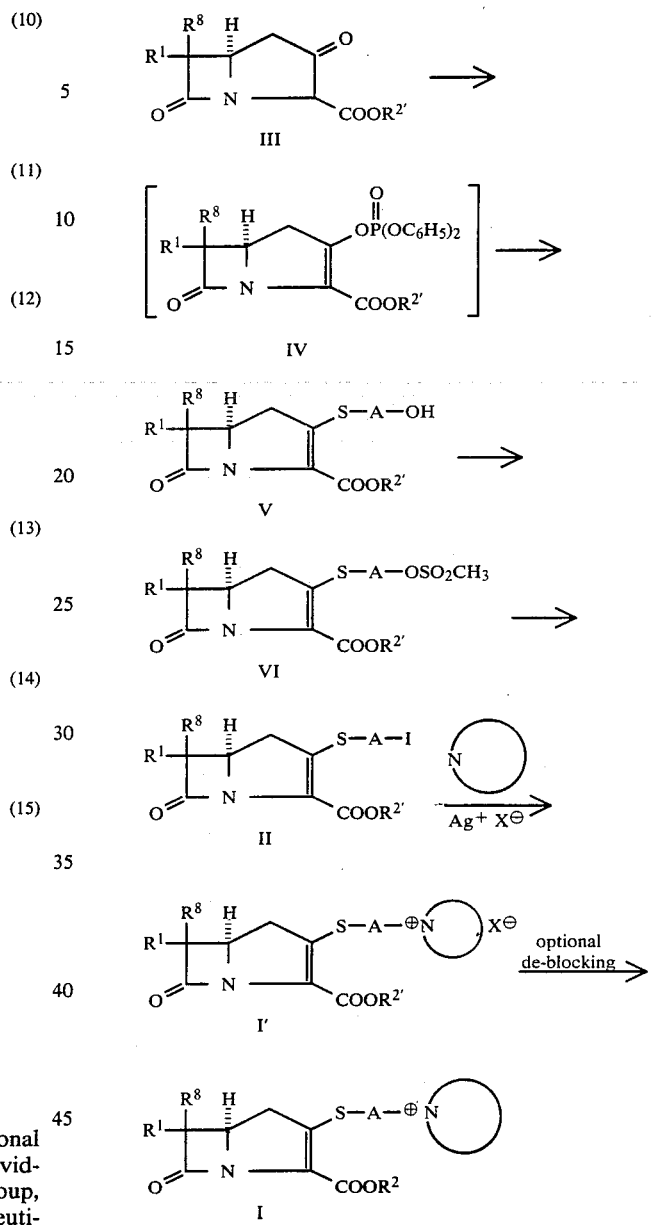

To elaborate on the above process, starting material III is reacted in the inert organic solvent such as methylene chloride, acetonitrile or dimethylformamide with about an equimolar amount of diphenyl chlorophosphate in the presence of a base such as diisopropylethylamine, triethylamine, 4-dimethylaminopyridine or the like to give intermediate IV. The acylation to establish the diphenylphosphoryloxy leaving group at the 2-position of intermediate III is advantageously carried out at a temperature of from about −20° to +40° C., most preferably at about 0° C. Intermediate IV may be isolated if desired, but is conveniently used for the next step without isolation or purification.

Intermediate IV is next converted to intermediate V by a conventional displacement reaction. Thus, intermediate IV may be reacted with approximately an equimolar amount of a mercaptan reagent of the formula

HS—A—OH wherein A represents cyclopentylene, cyclohexylene or $C_2$-$C_6$ alkylene optionally substituted by one or more $C_1$-$C_4$ alkyl groups in an inert organic solvent such as dioxane, dimethylformamide, dimethylsulfoxide or acetonitrile and in the presence of a base such as diisopropylethylamine, triethylamine, sodium hydrogen carbonate, potassium carbonate or 4-dimethylaminopyridine. The temperature for the displacement is not critical, but an advantageous temperature range is from about −40° C. to 25° C. Most conveniently, the reaction is carried out with cooling, e.g. at about 0° C.

Intermediate V is then acylated with methanesulfonyl chloride or a functional acylating equivalent thereof such as methanesulfonic acid anhydride in an inert organic solvent and in the presence of base to provide the methanesulfonyloxy leaving group of intermediate VI. The acylation is carried out in an inert organic solvent such as tetrahydrofuran, methylene chloride, acetonitrile or dimethylformamide and in the presence of a suitable base such as diisopropylethylamine, triethylamine, 4-dimethylaminopyridine, and the like. The reaction may be carried out over a wide temperature range, e.g. −40° C. to +40° C., but is most advantageously conducted with cooling, e.g. at about −30° C. to −40° C.

Intermediate VI is next subjected to a displacement reaction so as to provide in intermediate II the iodo leaving group. This particular group has been found to greatly facilitate preparation of the carbapenem endproducts of formula I. The novel intermediates of general formula II, therefore, comprise a preferred embodiment of the present invention.

The displacement of the methanesulfonyloxy leaving group is carried out by reacting intermediate VI with a source of iodide ions in an inert organic solvent such as acetone, dimethylformamide or dimethylsulfoxide. Any compound which ionizes in the solvent employed to provide iodide ions may be used, e.g. an alkali metal iodide such as NaI or KI. The temperature for the displacement is not critical, but temperatures of room temperature or above are most advantageous for achieving completion of the reaction in a reasonable time period. The source of iodide ions is employed in an amount so as to provide approximately an equivalent or excess of iodide ion relative to intermediate VI.

Preparation of the desired carbapenem derivatives of formula I is carried out by a nucleophilic displacement of the iodo leaving group of intermediate II by the desired nitrogen-containing heteroaromatic nucleophile

Intermediate II is reacted with at least an equivalent, preferably an excess, of the desired heteroaryl reagent in an inert organic solvent and in the presence of silver ion. Suitable inert organic solvents include, for example, tetrahydrofuran, dioxane, methylene chloride, diglyme, dimethoxyethane, and the like. Any silver compound which substantially ionizes in the solvent to give silver ions and an inert anion may be used as the source of silver ion, e.g. $AgClO_4$. Generally, we prefer to use approximately an equivalent amount (relative to intermediate II) of silver ion to facilitate the displacement. The reaction may be carried out over a wide temperature range, e.g. from about −25° to about +25° C., but is most preferably conducted at around 0° C. Intermediate I' will have a counter anion (derived from the silver salt used) associated with it which may at this stage be substituted by a different counter anion, e.g. one which is pharmaceutically acceptable, by conventional procedures. Alternatively, the counter ion may be subsequently removed during the de-blocking step.

The de-blocking step to remove the carboxyl protecting group $R^{2'}$ of intermediate I' is accomplished by conventional procedures such as solvolysis, chemical reduction or hydrogenation. Where a protecting group such as p-nitrobenzyl, benzyl, benzhydryl or 2-naphthylmethyl is used which can be removed by catalytic hydrogenation, intermediate I' in a suitable solvent such as dioxane-water-ethanol, tetrahydrofuran-aqueous dipotassium hydrogen phosphate-isopropanol or the like may be treated under a hydrogen pressure of from 1 to 4 atmospheres in the presence of a hydrogenation catalyst such as palladium on charcoal, palladium hydroxide, platinum oxide or the like at a temperature of from 0° to 50° C. for from about 0.24 to 4 hours. When $R^{2'}$ is a group such as o-nitrobenzyl, photolysis may also be used for deblocking. Protecting groups such as 2,2,2-trichloroethyl may be removed by mild zinc reduction. The allyl protecting group may be removed with a catalyst comprising a mixture of a palladium compound and triphenyl phosphine in an aprotic solvent such as tetrahydrofuran, diethyl ether or methylene chloride. Similarly, other conventional carboxyl protecting groups may be removed by methods known to those skilled in the art. Finally, as mentioned above, compounds of formula I' where $R^{2'}$ is a physiologically hydrolyzable ester such as acetoxymethyl, phthalidyl, indanyl, pivaloyloxymethyl, methoxymethyl, etc. may be administered directly to the host without de-blocking since such esters are hydrolyzed in vivo under physiological conditions.

While the above-described process is suitable for preparing the compounds of the present invention, our colleague Pierre Dextraze has invented a new process which can be used to prepare compounds of Formula I where substituent A is cyclopentylene, cyclohexylene or

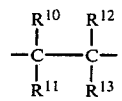

in which $R^{10}$, $R^{11}$, $R^{12}$ and $R^{13}$ are each independently hydrogen or $C_1$-$C_4$ alkyl. This process, which is disclosed and claimed in a co-pending U.S. Patent Application filed even date with the present continuation-in-part application is the preferred process for preparing the above-mentioned class of compounds.

The alternative process for preparing compounds of Formula I wherein A is cyclopentylene, cyclohexylene or

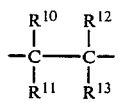

in which $R^{10}$, $R^{11}$, $R^{12}$ and $R^{13}$ are each independently hydrogen or $C_1$–$C_4$ alkyl comprises reacting an intermediate of the formula

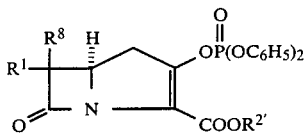    IV wherein $R^1$ and $R^8$ are as defined for the compounds of Formula I and $R^{2'}$ is a conventional readily removed carboxyl protecting group with a thiol compound of the formula

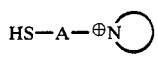    VII wherein A and

are as defined above in connection with the compounds of Formula I and $X^\ominus$ is a counter anion in an inert solvent and in the presence of base to produce carbapenem product of the formula

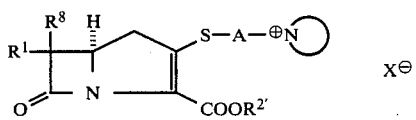    I' wherein $R^1$, $R^8$, $R^{2'}$, A,

and $X^\ominus$ are as defined above and, if desired, removing the carboxyl protecting group $R^{2'}$ to give the corresponding de-blocked compound of Formula I, or a pharmaceutically acceptable salt thereof.

The above alternative process utilizes intermediate IV which may be prepared as described above for the general synthetic process. Intermediate IV is generally prepared in situ from intermediate III and used without isolation or purification.

In the alternative process, carbapenem intemediate IV is reacted with a quaternary amine thiol of the formula

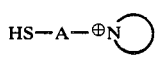    VII wherein A is cyclopentylene, cyclohexylene or

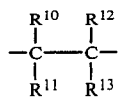

in which $R^{10}$, $R^{11}$, $R^{12}$ and $R^{13}$ are each independently hydrogen or $C_1$–$C_4$ alkyl, $X^\ominus$ is a counter anion associated with a strong acid such as $Cl^-$, $Br^-$, $CH_3SO_3^-$, $CF_3SO_3^-$ or

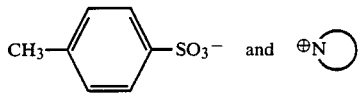

is as defined above. The reaction is carried out in an inert solvent such as acetonitrile, acetonitrile-$H_2O$, acetonitriledimethylformamide or acetone in the presence of base. The nature of the base is not critical. Best results, however, have been obtained when a non-nucleophilic tertiary amine base such as diisopropylethylamine, 1,8-diazabicyclo[5.4.0]undec-7-ene, 1,5-diazabicyclo[4.3.0]non-5-ene or a tri($C_1$–$C_4$)alkylamine such as triethylamine, tributylamine or tripropylamine is employed. Reaction of intermediate IV with thiol VII may be carried out over a wide temperature range, e.g. $-15°$ C. up to room temperature, but is preferably done at a temperature in the range of from about $-15°$ C. to $+15°$ C., most preferably at around 0° C.

The carbapenem product produced by reaction of the quaternary amine thiol VII with intermediate IV will have a counter anion associated with it (i.e. $(C_6H_5O)_2PO_2^\ominus$, $Cl^\ominus$ or the anion associated with the quaternary thiol) which may at this stage be substituted by a different counter anion, e.g. one which is more pharmaceutically acceptable, by conventional procedures. Alternatively, the counter anion may be removed during the subsequent deblocking step. Where the quaternized carbapenem compound and counter anion form an insoluble product, the product may crystallize out as it is formed and be collected pure by filtration.

Following formation of the desired carbapenem product according to the above-described reaction step, the carboxyl protecting group $R^{2'}$ of compound I' may be optionally removed by conventional procedures as described above in connection with the general synthetic process.

The thiol intermediates of Formula VII may be prepared by reacting a sulfide of the formula

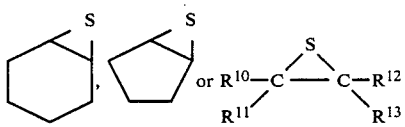

VIIIa    VIIIb    VIIIc wherein $R^{10}$, $R^{11}$, $R^{12}$ and $R^{13}$ are each independently hydrogen or $C_1$–$C_4$ alkyl with a heteroaromatic amine (as defined above) of the formula

and a strong acid. The reaction may be carried out in the presence or absence of an inert organic solvent which is preferably a non-polar organic solvent such as methylene chloride, benzene, xylene, toluene or the like. Where the amine and sulfide reagents are liquids or where a solid amine is soluble in a liquid sulfide reagent, it is preferred to carry out the reaction without use of an additional solvent.

The particular strong acid used in the reaction is not critical and may be, for example, such strong inorganic or organic acids as hydrochloric, hydrobromic, methanesulfonic, p-toluenesulfonic, trifluoromethanesulfonic, etc.

Formation of the quaternary amine thiol intermediate VII may be carried out at a temperature in the range of from about $-20°$ C. to about $100°$ C. Preferred temperatures are generally in the range of about $50°-70°$ C.

The sulfide reagent, aromatic amine and acid are preferably employed so that the sulfide and acid are used in approximately equimolar amounts with the amine being used in excess, e.g. two to three moles of amine per mole of sulfide or acid.

The quaternary amine thiol intermediate will have a counter anion associated with it which will be determined by the particular acid employed. It is, of course, possible to substitute at this point a different counter anion by conventional procedures for use in the subsequent reaction with carbapenem intermediate IV.

It will be understood that where the $R^1$ and/or $R^8$ substituent or the heteroaromatic nucleophile attached to substituent A contain a functional group which might interfere with the intended course of reaction, such group may be protected by a conventional blocking group and then subsequently de-blocked to regenerate the desired functional group. Suitable blocking groups and procedures for introducing and removing such groups are well known to those skilled in the art.

In the case of certain compounds of Formula I having a cycloalkylene or branched alkylene A substituent, one or more additional assymmetric carbon atoms may be created which result in formation of diastereoisomers. The present invention includes mixtures of such diastereoisomers as well as the individual purified diastereoisomers.

As in the case of other β-lactam antibiotics, compounds of general formula I may be converted by known procedures to pharmaceutically acceptable salts which, for purposes of the present invention, are substantially equivalent to the nonsalted compounds. Thus, for example, one may dissolve a compound of formula I wherein $R^2$ is an anionic charge in a suitable inert solvent and then add an equivalent of a pharmaceutically acceptable acid. The desired acid addition salt may be recovered by conventional procedures, e.g. solvent precipitation, lyophilization, etc. Where other basic or acidic functional groups are present in the compound of formula I, pharmaceutically acceptable base addition salts and acid addition salts may be similarly prepared by known methods.

A compound of formula I where $R^2$ is hydrogen or an anionic charge, or a pharmaceutically acceptable salt thereof may also be converted by conventional procedures to a corresponding compound where $R^2$ is a physiologically hydrolyzable ester group, or a compound of formula I wherein $R^2$ is a conventional carboxyl protecting group may be converted to the corresponding compound where $R^2$ is hydrogen, an anionic charge or a physiologically hydrolyzable ester group, or a pharmaceutically acceptable salt thereof.

The novel carbapenem derivatives of general formula I wherein $R^2$ is hydrogen, an anionic charge or a physiologically hydrolyzable carboxyl protecting group, or the pharmaceutically acceptable salts thereof, are potent antibiotics active against various gram-positive and gram-negative bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are especially useful, however, in the treatment of infectious disease in humans and other animals caused by gram-positive or gram-negative bacteria.

The pharmaceutically active compounds of this invention may be used alone or formulated as pharmaceutical compositions comprising, in addition to the active carbapenem ingredient, a pharmaceutically acceptable carrier or diluent. The compounds may be administered by a variety of means; those of principal interest include: orally, topically or parenterally (intravenous or intramuscular injection). The pharmaceutical compositions may be in solid form such as capsules, tablets, powders, etc. or in liquid form such as solutions, suspensions or emulsions. Compositions for injection, the preferred route of delivery, may be prepared in unit dose form in ampules or in multidose containers and may contain formulatory agents such as suspending, stabilizing and dispersing agents. The compositions may be in ready to use form or in powder form for reconstitution at the time of delivery with a suitable vehicle such as sterile water.

The dosage to be administered depends to a large extent on the particular compound being used, the particular composition formulated, the route of administration, the nature and condition of the host and the particular situs and organism being treated. Selection of the particular preferred dosage and route of application, then, is left to the discretion of the therapist. In general, however, the compounds may be administered parenterally or orally to mammalian hosts in an amount of from about 5 to 200 mg/kg/day. Administration is generally carried out in divided doses, e.g. three to four times a day.

To illustrate the potent broad-spectrum antibacterial activity of the carbapenems of the present invention, both in vitro and in vivo, and the low toxicity of the compounds, biological data is provided below relating to the presently preferred carbapenem compounds of the present invention.

In Vitro Activity

A sample of the above-identified carbapenem compound after solution in water and dilution with Nutrient Broth was found to exhibit the following Minimum Inhibitory Concentrations (M.I.C.) in mcg/ml versus the indicated microorganisms as determined by overnight incubation at $37°$ C. by tube dilution. N-Formimidoyl thienamycin was included as a comparison compound.

In Vitro Antibacterial Activity of Carbapenem Derivative of Example 1

| Organism | | MIC (mcg/ml) | |
|---|---|---|---|
| | | New Compound | N—Formimidoyl Thienamycin |
| S. pneumoniae | A-9585 | 0.002 | 0.004 |
| S. pyogenes | A-9604 | 0.008 | 0.001 |
| S. aureus | A-9537 | 0.008 | 0.004 |
| S. aureus + 50% serum | A-9537 | 0.03 | 0.016 |
| S. aureus | A-9606 | 0.016 | 0.008 |
| (Pen-res.) | | | |
| S. aureus (Meth-res.) | A15097 | 4 | 0.5 |
| S. faecalis | A20688 | 0.5 | 0.5 |
| E. coli ($10^{-4}$ dil.) | A15119 | 0.03 | 0.016 |
| E. coli ($10^{-3}$) | A15119 | 0.06 | 0.03 |
| E. coli ($10^{-2}$) | A15119 | 0.06 | 0.06 |
| E. coli ($10^{-4}$) | A20341-1 | 0.03 | 0.03 |
| E. coli ($10^{-3}$) | A20341-1 | 0.06 | 0.03 |
| E. coli ($10^{-2}$) | A20341-1 | 0.13 | 0.13 |
| K. pneumoniae | A-9664 | 0.13 | 0.13 |
| K. pneumoniae | A20468 | 0.25 | 0.06 |
| P. mirabilis | A-9900 | 0.13 | 0.06 |
| P. vulgaris | A21559 | 0.03 | 0.03 |
| P. morganii | A15153 | 0.13 | 0.13 |
| P. rettgeri | A22424 | 0.5 | 0.25 |
| S. marcescens | A20019 | 0.06 | 0.03 |
| E. cloacae | A-9569 | 0.25 | 0.06 |
| E. cloacae | A-9656 | 0.13 | 0.06 |
| P. aeruginose | A-9843A | 2 | 1 |
| P. qeruginosa | A21213 | 0.13 | 0.25 |
| H. influenzae | A-9833 | 8 | 16 |
| H. influenzae | A20178 | 8 | 32 |
| H. influenzae | A21518 | 8 | 32 |
| H. influenzae | A21522 | 8 | 32 |
| B. fragilis | A22862 | 0.25 | 0.016 |
| B. fragilis | A22053 | 0.25 | 0.06 |
| B. fragilis | A22696 | 0.5 | 0.13 |
| B. fragilis | A22863 | 0.25 | 1 |

In Vivo Activity

The in vivo therapeutic efficacy of the compound of Example 1 and N-formimidoyl thienamycin after intramuscular administration to mice experimentally infected with various organisms is shown in the following Table. The $PD_{50}$ (dose in mg/kg required to give protection to 50% of the infected mice) is indicated.

Protective Effect in the Intramuscular Treatment of Infected Mice

| Organism | | Challenge (No. of organisms) | $PD_{50}$/Treatment (mg/kg) | |
|---|---|---|---|---|
| | | | Compound of Example 1 | N—Formimidoyl Thienamycin |
| S. aureus | A-9606 | $1 \times 10^9$ | 0.11 | 0.07* |
| E. coli | A15119 | $6 \times 10^6$ | – | 2.2* |
| K. pneumoniae | A-9664 | $7 \times 10^6$ | 7.7* | 2.4* |
| E. cloacae | A-9569 | $4 \times 10^6$ | 0.4 | — |
| P. mirabilis | A-9900 | $4 \times 10^6$ | 19 | 3*/15* |
| P. vulgaris | A21559 | $4 \times 10^5$ | 2.5 | – |
| P. rettgeri | A15167-2 | $3 \times 10^7$ | 5.7 | 6.9 |
| M. morganii | A15149 | $7 \times 10^5$ | 4.4 | – |
| S. marcescens | A20335 | $9 \times 10^6$ | 3.3 | – |
| P. aeruginosa | A-9843a | $3 \times 10^4$ | 0.8* | 0.5* |
| P. aeruginosa | A20481 | $3 \times 10^4$ | 0.8 | 0.4 |
| P. aeruginosa | A20599 | $9 \times 10^4$ | 3 | – |

*Historical data
Treatment Schedule: Mice were treated i.m. with drugs 0 and 2 hours post-infection (A21559, A15167-2, A9900, A9843a, A20481, A20599), or 1 and 3.5 hours (all others); 5 mice were used for each test.

Toxicity

The toxicity of the compound of Example 1 after intracranial administration to mice was determined and is shown in the following Table.

Toxicity After Intracranial Administration to Mice

| Compound | *$LD_{50}$ (mg/kg) | Highest Dose (mg/kg) Without Clinical Signs of Toxicity |
|---|---|---|
| Compound of Example 1 | >40 | >40 |
| N—Formimidoyl Thienamycin | 32 | ~5 |

*Average of 25 mice/compound

Blood Levels in Mice After Intramuscular Administration

Blood levels and the half-life of the compound of Example 1 after intramuscular administration of 20 mg/kg in mice are shown in the Table below.

| Compound | Blood Level (µg/ml) | | | | | | *$t_{\frac{1}{2}}$ (min) | **AUC (µg·h/mil) |
|---|---|---|---|---|---|---|---|---|
| | 10 | 20 | 30 | 45 | 60 | 90 | | |
| | Minutes after Administration | | | | | | | |
| Compound of Example 1 | 15.5 | 11.6 | 6.5 | 1.9 | 0.7 | <0.6 | 9 | 6.4 |
| N—Formimidoyl Thienamycin | 12.6 | 9.9 | 7.3 | 2.6 | 0.7 | <0.3 | 9 | 6 |

Compounds were solubilized in 0.1 M phosphate buffer pH 7.
Values are from a single test; 4 mice used per compound.
*$t_{\frac{1}{2}}$ refers to half-life in minutes
**AUC refers to the area under the curve

Urinary Recovery

The urinary recovery of the compound of Example 1 after intramuscular administration (20 mg/kg) to mice is shown in the following Table.

Urinary Recovery Intramuscular Administration of 20 mg/kg to Mice

| Compound | Percentage of Dose Recovered | | | |
|---|---|---|---|---|
| | 0–3 | 3–6 | 6–24 | 0–24 |
| | Hours After Administration | | | |
| Compound of Example 1 | 23.3 | 0.5 | 0.4 | 24.2 ± 5.3 |
| N—Formimidoyl | 12.1 | 0.1 | <0.1 | 12.2 ± 3.6 | by tube dilution. N-formimidoyl thienamycin was included as a comparison compound.

| | | MIC (μg/ml) | | | | | | | | |
|---|---|---|---|---|---|---|---|---|---|---|
| | | Compound (Example No.) | | | | | | | | |
| Organism | | Ex. 4 | Ex. 5 | Ex. 6 | Ex. 7 | Ex. 8 | *MK | Ex. 9 | Ex. 10 | Ex. 11 |
| S. pneumoniae | A-9585 | 0.03 | 0.03 | 0.03 | 0.03 | 0.03 | 0.002 | 0.002 | 0.002 | 0.001 |
| S. pyogenes | A-9604 | 0.03 | 0.03 | 0.03 | 0.03 | 0.03 | 0.002 | 0.001 | 0.002 | 0.001 |
| S. faecalis | A20688 | 0.5 | 0.5 | 1 | 0.5 | 0.5 | 0.5 | 0.25 | 0.25 | 0.25 |
| S. aureus | A-9537 | 0.03 | 0.03 | 0.03 | 0.03 | 0.03 | 0.001 | 0.008 | 0.008 | 0.004 |
| S. aureus (50% serum) | A-9537 | 0.03 | 0.06 | 0.13 | 0.03 | 0.06 | 0.016 | 0.016 | 0.06 | 0.03 |
| S. aureus (Pen-res) | A-9606 | 0.5 | 0.03 | 0.03 | 0.03 | 0.06 | 0.008 | 0.008 | 0.016 | 0.008 |
| S. aureus (Meth-res) | A15097 | >63 | >63 | >63 | >63 | >63 | 4 | | | |
| E. coli | A15119 | 0.06 | 0.06 | 0.03 | 0.03 | 0.13 | 0.016 | 0.03 | 0.03 | 0.03 |
| E. coli | A20341-1 | 0.06 | 0.06 | 0.03 | 0.03 | 0.13 | 0.03 | 0.03 | 0.06 | 0.03 |
| K. pneumoniae | A-9664 | 0.13 | 0.13 | 0.25 | 0.13 | 0.25 | 0.06 | 0.13 | 0.06 | 0.06 |
| K. pneumoniae | A20468 | 0.25 | 0.25 | 0.5 | 0.13 | 0.5 | 0.13 | 0.25 | 0.25 | 0.13 |
| E. cloacae | A9659 | 0.25 | 0.25 | 0.25 | 0.06 | 0.5 | 0.06 | 0.25 | 0.13 | 0.06 |
| E. cloacae | A-9656 | 0.25 | 0.25 | 0.25 | 0.13 | 0.5 | 0.06 | 0.13 | 0.13 | 0.13 |
| P. mirabilis | A-9900 | 0.25 | 0.13 | 0.06 | 0.03 | 0.13 | 0.06 | 0.06 | 0.13 | 0.13 |
| P. vulgaris | A21559 | 0.03 | 0.06 | 0.03 | 0.03 | 0.06 | 0.03 | 0.016 | 0.06 | 0.03 |
| M. morganii | A15153 | 0.25 | 0.13 | 0.03 | 0.03 | 0.03 | 0.13 | 0.13 | 0.13 | 0.13 |
| P. rettgeri | A22424 | 0.5 | 0.25 | 0.25 | 0.13 | 0.25 | 0.13 | 0.25 | 0.25 | 0.25 |
| S. marcescens | A20019 | 0.13 | 0.13 | 0.06 | 0.03 | 0.25 | 0.03 | 0.06 | 0.13 | 0.06 |
| P. aeruginosa | A-9843A | 32 | 2 | 1 | 4 | 8 | 1 | 4 | 4 | 4 |
| P. aeruginosa | A21213 | 2 | 0.25 | 0.5 | 1 | 0.5 | 0.25 | 2 | 1 | 1 |
| E. influenzae | A-9833 | >32 | >32 | >32 | >32 | >32 | 16 | | | |
| H. influenzae | A21518 | >32 | >32 | >32 | >32 | >32 | 32 | | | |
| B. fragilis | A22862 | 0.06 | 0.06 | 0.06 | 0.06 | 0.06 | 0.016 | 0.06 | 0.13 | 0.06 |
| B. fragilis | A22696 | 0.25 | 0.5 | 0.5 | 0.5 | 0.25 | 0.13 | 0.13 | 0.25 | 0.13 |

| | | Compound (Example No.) | | | | | | | | | |
|---|---|---|---|---|---|---|---|---|---|---|---|
| | | (cmp. "A") | | | (cmp. "B") | | | | | (cmp. "A") | |
| Organism | | Ex. 15 | Ex. 12 | *MK 0787 | Ex. 15 | Ex. 14 | *MK 0787 | Ex. 16 | Ex. 16 | Ex. 13 | *MK 0787 |
| S. pneumoniae | A-9585 | 0.004 | 0.002 | 0.002 | 0.001 | 0.002 | 0.002 | 0.002 | 0.004 | 0.001 | 0.002 |
| S. pyogenes | A-9604 | 0.004 | 0.002 | 0.002 | 0.001 | 0.004 | 0.002 | 0.004 | 0.004 | 0.002 | 0.002 |
| S. faecalis | A20688 | 2 | 0.25 | 0.25 | 0.5 | 0.5 | 0.25 | 8 | 4 | 0.5 | 0.25 |
| S. aureus | A-9537 | 0.016 | 0.008 | 0.002 | 0.004 | 0.008 | 0.002 | 0.13 | 0.06 | 0.008 | 0.002 |
| S. aureus (50% serum) | A-9537 | 0.06 | 0.03 | 0.016 | 0.016 | 0.016 | 0.016 | 0.13 | 0.06 | 0.03 | 0.016 |
| S. aureus (Pen-res) | A-9606 | 0.06 | 0.016 | 0.001 | 0.016 | 0.008 | 0.008 | 0.25 | 0.13 | 0.03 | 0.008 |
| S. aureus (Meth-res) | A15097 | | | | 0.03 | 0.008 | 0.008 | 0.5 | 0.25 | 0.13 | 0.008 |
| E. coli | A15119 | 0.03 | 0.03 | 0.016 | 0.008 | 0.03 | 0.016 | 0.25 | 0.06 | 0.03 | 0.016 |
| E. coli | A20341-1 | 0.03 | 0.016 | 0.016 | 0.016 | 0.03 | 0.016 | 0.06 | 0.06 | 0.03 | 0.016 |
| K. pneumoniae | A-9664 | 0.06 | 0.06 | 0.06 | 0.03 | 0.06 | 0.03 | 0.13 | 0.13 | 0.13 | 0.03 |
| K. pneumoniae | A20468 | 0.13 | 0.13 | 0.06 | 0.06 | 0.13 | 0.13 | 0.5 | 0.25 | 0.25 | 0.13 |
| E. cloacae | A-9659 | 0.13 | 0.25 | 0.06 | 0.06 | 0.13 | 0.13 | 0.5 | 0.25 | 0.25 | 0.13 |
| E. cloacae | A-9656 | 0.25 | 0.5 | 0.06 | 0.06 | 0.13 | 0.06 | 0.25 | 0.5 | 0.25 | 0.06 |
| P. mirabilis | A-9900 | 0.13 | 0.06 | 0.03 | 0.03 | 0.03 | 0.03 | 0.13 | 0.13 | 0.03 | 0.03 |
| P. vulgaris | A21559 | 0.03 | 0.03 | 0.016 | 0.016 | 0.016 | 0.016 | 0.13 | 0.06 | 0.03 | 0.016 |
| M. morganii | A15153 | 0.13 | 0.06 | 0.03 | 0.06 | 0.03 | 0.06 | 0.5 | 0.13 | 0.13 | 0.06 |
| P. rettgeri | A22424 | 0.25 | 0.5 | 0.06 | 0.06 | 0.13 | 0.13 | 4 | 4 | 0.25 | 0.13 |
| S. marcescens | A20019 | 0.06 | 0.06 | 0.03 | 0.03 | 0.06 | 0.03 | 0.25 | 0.13 | 0.06 | 0.03 |
| P. aeruginosa | A-9843A | 8 | >32 | 1 | 32 | 2 | 1 | 32 | 32 | 32 | 1 |
| P. aeruginosa | A21213 | 1 | 16 | 0.13 | 1 | 1 | 0.13 | 8 | 2 | 2 | 0.13 |
| E. influenzae | A-9833 | | | | | | | | | | |
| H. influenzae | A21518 | | | | | | | | | | |
| B. fragilis | A22862 | 0.13 | 0.06 | 0.03 | | | | | | | |
| B. fragilis | A22696 | 0.25 | 0.25 | 0.13 | | | | | | | |

*N—formimidoyl thienamycin

Urinary Recovery
Intramuscular Administration
of 20 mg/kg to Mice

| | Percentage of Dose Recovered | | | |
|---|---|---|---|---|
| | 0–3 | 3–6 | 6–24 | 0–24 |
| Compound | Hours After Adminstration | | | |
| Thienamycin | | | | |

Additional Biological Data

In Vitro Activity

Samples of the carbapenem compounds indicated below (identified by example number) after solution in water and dilution with Nutrient Broth were found to exhibit the following Minimum Inhibitory Concentrations (M.I.C.) in mcg/ml versus the indicated microorganisms as determined by overnight incubation at 37° C. by tube dilution.

In Vivo Activity

The in vivo therapeutic efficacy of several compounds of the present invention and N-formimidoyl thienamycin (MK 0787) after intramuscular administration to mice experimentally infected with various organisms is shown below. The $PD_{50}$ (dose in mg/kg required to give protection to 50% of the infected mice) is indicated.

| Protective Effect in the Intramuscular Treatment of Infected Mice | | | | |
|---|---|---|---|---|
| | PD$_{50}$/treatment (mg/kg) | | | |
| Compound | S. aureus | P. mirabilis | P. aeruginosa | |
| (Example No.) | A9606 | A9900 | A9843A | A20481 |
| Ex. 4 | 0.4 | ~22 | 5 | >5 |
| Ex. 5 | 0.5 | 22 | 0.9 | 0.8 |
| Ex. 6 | ~3 | ~16 | 0.9 | 0.6 |
| Ex. 7 | 0.6 | ~22 | 0.9 | 1.4 |
| Ex. 8 | 0.8 | ~38 | 0.9 | 2.5 |
| MK 0787 | 0.07 | 9 | 0.5 | 0.4 |

Treatment schedule: Mice were infected i.p. with ~1 × 10$^9$ organisms (A9606), ~1 × 10$^7$ (A9900), ~5 × 10$^4$ (A9843), or ~1 × 10$^5$ (A20481). Drugs were administered i.m. 0 and 2 hours post-infection (A9606) or 1 and 3.5 hours post-infection for the others.

The in vivo therapeutic efficacy of several compounds of the present invention and N-formimidoyl thienamycin (MK 0787) after intramuscular administration to mice experimentally infected with various organisms is shown below. The PD$_{50}$ (dose in mg/kg required to give protection to 50% of the infected mice) is indicated.

| Protective Effect in the Intramuscular Treatment of Infected Mice | | |
|---|---|---|
| | PD$_{50}$/treatment (mg/kg) | |
| Compound | P. mirabilis | P. aeruginosa |
| (Example No.) | A9900 | A9843A |
| Ex. 9 | — | 3.1 |
| Ex. 10 | — | 1.8 |
| Ex. 11 | — | 2.4 |
| Ex. 15 (cmp. "A") | — | 3.1 |
| Ex. 12 | — | >25 |
| Ex. 14 | 5.4 | 0.78 |
| MK 0787 | 19 | 1 |

Treament schedule: Mice were infected i.p. with 4 × 10$^7$ organisms (A9900), or 8 × 10$^4$ (A9843A), and treated with drugs i.m. 0 and 2 h post-infection.

Blood Levels and Urinary Recovery

Blood levels and the half-life of certain compounds of the present invention after intramuscular administration of 20 mg/kg in mice are shown below. Also shown is the urinary recovery in the mice.

| Pharmacokinetic Parameters in the Mouse After Intramuscular Dose of 20 mg/kg | | | | |
|---|---|---|---|---|
| | Blood | | | Urine |
| Compound | C$_{max}$ | *T$\frac{1}{2}$ | **AUC | Recovery |
| (Example No.) | (μg/ml) | (min) | (μg·h/ml) | % |
| Ex. 4 | 11.4 | 10.4 | 5.5 | 49 ± 6 |
| Ex. 6 | 15.2 | 10 | 7.7 | 38 ± 13 |
| Ex. 7 | 15 | 11 | 7 | 49 ± 9 |
| Ex. 8 | 10.6 | 8.2 | 4.6 | 47 ± 7 |
| MK 0787 | 14.6 | 10 | 6 | 33 ± 8 |

Compounds were solubilized in 0.1 M phosphate buffer pH 7.
Values based on a single test; 4 mice per compound, except for Ex. 7 which is average of two tests.
*T$\frac{1}{2}$ refers to half-life in minutes
**AUC refers to the area under the curve The following examples illustrate but do not limit the scope of the present invention.

EXAMPLE 1

Preparation of 3-[2-(1-Pyridinium)ethylthio]-6α-[1-(R)-hydroxyethyl]-7-oxo-1-azabicyclo(3.2.0)hept-2-ene-2-carboxylate

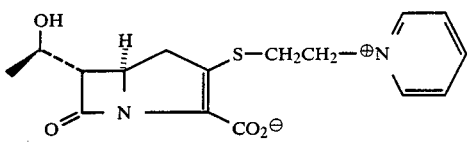

A. p-Nitrobenzyl 3-(2-hydroxyethylthio)-6α-[1-(R)-hydroxyethyl]-7-oxo-1-azabicyclo(3.2.0)hept-2-ene-2-carboxylate

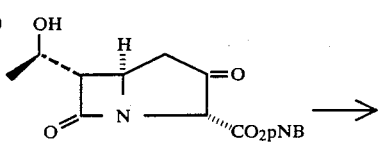

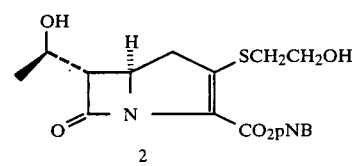

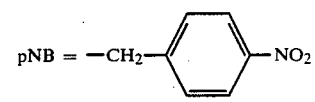

A solution of 1.69 g (4.85 mmole) of p-nitrobenzyl 6α-[1-(R)-hydroxyethyl]-3,7-dioxo-1-azabicyclo(3.2.0)hept-2-ene-2-carboxylate (1) in 20 ml of acetonitrile was cooled to 0° C. under a nitrogen atmosphere. A solution of 726 mg (7.18 mmole) of diisopropylethylamine in 2 ml of acetonitrile was added followed by a dropwise addition of 1.51 g (5.60 mmole) of diphenyl chlorophosphate in 12 ml of acetonitrile over a period of 3 minutes. The resulting solution was stirred at 0° for 20 minutes to provide p-nitrobenzyl 3-(diphenylphosphoryloxy)-6α-(1-(R)-hydroxyethyl]-7-oxo-1-azabicyclo(3.2.0)hept-2-ene-2-carboxylate. To this solution was added a solution of 726 mg (7.18 mmole) of diisopropylethylamine in 2 ml of acetonitrile followed by a solution of 439 mg (5.63 mmole) of 2-mercaptoethanol in 2 ml of acetonitrile. The reaction solution was stirred at 0° C. for 3 hours and then diluted with 200 ml of ethyl acetate and washed with 200 ml of water, 100 ml of 20% aqueous H$_3$PO$_4$, and brine. Evaporation of the dried (MgSO$_4$) solution gave a semisolid which was triturated with methylene chloride and filtered to yield 1.2 g (61% yield) of title product 2 as a white amorphous solid.

NMR (DMSO-d6) δ: 1.20 (3H, d, J=6.0 Hz), 2.9–3.2 (9H,m), 5.22(1H, d, J=8.5 Hz) and 8.23 (2H, d, J=8.5 Hz); ir (KBr) γmax: 3500, 1770 and 1700 cm$^{-1}$; Anal. Calc'd for C$_{18}$H$_{20}$N$_2$O$_7$S: C, 52.93; H, 4.94; N, 6.86; S, 7.85. Found: C, 52.83; H, 4.90; N, 6.42; S, 8.31.

B. p-Nitrobenzyl 3-(2-methanesulfonyloxyethylthio)-6α-[1-(R)-hydroxyethyl]-7-oxo-1-azabicyclo(3.2.0)hept-2-ene-2-carboxylate

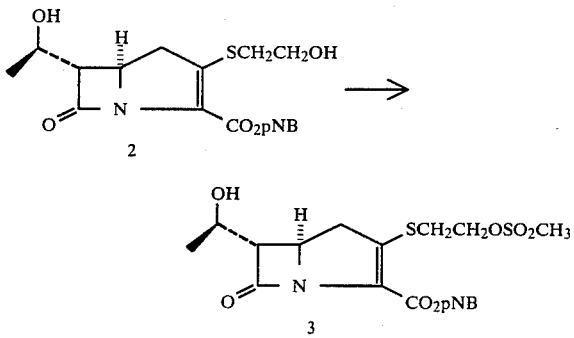

To a solution of 4.2 g (10.3 mmole) of 2 in 200 ml of tetrahydrofuran there was added at −40° C. 1.3 g (11.3 mmole) of methanesulfonyl chloride followed by a dropwise addition of 1.26 g (12.4 mmole) of triethylamine in 5 ml of tetrahydrofuran. The reaction mixture was stirred for 5 hours at −40° C., then stirred for 2 hours at −30° C. under a nitrogen atmosphere and then poured into a mixture of ethyl acetate (700 ml) and 5% aqueous phosphoric acid (1000 ml). The organic layer was washed with brine, dried over MgSO₄, filtered and condensed to a syrup. This material was purified by silica gel column chromatography [elution with methylene chloride-ethyl acetate (3:1 v/v)] to give 3.55 g (75% yield) of the title compound as a white amorphous solid.

NMR (CDCl₃) δ: 1.25 (3H, d, J=6.0 Hz), 3.05 (3H, s), 3.06–3.40 (5H, m), 4.05–4.40 (4H, m), 5.25 (1H, d, J=14.0 Hz), 5.50 (1H, d, J=14.0 Hz), 7.70 (2H, d, J=8.5 Hz) and 8.23 (2H, d, J=8.5 Hz); ir (KBr) γmax: 3400, 1770 and 1600 cm⁻¹. Anal. Calc'd for C₁₉H₂₂N₂O₉S₂: C, 46.90; H, 4.56; N, 5.76. Found: C, 46.52; H, 4.32; N, 5.91.

C. p-Nitrobenzyl 3-(2-iodoethylthio)-6α-[1-(R)-hydroxyethyl]-7-oxo-1-azabicyclo(3.2.0)hept-2-ene-2-carboxylate

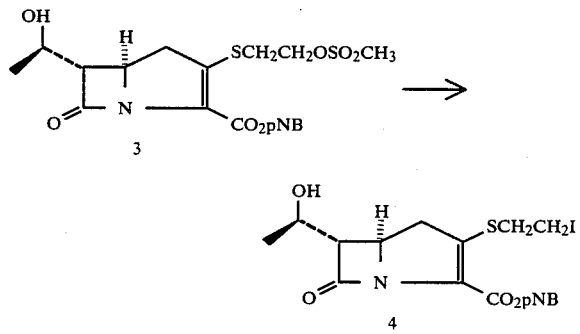

A solution of 350 mg (0.72 mmole) of intermediate 3 and 216 mg (1.4 mmole) of sodium iodide in 20 ml of acetone was heated at reflux for 4 hours. Evaporation of the acetone gave a white amorphous solid which was suspended in ether (10 ml)water (10 ml). Filtration of the white solid and vacuum drying produced 300 mg (80% yield) of the title compound 4 as a white amorphous powder.

NMR (DMSO-d6) δ: 1.18 (3H, d, J=6.0 Hz), 3.20–3.60 (7H, m), 3.80–4.25 (2H, m), 5.10 (1H, d, J=5.5 Hz), 5.25 (1H, d, J=12.0 Hz), 5.45 (1H, d, J=12.0 Hz), 7.70 (2H, d, J=8.5 Hz), and 8.27 (2H, d, J=8.5 Hz); ir (KBr) γmax: 3500, 1768 and 1700 cm⁻¹; Anal. Calc'd for C₁₈H₁₉N₂O₆I: C, 41.71; H, 3.70; N, 5.41; I, 24.48. Found: C, 42.10; H, 3.75; N, 5.97; I, 23.20.

D. 3-[2-(1-Pyridinium)ethylthio]-6α-[1-(R)-hydroxyethyl]-7-oxo-1-azabicyclo[3.2.0]hept-2-ene-2-carboxylate

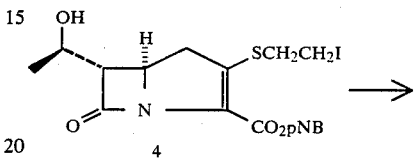

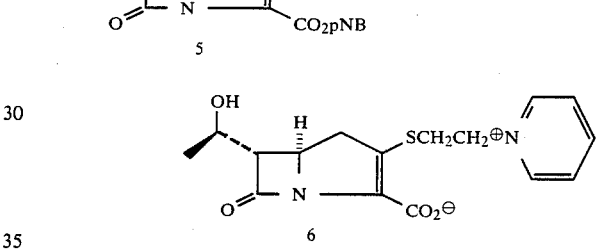

To a solution of 327 mg (0.63 mmole) of intermediate 4 in 20 ml of tetrahydrofuran there was added at 0° C. 100 mg (1.26 mmole) of pyridine followed by a solution of 139 mg (0.67 mmole) of silver perchlorate in 1 ml of tetrahydrofuran. The mixture was stirred for 1 hour at 0° C. and then for 2 hours at room temperature. The solvent was evaporated in vacuo affording compound 5 as a slightly yellow gum which was digested with 300 mg of CELITE to give an amorphous solid. IR (KBr) γmax: 3400, 1770, 1700 and 1100 cm⁻¹¹ Without any further purification, compound 5 was hydrogenated.

Thus, to a suspended mixture of compound 5 in 50 ml of ether and 50 ml of tetrahydrofuran there was added a solution of 126 mg (1.26 mmole) of potassium bicarbonate and 110 mg (0.63 mmole) of dibasic potassium phosphate in 50 ml of water. Then, 350 mg of 10% palladium on charcoal was added and the mixture was hydrogenated at 40 psi on the Parr shaker for 60 minutes. The mixture was then filtered and the catayst was washed with water (2×10 ml). The combined filtrate and washings were extracted with ether (2×100 ml) and then lyophilized to give a yellow powder. The crude yellow powder was purified on a C₁₈ BONDAPAK reverse phase column (8 g) (Waters Associates), eluting with water under 8 psi pressure. Each 15 ml fraction was assayed by high pressure liquid chromatography, and fractions having an ultraviolet absorption at λmax 300 nm were collected and lyophilized to give 40 mg (19% yield based on compound 4) of the title product 6 as a white amorphous solid.

NMR (D₂O) δ: 1.20 (3H, d, J=6.0 Hz), 2.90–3.70 (7H, m), 3.75–4.20 (2H, m) and 7.70–8.80 (5H, m); ir (KBr) γmax: 3400, 1760 and 1590 cm$^{-1}$; Anal. Calc'd for $C_{16}H_{18}N_2O_4S \cdot 2H_2O$: C, 51.89; H, 5.40; N, 7.56. Found: C, 49.91; H, 5.08; N, 7.11. UV λ$_{max}$ (CH$_3$CH$_2$OH) 296 nm (ε=7696).

EXAMPLE 2

Preparation of 3-[2-(1-Pyridinium)propylthio]-6α-[1-(R)-hydroxyethyl]-7-oxo-1-azabicyclo(3.2.0)hept-2-ene-2-carboxylate

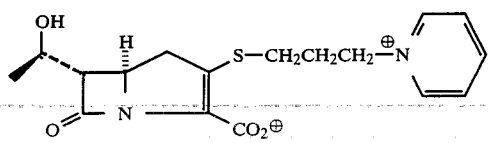

A. p-Nitrobenzyl 3-(2-hydroxypropylthio)-6α-[1-(R)-hydroxyethyl]-7-oxo-1-azabicyclo(3.2.0)-hept-2-ene-2-carboxylate

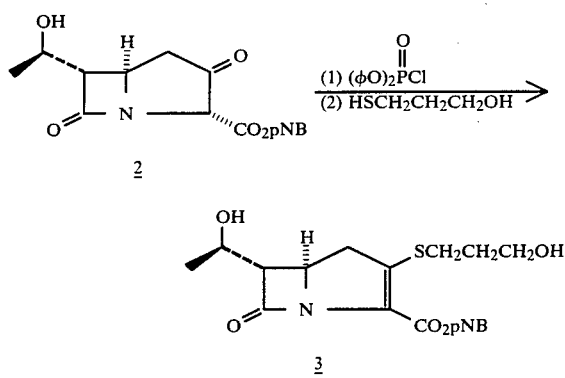

A solution of 926 mg (2.66 mmol) of p-nitrobenzyl 6[1-(R)-hydroxyethyl]-3,7-dioxo-1-azabicyclo(3.2.0)-hept-2-ene-2-carboxylate (2) in 15 ml of acetonitrile was cooled to −10° under a nitrogen atmosphere. A solution of 349 mg (2.7 mmol) of diisopropylethylamine in 1 ml of acetonitrile was added followed by a dropwise addition of 725 mg (2.0 mmol) of diphenylchlorophosphate in 0.7 ml of acetonitrile over a period of 2 minutes. The resulting solution was stirred at −10° for 15 minutes to provide p-nitrobenzyl-3-(diphenylphosphoryloxy)-6α-[1-(R)-hydroxyethyl]-7-oxo-1-azabicyclo[3.2.0]hept-2-ene-2-carboxylate. To this solution was added a solution of 326 mg (2.8 mmol) of diisopropylethylamine in 1 ml of acetonitrile followed by a solution of 273 mg (3.0 mmol) of 3-mercaptopropanol in 0.5 ml of acetonitrile. The reaction was stirred for five hours at room temperature and then overnight at 5°. Reaction was diluted with 100 ml of ethylacetate and washed with 100 ml of water and then brine. Condensation of dried (MgSO$_4$) solvent to about 5 ml of volume produced white crystals which were washed with ether to give 830 mg (74%) of the title compound (3) as white crystals; m.p. 142°–144° C.

NMR (DMSO-d$_6$) δ: 1.20 (3H, d, J=6.0 Hz) 1.5–2.0(2H, m), 2.8–3.6(7H, m), 4.60(1H, t, J=5.0 and 5.0 Hz), 5.1(1H, d, J=5.0 Hz), 5.25(1H, d, J=14.0 Hz), 5.50(1H, d, J=14.0 Hz) 7.70(2H, d, J=8.5 Hz) and 8.23(2H, d, J=8.5 Hz); ir (kBr) γmax: 3400, 1770, and 1600 cm$^{-1}$.

Anal. Calc'd for $C_{19}H_{22}N_2O_7S \cdot \frac{1}{2}H_2O$: C, 52.90; H, 5.33; N, 6.49; S, 7.42. Found: C, 53.10; H, 5.08; N, 6.61; S, 7.65.

B. p-Nitrobenzyl 3-(2-iodopropylthio)-6α-[1-(R)-hydroxyethyl]-7-oxo-1-azabicyclo(3.2.0)hept-2-ene-2-carboxylate

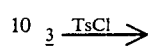

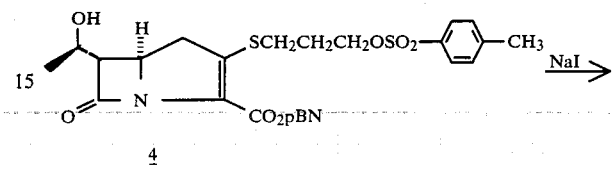

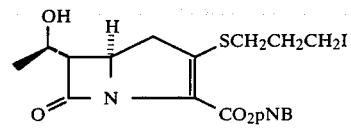

To a solution of 810 mg (1.91 mmol) of 3 in 20 ml of dry tetrahydrofuran was added 400 mg (2.10 mmol) of p-toluenesulfonylchloride followed by 268 mg (2.20 mmol) of dimethylamino pyridine and the mixture was stirred for two hours at room temperature under a nitrogen atmosphere. Reaction mixture was then poured into ethylacetate-ice water. The organic layer was washed with 40% H$_3$PO$_4$ and then dried over MgSO$_4$. Evaporation of dried solvents gave the tosylate 4 as a yellow oil which was converted into the iodo compound 5 without any further purification. The crude 4 was dissolved in 30 ml of acetone, 1.5 g (10 mmol) of sodium iodide was added and the mixture was stirred sixteen hours at room temperature. Reaction mixture was poured into ethylacetate-water. Evaporation of dried (MgSO$_4$) solvent gave a yellow syrup which was purified by silica gel column chromatography [elution with methylene chloride-ethylacetate (9:1 v/v) to give 142 mg (18.5% yield) of the title compound as a white amorphous powder.

NMR (acetone-d$_6$) δ: 1.25(3H, d, J=6.0 Hz), 2.7–3.5(7H, m), 4.0–4.4(2H, m), 5.30(1H, d, J=14.0 Hz), 5.65(1H, d, J=14.0 Hz), 7.80(2H, d, J=8.5 Hz), 8.30(2H, d, J=8.5 Hz); ir (KBr) γmax: 3500, 1770 and 1600 cm$^{-1}$.

C. 3-[2-(1-Pyridinium)propylthio]-6α-[1-(R)-hydroxyethyl]-7-oxo-1-azabicyclo(3.2.0)-hept-2-ene-2-carboxylate

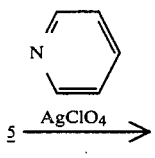

45
-continued

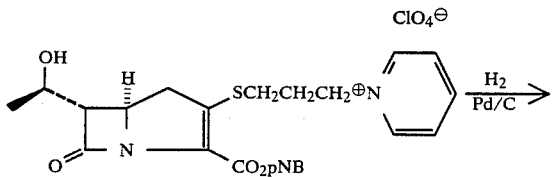

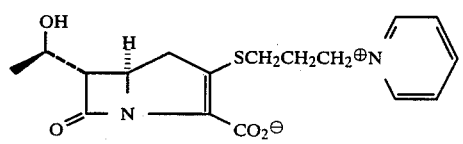

To a solution of 140 mg (0.3 mmol) of the iodo compound 5 in 5 ml of dry tetrahydrofuran was added 50 mg (0.6 mmol) of pyridine followed by a solution of 100 mg (0.5 mmol) of silver perchlorate in 1 ml of tetrahydrofuran. The mixture was stirred for two hours at room temperature and then the solvent was evaporated in vacuo affording compound 6 as a slightly yellow gum.

IR (KBr) Γmax: 3400, 1770, 1600 and 1100 cm$^{-1}$. Without any further purification, compound 6 was hydrogenated.

Thus, to a suspended mixture of compound 6 in 20 ml of ether and 20 ml of tetrahydrofuran there was added a solution of 30 mg (0.3 mmol) of potassium bicarbonate and 52 mg (0.3 mmol) of dibasic potassium phosphate in 20 ml of water. Then, 100 mg of 10% palladium on charcoal was added and the mixture was hydrogenated at 40 psi in the Par shaker for sixty minutes. The mixture was then filtered and the catalyst was washed with water (2×5 ml). The combined filtrate and washing were extracted with ether (2×5 ml) and then lyophilized to give yellow solids. The crude material was purified on a C$_{18}$ BONDAPAK reverse phase column (8 g) (Waters Associates), eluting with water under 8 psi pressure. Each 10 ml fraction was assayed by high pressure liquid chromatography, and fractions having an ultraviolet absorption at λmax 300 nm were collected and lyophilized to give 8 mg of the title compound as a slightly yellow glassy powder.

NMR (D$_2$O) δ: 1.25(3H, d, J=6.5 Hz), 1.5–1.8(2H, m), 2.2–3.70(7H, m), 4.0–4.3(2H, m), 7.9–8.9(m, 5H); ir (KBr) γmax: 3400, 1760 and 1590 cm$^{-1}$. UV λmax (H$_2$O) 294 nm (E=6,082), 265 nm (E=6,317).

EXAMPLE 3

Preparation of
3-[2-(1-Pyridinium)ethylthio]-6α-[1(R)-hydroxyethyl]-7-oxo-1-azabicyclo(3.2.0)hept-2-ene-2-carboxylate (Preferred process)

A. 2-(triphenylmethylthio)ethanol

Method A

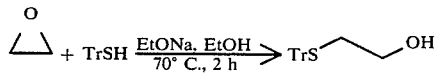

To a suspension of triphenylmethyl mercaptan (2.74 g, 0.010 mol) in ethanol (10 mL) was added an aqueous solution of sodium hydroxide (0.25 mL, 4N, 1.0 mmol).

46

The mixture was stirred for 5 min, treated with ethylene oxide (0.75 mL, 0.015 mol), stirred for 15 min and heated at 70° C. for 2 h. After cooling to 35° C., the reaction mixture was neutralized with rexyn-102 H$^+$ and filtered. The filtrate was concentrated to a syrup which crystallized on standing. Trituration of the solid in hexane afforded after filtration 3.20 g (100%), mp 102°-8° C. (lit. (1) mp 114°-115° C.). An analytical sample was obtained after a recrystallization in dichloromethanehexane mp 108°-10° C.; ir (KBr) ν$_{max}$: 3340 (br OH), 1590 (aromatic), 1483, 1445, 1439, 1182, 1060, 1035, 1010, 751, 638, 695 cm$^{-1}$, $^1$Hmr (CDCl$_3$) δ: 1.61 (1H, s, OH), 2.48 (2H, t, J=6.1 Hz, H-2), 3.39 (2H, t, J=6.1 Hz, H-1), 6.7–7.7 (15H, m, phenyl).

$^1$C. C. Culvenor, W. Davies and W. E. Savige, J. Chem. Soc., 4480 (1952)

Method B

To a solution of sodium ethoxide in ethanol [prepared from sodium hydroxide (3.4 g, 0.085 mol) in ethanol (35 mL)] was added 2 mercaptoethanol (5.6 mL, 0.080 mol) and triphenylmethyl chloride (23.4 g, 0.084 mol) at such a rate that the temperature was kept at 45°-60° C. The reaction mixture was refluxed for 1.5 h, cooled to 30° C. and filtered. The solid was washed with ether (3×30 mL). The filtrate was concentrated to a syrup which was dissolved in ether (150 mL). The organic solution was washed with water, diluted acetic acid and water, dried (MgSO$_4$-MgO) and concentrated under reduced pressure to a syrup which was solubilized in dichloromethane-hexane mixture (1:1). Filtration of the crystals afforded 5.7 g (22%), mp 109°-10° C. (lit. (1) mp 114°-115° C.) of the title compound. The filtrate was purified by chromatography (silicagel 60, 70–230 mesh, 240 g). The appropriate fractions were combined and concentrated to a syrup from which 4.61 (18%) mp 107°-9° C. were obtained by crystallization (dichloromethane-hexane) for an overall yield of 40%. The analytical data were identical to those reported for the compound prepared in the method A.

B. 2-(triphenylmethylthio)ethyl methanesulfonate

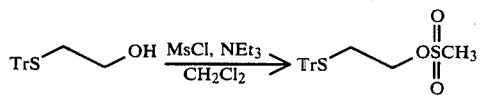

To a solution of 2-(triphenylmethylthio)ethanol (2.66 g, 8.30 mmol) in cold (0° C.) dichloromethane (39 mL) kept under a nitrogen atmosphere was added methanesulfonyl chloride (0.704 mL, 9.10 mmol); the resulting mixture was treated dropwise (15 min) with triethylamine (1.34 mL, 9.6 mmol). After stirring for 15 min, the cooling bath was removed and the reaction mixture was stirred for 7 h then washed successively with water (10 mL), 0.5N citric acid (10 mL), water (10 mL), saturated sodium bicarbonate and water. The organic extracts were dried (MgSO$_4$-MgO) and concentrated under reduced pressure to a thick syrup which crystallized on standing. Trituration of the crystals in ether afforded white solid 2.1 g (63%) mp 95°-8° C.; ir (KBr) ν$_{max}$: 1580, 1565 (phenyl), 1350, 1175, 1165 cm$^{-1}$ (sulfonate); $^1$Hmr (CDCl$_3$): 251 (2H, t, J=6.6 Hz, CH$_2$S), 3.07 (3H, s, CH$_3$SO$_3$), 3.87 (2H, t, J=6.6 Hz, CH$_2$O), 7.34 (15H, m, phenyl).

C. 1-(2-triphenylmethylthioethyl)pyridinium methanesulfonate

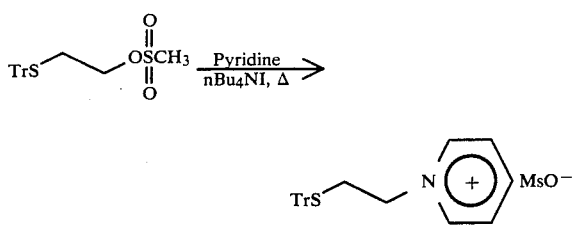

A mixture of 2-(triphenylmethylthio)ethyl methanesulfonate (0.598 g, 1.50 mmol), tetra-n-butylammonium iodide (0.020 g) and pyridine (1.2 mL, 15.0 mmol) was heated at 90° C. under a nitrogen atmosphere for 3 h. After cooling to 25° C., the pyridine was evaporated under reduced pressure to a white solid which was triturated in ether and filtered 0.66 g, (92%), mp 135°–50° C. dec. ir (KBr) $\nu_{max}$: 1628 (pyridinium), 1590, 1575 (phenyl), 1190 cm$^{-1}$ (sulfonate), $^1$Hmr (DMSO-d$_6$)δ: 2.31 (3H, s, CH$_3$SO$_3$$^-$), 2.82 (2H, m, CH$_2$S), 4.40 (2H, m, CH$_2$N$^+$), 7.28 (15H, m, phenyl), 8.12 (2H, m, Hm of pyridinium), 8.59 (1H, m, Hp of pyridinium), 8.84–8.85 (2H, dd, J=1.3 Hz, J=6.7 Hz, Ho of pyridinium). Anal. calcd. for C$_{27}$H$_{37}$NO$_3$S$_2$.H$_2$O: C 65.43, H 5.90, N 2.83, S 12.94; found: C 65.77, H 5.81, N 3.25, S 12.55.

D. 1-(2-mercaptoethyl)pyridinium methanesulfonate

Method A

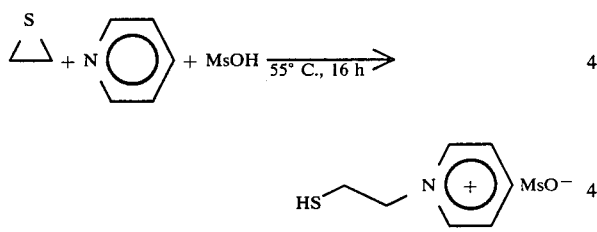

To a suspension of pyridinium methanesulfonate in pyridine prepared by the dropwise addition of methanesulfonic acid (1.95 mL, 0.03 mol) to pyridine (8.0 mL, 0.099 mol) with cooling, was added ethylene sulfide (1.96 mL, 0.033 mol). The resulting mixture was stirred at 55° C. for 16 h and concentrated under reduced pressure to a thick syrup which was mixed with few mL of water. The solution was poured on top of a column (40×16 cm) of μ-bondapak C-18 which was eluted with water. Lyophylization of the appropriate fractions gave a colorless syrup 6.5 g (91%), ir (film) $\nu_{max}$: 2300–2600 (br, SH), 1635 (pyridinium), 1490, 1200 (sulfonate), 1068, 1060, 1045, 791, 780 cm$^{-1}$, $^1$Hmr (DMSO-d$_6$)δ: 2.32 (3H, s, CH$_3$SO$_3$$^-$), 2.61, 2.70, 2.73, 2.82 (1H, B part of A$_2$B system, SH), 3.07 (2H, m [with D$_2$O, 3.08 (2H, t, J=6.5 Hz)], CH$_2$S), 4.76 (2H, t, J=6.5 Hz, CH$_2$N$^+$), 8.19 (2H, m, Hm of pyridinium), 8.6 (1H, m, Ho of pyridinium), 9.08 (2H, dd, J=6.8 Hz, J=1.4 Hz, Ho of pyridinium), uv (H$_2$O) $\nu_{max}$: 206 (ε5230), 258 (ε3760) mμ.

METHOD B

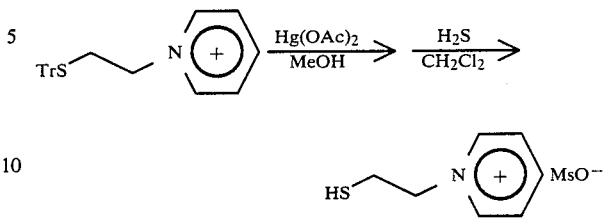

A solution of 1-(2-triphenylmethylthioethyl)-pyridinium methanesulfonate (0.477 g, 1.0 mmol) in methanol (25 mL) was treated with mercuric acetate (0.335 g, 1.05 mmol) and stirred at 25° C. for 2 h. The mixture was concentrated under reduced pressure and the residue was triturated in ether (30 mL) to give a white solid after filtration. A suspension of it in dichloromethane (25 mL) was treated at 25° C. with gaseous hydrogen sulfide for 1.75 h and filtered. The filtrate was concentrated under reduced pressure and the residue was diluted in water and applied on top of a column (1.5×6.0 cm) of μ-bondapak C-18. Elution of the column with a mixture of 15% acetonitrile and 85% water afforded after lyophylization of the appropriate fractions a colorless thick syrup 0.179 g (76%). The analytical data were identical to those reported for the title compound prepared in the method A.

E. 1-(2-mercaptoethyl)pyridinium chloride

METHOD A:

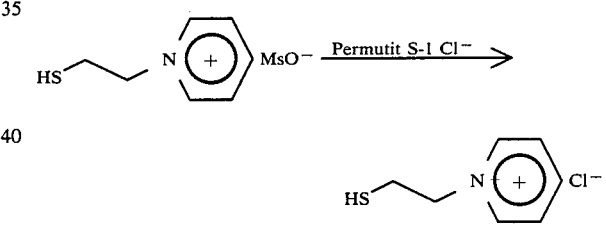

An aqueous solution of crude 1-(2-mercaptoethyl)-pyridinium methanesulfonate (9.4 g, 0.04 mol) was poured on top of column (2.5×41 cm) of permutit S-1 Cl$^-$. The column was eluted with water at a rate of 0.5 mL per min and the appropriate fractions were combined and lyophylized giving a yellowish syrup 7.0 g (100%) which was used as it was for the next step, $^1$Hmr (D$_2$O)δ: 3.22 (2H, m, CH$_2$S), 4.88 (m, CH$_2$N$^+$), 8.18 (2H, m, Hm of pyridinium), 8.7 (1H, m, Hp of pyridinium), 9.0 ppm (2H, m, Ho of pyridinium).

METHOD B

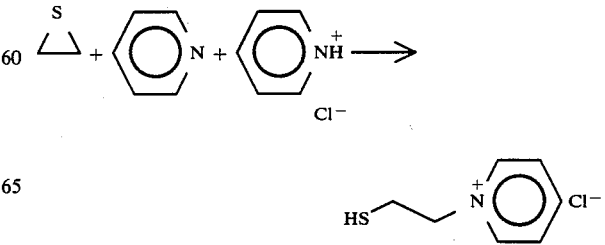

To a precooled (ice bath) pyridine (5.6 mL, 70 mmol) was added pyridine hydrochloride (4.05 g, 35 mmol) and ethylene sulfide (2.1 mL, 35 mmol). The mixture was heated at 65° C. and stirred for 75 min to give a two phases system. The lighter phase was removed. The remaining oil was washed with ether (5×10 mL) and pumped under high vacuum to give the title compound (90–100%) which was used as such for the next step.

F. Paranitrobenzyl 3-[2-(1-pyridinium)ethylthio]-6α-[1-(R)-hydroxyethyl]-7-oxo-1-azabicyclo(3.2.0)hept-2-ene-2-carboxylate chloride

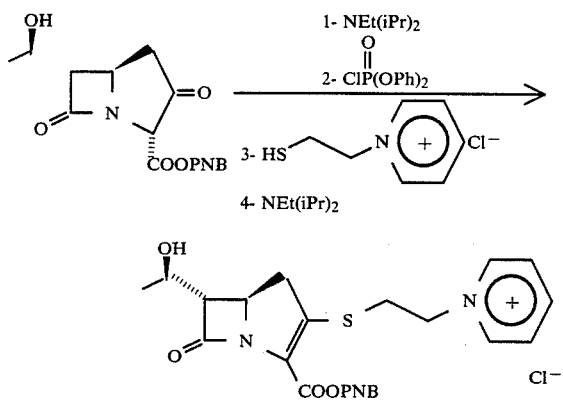

A solution of p-nitrobenzyl 6α-[1-(R)-hydroxyethyl]-3,7-dioxo-1-azabicyclo(3.2.0)hept-2-ene-2-carboxylate (6.09 g, 17.5 mmol) in acetonitrile (20 mL) was cooled to +5° C. under a nitrogen atmosphere and treated successively with diisopropylethylamine (3.65 mL, 21.0 mmol) and diphenyl chlorophosphate (4.34 mL, 21.0 mmol). The resulting mixture was stirred for 30 min at 5° C., cooled at −5° C. and treated successively with a solution of crude 1-(2-mercaptoethyl)pyridinium chloride (4.3 g, 24 mmol) in N,N-dimethylformamide (1.0 mL) and dropwise with diisopropylethylamine (3.65 mL, 21.0 mmol). The reaction mixture was stirred at 0° C. for 1 h, cooled to −30° C. and stirred for 15 min. more. The solid was filtered off and washed with cold (−30° C.) acetonitrile 5.77 g (65%), ir (nujol) $\nu_{max}$: 3300 (OH), 1775 (C=O of β-lactam), 1690 (C=O of PNB ester), 1630 (pyridinium), 1605 (phenyl of PNB ester), 1515 (NO$_2$), 1335 cm$^{-1}$ (NO$_2$), $^1$Hmr (DMSO-d$_6$)δ: 1.17 (3H, d, J=6.1 Hz, CH$_3$CHOH), 3.2–3.75 (5H, H-4, H-6, CH$_2$S), 3.75–4.5 (2H, H-5, CH$_3$CHOH), 4.92 (2H, brt, J=6.5 Hz, CH$_2$N$^+$), 5.18 (1H, d, J=4.9 Hz,OH), 5.37 (center of ABq, J$_{a,b}$=14.2 Hz, CH$_2$ of PNB), 7.69 (2H, d, J=8.7 Hz, Ho of PNB), 8.24 (d, J=8.7 Hz, Hm of PNB, 8.0–8.4 (4H, Hm of PNB, Hm of pyridinium), 8.66 (1H, m, Hp of pyridinium), 9.17 (2H, brd, J=5.5 Hz, Ho of pyridinium). The filtrate and washing were combined and diluted with ether (150 mL). The supernatant was decanted and the gum was dissolved in water (40 mL) containing enough acetonitrile to have a solution which was poured on top of a column (3×10 cm) of μ-bondapak C-18. The column was eluted with 10% acetonitrile-90% water (150 mL) and 50% acetonitrile-50% water (100 mL) mixtures. The appropriate fractions were combined and lyophylized after the acetonitrile has been removed under vacuum giving a yellowish powder. An NMR of it showed the presence of the title compound mixed with some p-nitrobenzyl 3-[2-(1-pyridinium)ethylthio]-6α-[1-(R)-hydroxyethyl]-7-oxo-1-azabicyclo(3.2.0)hept-2-ene-2-carboxylate diphenylphosphate (2:1). The powder was dissolved in water (minimum amount) and passed through the column (1.5×21 cm) of permutit S-1Cl$^-$ with water. Lyophilization of the appropriate fractions gave 1.8 g (20%) of the title compound.

G. Paranitrobenzyl 3-[2-(1-pyridinium)ethylthio]-6α-[1-(R)-hydroxyethyl]-7-oxo-1-azabicyclo(3.2.0) hept-2-ene-2-carboxylate diphenylphosphate

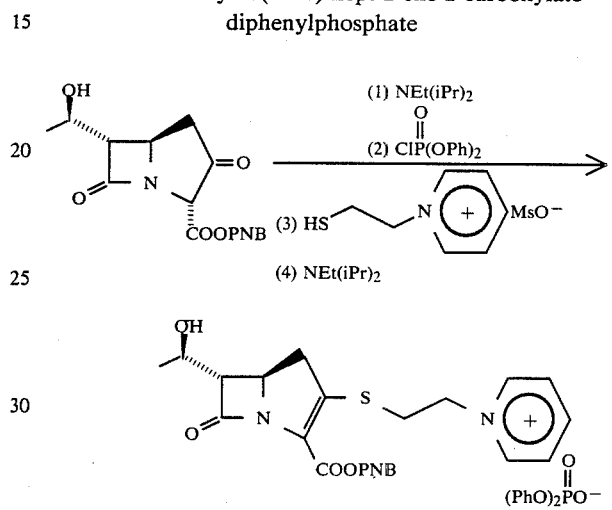

A solution of p-nitrobenzyl 6α-[1-(R)-hydroxyethyl]-3,7-dioxo-1-azabicyclo(3.2.0)hept-2-ene-2-carboxylate (0.174 g, 0.50 mmol) in acetonitrile (2 mL) was cooled to 0° C. under a nitrogen atmosphere and treated successively with diisopropylethylamine (0.105 mL, 0.60 mmol) and diphenyl chlorophosphate (0.124 mL, 0.60 mmol). The resulting solution was stirred for 30 min at 0° C. and treated successively with a solution of 1-(2-mercaptoethyl)pyridinium methanesulfonate (0.170 g, 0.72 mmol) in acetonitrile (0.6 mL) and diisopropylethylamine (0.105 mL, 0.60 mmol). The reaction mixture was stirred at 0° C. for 15 min, diluted with cold (0° C.) water (7 mL) and poured on top of a column (1.5×6.4 cm) of μ-bondapak C-18. The column was eluted with a mixture of acetonitrile (25%–50%) in water (75%–50%). The appropriate fractions were combined and lyophylized after the acetonitrile has been removed under vacuum giving a yellowish powder 0.33 g (92%), ir (KBr) $\nu_{max}$: 3600–3000 (OH), 1765 (C=O of β-lactam), 1690 (C=O of PNB ester), 1625 (pyridinium), 1585 (phenyl), 1510 (NO$_2$), 1330 (NO$_2$), 885 cm$^{-1}$ (NO$_2$), $^1$Hmr (DMSO-d$_6$)δ: 1.16 (3H, d, J=6.2 Hz, CH$_3$)CHOH), 4.87 (2H, brt, J=6.6 Hz, CH$_2$S), 5.37 (center of ABq, J$_{a,b}$=14.3 Hz, CH$_2$ of PNB), 6.7–7.5 (phenyl), 7.68 (d, J=8.8 Hz, Ho of PNB), 8.23 (d, J=8.8 Hz, Hm of PNB), 8.0–8.3 (m, Hm of pyridinium), 8.4–8.8 (1H, Hp of pyridinium), 9.09 (2H, dd, J=6.7 Hz, J=1.3 Hz, Ho of pyridinium).

H. 3-[2-(1-pyridinium)ethylthio]-6α-[1-(R)-hydroxyethyl]-7-oxo-1-azabicyclo(3.2.0)hept-2-ene-2-carboxylate

Method A

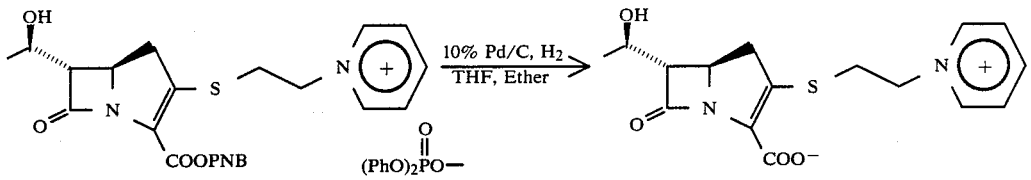

To a solution of p-nitrobenzyl 3-[2-(1-pyridinium)ethylthio]-6α-[1-(R)-hydroxyethyl]-7-oxo-1-azabicyclo(3.2.0)hept-2-ene-carboxylate diphenylphosphate (0.16 g, 0.22 mmol) in wet tetrahydrofuran (10 mL) was added ether (10 mL), potassium phosphate monobasic-sodium hydroxide buffer pH 7.4 (16 mL, 0.05 M) and 10% palladium on charcoal (0.16 g). The resulting mixture was hydrogenated under 40 psi for 1 h at 25° C. The two phases were separated and the organic phase was extracted with water (2×3 mL). The aqueous solution were combined, washed with ether (2×10 mL) and poured on top of a column (1.5×6.2 cm) of μ-bondapak C-18 after the traces of organic solvents have been removed under vacuum. Elution of the column with water gave after lyophylization of the appropriate fractions a yellowish powder 0.062 g (84%), ir (KBr) $\nu_{max}$: 3700–3000 (OH), 1755 (C-O of β-lactam), 1630 (pyridinium), 1590 cm$^{-1}$ (carboxylate), $^1$Hmr (D$_2$O): 1.22 (3H, d, J=6.4 Hz, CH$_3$CHOH), 2.92 (d, J=9.1 Hz, H-4), 2.97 (d, J=9.1 Hz, H-4), 3.20 (dd, J=2.5 Hz, J=6.1 Hz, H-6), 3.44 (t, J=6.0 Hz, CH$_2$S), 3.93 (dd, J=9.1 Hz, J=2.5 Hz, H-5), 4.82 (t, J=6.0 Hz, CH$_2$N$^+$), 8.04 (m, Hm of pyridinium), 8.5 (m, Hp of pyridinium), 8.82 (dd, J=3.2 Hz, J=1.1 Hz, Ho pyridinium), uv (H$_2$O) λ$_{max}$: 259 (ε5800), 296 (ε7030) mμ, t$_½$=13.5 h (measured at a concentration of 10$^{-4}$M in phosphate buffer pH 7.4 at 36.8° C.).

Method B

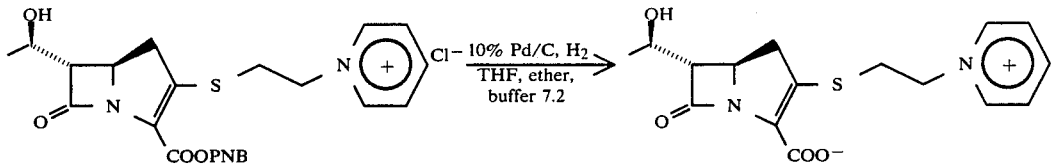

To a solution of p-nitrobenzyl 3-[2-(1-pyridinium)ethylthio]-6α-[1-(R)-hydroxyethyl]-7-oxo-1-azabicyclo(3.2.0) hept-2-ene-2-carboxylate chloride (5.77 g, 11.4 mmol) in potassium phosphate monobasicsodium hydroxide buffer (170 mL, 0.2M, pH 7.22) was added tetrahydrofuran (30 mL), ether (30 mL) and 10% palladium on charcoal (5.7 g). The resulting mixture was hydrogenated at 22° C. under 40 psi for 1 h and filtered on a Celite pad. The pad was washed with water (2×15 mL). The filtrate and washings were combined and diluted with ether (100 mL). The aqueous phase was separated, washed with ether (3×100 mL) and poured on top of a column (4.5×20 cm) of μ-bondapak C-18 after the organic solvents have been removed under vacuum. Elution of the column with water followed by a mixture of 1% acetonitrile in water gave after lyophylization of the appropriate fractions 2.48 g (65% of the title compound as a yellowish powder. The analytical data were identical to those reported for the compound prepared in the method A.

EXAMPLE 4

Preparation of 3-[2-(1-(3,5-dimethylpyridinium)ethylthio]-6α-[1-(R)-hydroxyethyl]-7-oxo-1-azabicyclo(3.2.0.)hept-2-ene-2-carboxylate

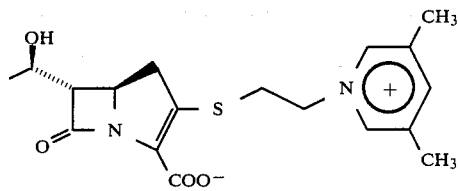

A. 1-(2-mercaptoethyl)-3,5-dimethylpyridinium methanesulfonate

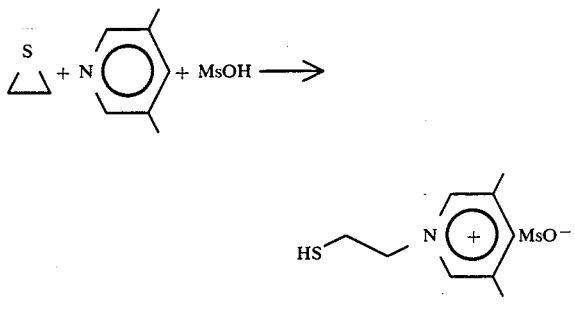

To a suspension of 3,5-lutidinium methanesulfonate in 3,5-lutidine prepared by the addition of methanesulfonic acid (0.65 mL, 0.010 mol) to cold 3,5-lutidine (2.51 mL, 0.022 mol) was added ethylene sulfide (0.655 mL, 0.011 mol). The resulting mixture was stirred under a nitrogen atmosphere at 55° C. for 24 h, cooled to 23° C. and diluted with water (5 mL) and ether (5 mL). The organic layer was separated and the aqueous solution was washed with ether (6×4 mL). The traces of ether were removed under vacuum and the solution was applied on top of a column (2.5×6.0 cm) of μ-bondapak C-18. The column was eluted with water and lyophilization of the appropriate fractions gave a colourless syrup 2.4 g (91%); ir (film) $\nu_{max}$: 2520 (SH), 1628 (pyridinium), 1600, 1495, 1325, 1305, 1283, 1200 (sulfonate), 1040, 938, 765, 680 cm$^{-1}$; $^1$Hmr (DMSO d$_6$)δ: 2.31 (3H, s, CH$_3$SO$_3^-$), 2.47 (6H, s, CH$_3$ on pyridinium), 2.57, 2.66, 2.69, 2.78 (1H, B part of A$_2$B system, SH), 3.06 (2H, m[with D$_2$O added (2H, t, J=6.5 Hz)], CH$_2$S), 4.65 (2H, t, J=6.5 Hz, CH$_2$N$^+$), 8.34 (1H, s, Hp of pyridinium), 8.79 (2H, s, Ho of pyridinium); uv (H$_2$O) λ$_{max}$: 271 (ε4860) mμ. Anal. calcd. for C$_{10}$H$_{17}$NO$_3$S$_2$.0.5H$_2$O: C 44.09, H 6.66, N 5.14, S 23.54; found: C 44.26, H 6.49, N 5.17, S 24.18.

B. Paranitrobenzyl 3-[2-(1-(3,5-dimethylpyridinium)ethylthio]-6α-[1-(R)-hydroxyethyl]-7-oxo-azabicyclo(3.2.0)hept-2-ene-2-carboxylate diphenylphosphate

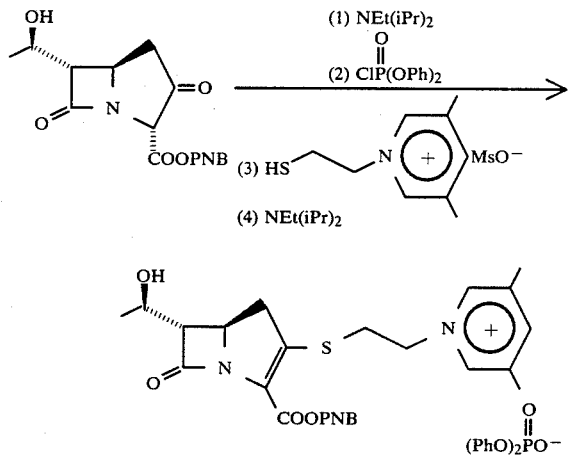

To a cold (0° C.) solution of p-nitrobenzyl 6α-(1-(R)-hydroxyethyl)-3,7-dioxo-1-azabicyclo(3.2.0)hept-2-ene-2-carboxylate (0.523 g, 1.50 mmol) in acetonitrile (6.0 mL) kept under a nitrogen atmosphere was added diisopropylethylamine (0.314 mL, 1.8 mmol) followed by diphenyl chlorophosphate (0.373, 1.8 mmol). The reaction mixture was stirred for 30 min and treated with a solution of 1-(2-mercaptoethyl)-3,5-dimethylpyridinium methanesulfonate (0.493 g, 1.87 mmol) in acetonitrile (1.9 mL) followed by diisopropylethylamine (0.314 mL, 1.8 mmol). The reaction mixture was stirred for 0° C. for 1 h diluted with cold (0° C.) water (26 mL) and poured on top of a column (7.0×3.5 cm) of μ-bondapak C-18. Elution of the column with 25–50% acetonitrile-75–50% water mixture gave after lyophilization of the appropriate fractions 1.01 g (90%) of the title compound as yellowish powder, ir (KBr) ν$_{max}$: 3700–3100 (OH), 1778 (C=O of β-lactam), 1700 (C=O of PNB ester), 1635 (pyridinium), 1595 (phenyl), 1521 (NO$_2$), 1335 (NO$_2$), 895 cm$^{-1}$ (NO$_2$), $^1$Hmr (DMSO d$_6$)δ: 1.16 (3H, d, J=6.1 Hz, CH$_3$CHOH), 2.43 (s, CH$_3$ on pyridinium), 4.75 (2H, m, CH$_2$N$^+$), 5.38 (center of ABq, J$_{a,b}$=14.3 Hz, CH$_2$ of PNB), 6.6–7.5 (10H, m, phenyl), 7.70 (2H, d, J=8.7 Hz, Ho of PNB), 8.0–8.5 (3H, m, Hp of pyridinium, Hm of PNB), 8.82 (2H, s, Ho of pyridinium), uv (H$_2$O) ν$_{max}$: 270 (ε11570), 306 (ε7343) mμ. Anal. calcd. for C$_{37}$H$_{38}$N$_3$O$_{10}$SP.H$_2$O: C 58.03, H 5.26, N 5.48, S 4.18; found: C 57.98, H 5.05, N 5.22, S 4.34.

C. 3-[2-(1-(3,5-dimethylpyridinium)ethylthio]-6α-[1-(R)-hydroxyethyl]-7-oxo-1-azabicyclo(3.2.0)hept-2-ene-2-carboxylate

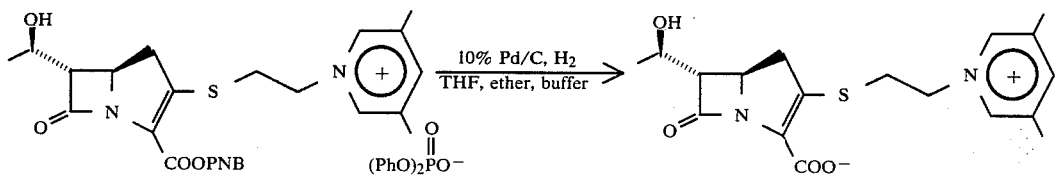

To a solution of p-nitrobenzyl 3-[2-(1-(3,5-dimethylpyridinium))ethylthio]-6α-[1-(R)-hydroxyethyl]-7-oxo-1-azabicyclo(3.2.0)hept-2-ene-2-carboxylate diphenylphosphate (0.600 g, 0.80 mmol) in wet tetrahydrofuran (36 mL) was added ether (36 mL), potassium phosphate monobasicsodium hydroxide buffer (0.05M, pH 7.4, 44 mL) and 10% palladium on charcoal (0.60 g). The resulting mixture was hydrogenated under 40 psi at 23° C. for 1.25 h. The organic layer was separated and extracted with buffer (2×5 mL). Water layers were combined, filtered through a Celite pad, washed with ether (40 mL), pumped to eliminate traces of organic solvents and poured on top of a column (2.5×10.0 cm) of μ-bondapak C-18. Elution of the column with water and lyophilization of the appropriate fractions gave the title compound 0.186 g (64%) as a yellowish powder, ir (KBr) ν$_{max}$: 3700–3100 (OH), 1760 (C=O of β-lactam), 1595 cm$^{-1}$ (carboxylate), $^1$Hmr (D$_2$O)δ: 1.21 (3H, d, J=6.3 Hz, CH$_3$CHOH), 2.45 (6H, s, CH$_3$ on pyridinium), 2.81 (d, J=9.2 Hz, H-4), 2.96 (d, J=9.2 Hz, H-4), 3.22 (dd, J=2.6 Hz, J=6.2 Hz, H-6), 3.40 (t, J=6.2 Hz, CH$_2$S), 3.84 (dd, J=9.2 Hz, J=2.6 Hz, H-5), 4.15 (m, CH$_3$CHOH), 4.71 (t, J=6.2 Hz, CH$_2$N$^+$), 8.21 (1H, s, Hp of pyridinium), 8.46 (2H, s, Ho of pyridinium), uv (H$_2$O) λ$_{max}$: 279 (ε8345), 296 (ε7714) m, [α]$_D^{23}$+40.7 (c 0.53, H$_2$O), τ$_{\frac{1}{2}}$=16.9 h (measured at a concentration of 10$^{-4}$M in phosphate buffer pH 7.4 at 36.8° C.).

EXAMPLE 5

Preparation of (5R,6S)-3-[[2-(3-hydroxymethylpyridinio)ethyl]thio]-6-[(R)-1-hydroxyethyl]-7-oxo-1-azabicyclo[3.2.0]hept-2-ene-2-carboxylate

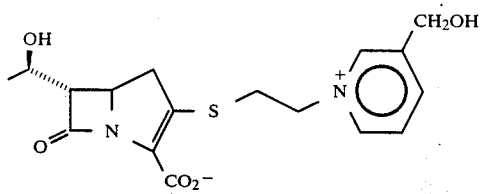

A. 3-Hydroxymethyl-1-(2-mercaptoethyl)pyridinium trifluoromethanesulfonate

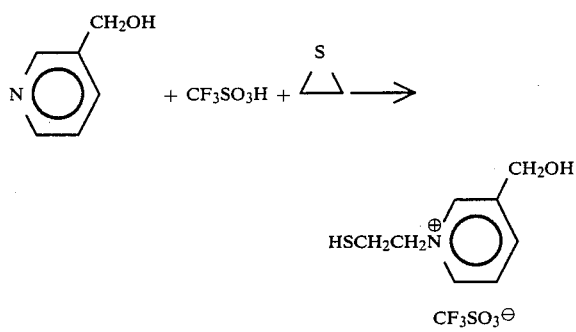

Trifluoromethanesulfonic acid (1.327 mL, 0.015 mol) was added dropwise to 3-pyridinemethanol (2.91 mL, 0.030 mol), followed by ethylene sulfide (0.89 mL, 0.015 mol). The resulting homogeneous mixture was heated (oil bath) at 50°–70° C. under $N_2$ for 20 h. The reaction mixture was then taken up in $H_2O$ (15 mL) and extracted with $CH_2Cl_2$ (5×5 mL). The aqueous phase was concentrated in vacuo and then applied to a $C_{18}$ reverse-phase column. Elution with $H_2O$ followed by evaporation of the relevant fractions gave a pale yellow oil. This material was rechromatographed to give a nearly colourless oil. After drying in vacuo ($P_2O_5$) this afforded the product (4.50 g, 94%) as a viscous oil. ir (film) $\nu_{max}$: 3450 (s, OH), 2560 (w, SH) cm$^{-1}$; $^1$Hmr (d$_6$-acetone)δ: 9.10–8.05 (m, 4H, aromatic), 5.01 (t, J=5.5 Hz, 2H, N-CH$_2$), 4.93 (s, 2H, —CH$_2$OH), 4.43 (br S, 1H, -OH), 3.43–3.18 (m, 2H, S-CH$_2$), 2.34–2.10 (m, 1H, SH).

B. p-Nitrobenzyl (5R,6S)-3-[2-(3-hydroxymethylpyridinio)ethyl thio]-6-[1-(R)-hydroxyethyl]-7-oxo-1-azabicyclo[3.2.0]-hept-2-ene-2-carboxylate diphenylphosphate

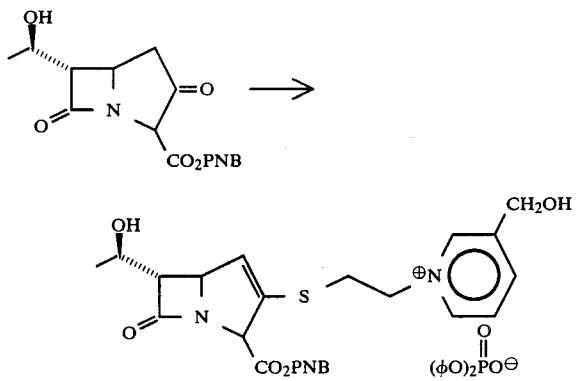

To a solution of p-nitrobenzyl (5R, 6S)-6-[1-(R)-hydroxyethyl]-3,7-dioxo-1-azabicyclo[3.2.0]heptane-2-carboxylate (0.174 g, 0.50 mmol) in 2 mL of dry acetonitrile was added diisopropylethylamine (0.096 mL, 0.55 mmol) at 0° C. under $N_2$. Diphenyl chlorophosphate (0.114 mL, 0.55 mmol) was then added dropwise and the reaction was stirred at 0° C. for 30 min. A solution of 3-hydroxymethyl-1-(2-mercaptoethyl)pyridinium trifluoromethanesulfonate (0.223 g, 0.70 mmol) in 0.50 mL of acetonitrile was then added, followed by diisopropylethylamine (0.122 mL, 0.70 mmol). After being kept at 0° C. for 30 min the reaction mixture was concentrated in vacuo and the residual yellow gum was taken up in $H_2O$ (enough acetonitrile was added to aid in dissolving the gum). This solution was applied to a $C_{18}$ reverse-phase column which was eluted with 15% acetonitrile-$H_2O$. Lyophilization of the relevant fractions afforded the product (0.305 g, 81%) as a beige-coloured solid. ir (KBr) $\nu_{max}$: 3420 (br, OH), 1775 (β-lactam CO), 1695 (—CO$_2$PNB) cm$^{-1}$; $^1$Hmr (D$_6$-acetone)δ: 9.44–7.72 (m, 8H, aromatic), 7.22–6.91 (m, 10H, diphenylphosphate), 5.53, 5.27 (ABq, J=14 Hz, 2H, benzylic), 5.04 (t,J=7.4 Hz, 2H, N-CH$_2$), 4.75 (s, 2H, CH$_2$OH), 4.5–3.1 (m, 8H), 1.21 (d, J=6.3 Hz, 3H, CHMe).

C. (5R,6S)-3-[2-(3-hydroxymethylpyridinio)ethyl thio]-6-[1-(R)-hydroxyethyl]-7-oxo-1-azabicyclo[3.2.0]-hept-2-ene-2-carboxylate

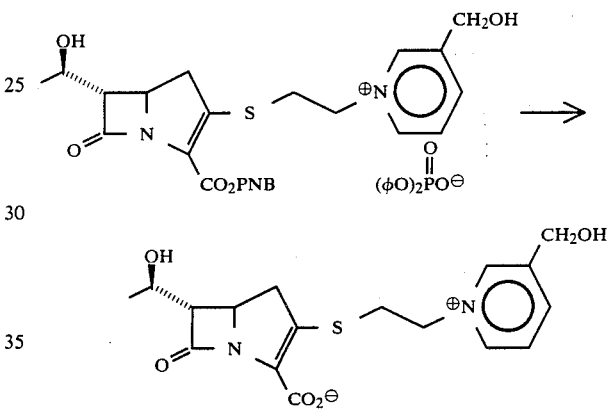

To a solution of p-nitrobenzyl (5R,6S)-3-[2-(3-hydroxymethylpyridinio)ethyl thio]-6-[1-(R)-hydroxyethyl]-7-oxo-1-azabicyclo[3.2.0]-hept-2-ene-2-carboxylate diphenylphosphate (0.145 g, 0.194 mmol) in 10 mL of THF containing 5 drops of $H_2O$, was added 6.0 mL of phosphate buffer (0.05M, pH 7.4), 0.145 g of 10% palladium-on-charcoal and 10 mL of ether. The mixture was hydrogenated (Parr) at 40 psi for 1 h and then filtered through a pad of Celite. The filter cake was washed with a little $H_2O$ and ether and the aqueous phase was separated and extracted with ether (3x). The aqueous solution was then cooled at 0° C. and the pH was adjusted to 7.0 with pH 7.4 buffer. After removing residual volatiles in vacuo the aqueous solution was applied to a $C_{18}$ reverse-phase column which was eluted with $H_2O$. Lyophilization of the relevant fractions gave the product (36 mg, 51%) as a light yellow solid. Further purification by reverse-phase hplc gave the pure product (31 mg, 41%) as a solid. ir (KBr) $\nu_{max}$: 3300 (br, OH), 1755 (β-lactam CO), 1590 (—CO$_2$$^-$) cm$^{-1}$; $^1$Hnmr (D$_2$O)δ: 8.78–7.94 (m, 4H, aromatic), 4.83 (t, J=6.0 Hz, 2H, N-CH$_2$), 4.83 (s, 2H, CH$_2$OH), 4.16 (d of q, J=J'=6.2 Hz, 1H, H-1'), 3.98 (d, of t, J=9.1 Hz, J'=2.6 Hz, 1H, H-5), 3.75–3.20 (m, 3H), 3.20–2.65 (m, 2H), 1.22 (d, J=6.4 Hz, 3H, CHMe); uv (H$_2$O) λ$_{max}$: 294 (ε7614), 266 (ε6936) nm; t$_½$ (pH 7.4, 36.8° C.) 14.0 h.

EXAMPLE 6

Preparation of (5R,6S)-3-[2-(4-hydroxymethylpyridinio)ethyl thio]-6-[1-(R)-hydroxyethyl]-7-oxo-1-azabicyclo[3.2.0-]hept-2-ene-2-carboxylate

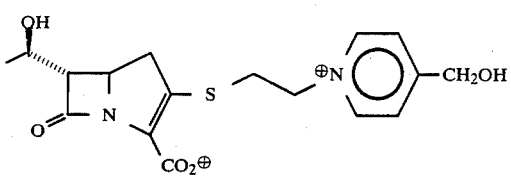

A. 4-Hydroxymethyl-1-(2-mercaptoethyl)pyridinium trifluoromethanesulfonate

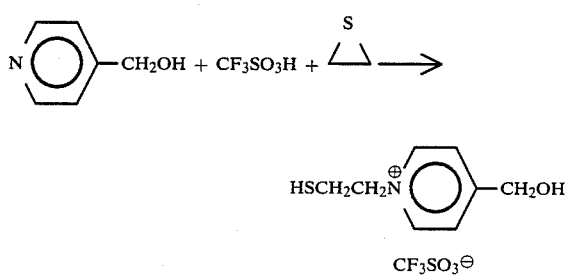

To a solution of 4-pyridinemethanol (1.635 g, 0.015 mol) in 10 mL of $CH_2Cl_2$, at 0° C. under $N_2$, was added dropwise trifluoromethanesulfonic acid (1.327 mL, 0.015 mol). A yellow-brown oil rapidly separated out. An additional equivalent of 4-pyridinemethanol (1.635 g, 0.015 mol) was added to this mixture and the solvent was removed under reduced pressure to give an oil. To this oil was added ethylene sulfide (0.891 mL, 0.015 mol) and the resulting homogeneous mixture was heated (oil bath) at about 60° C. for 3 h. The reaction mixture was then taken up in 15 mL of $H_2O$ and the aqueous solution was washed with $CH_2Cl_2$ (5×5 mL). After removing residual organic solvent in vacuo the aqueous solution was applied to a $C_{18}$ reverse-phase column. Elution with $H_2O$ and subsequent evaporation of the relevant fractions afforded an oil which was further dried in vacuo over $P_2O_5$ to give the product (4.64 g, 97%) as a colourless oil. ir (film) $\nu_{max}$: 3455 (s, OH), 2565, (w, SH) $cm^{-1}$; $^1$Hnmr ($d_6$-acetone) $\delta$: 9.07, 8.18 (ABq, J=6.8 Hz, 4H, aromatic), 5.03 (s, 2H, $CH_2OH$), 4.96 (t, J=6.5 Hz, 2H, $N-CH_2$), 4.09 (br s, 1H, —OH), 3.5–3.1 (m, 2H, $S-CH_2$), 2.25 (brs, 1H, —SH).

B. p-Nitrobenzyl (5R,6S)-3-[2-(4-hydroxymethylpyridinio)ethylthio]-6-[1-(R)-1-hydroxyethyl]-7-oxo-1-azabicyclo[3.2.0]hept-2-ene-2-carboxylate diphenylphosphate

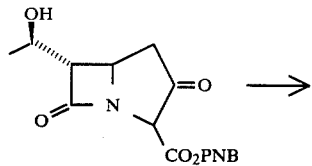

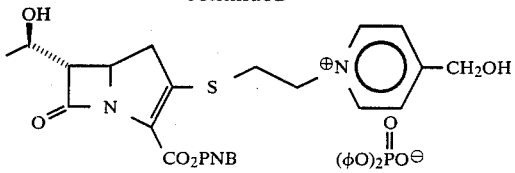

To a solution of p-nitrobenzyl (5R,6S)-6-[1-(R)-1-hydroxyethyl]-3,7-dioxo-1-azabicyclo[3.2.0]heptane-2-carboxylate (0.348 g, 1.0 mmol) in 5 mL of dry acetonitrile, at 0° C. under $N_2$, was added dropwise diisopropylethylamine (0.191 mL, 1.1 mmol) followed by diphenyl chlorophosphate (0.228 mL, 1.1 mmol). The resulting golden-yellow solution was stirred at 0° C. for 40 min. To this solution was added a solution of 4-hydroxymethyl-1-(2-mercaptoethyl)pyridinium trifluoromethanesulfonate (0.447 g, 1.4 mmol) in 1 mL of acetonitrile, followed by diisopropylethylamine (0.191 mL, 1.1 mmol). A reddish-black gum separated from the reaction mixture. After 20 min at 0° C. the reaction mixture was filtered and concentrated in vacuo. The residue was taken up in a minimum volume of acetonitrile-$H_2O$ (1:1) and applied to a $C_{18}$ reverse-phase column. Elution with 25% acetonitrile-$H_2O$ and subsequent lyophilization of the relevant fractions gave the product (0.353 g, 47%) as a cream-coloured solid. ir (KBr) $\lambda_{max}$: 3240 (br, OH), 1775 ($\beta$-lactam CO), 1695 (—$CO_2PNB$) $cm^{-1}$; $^1$Hnmr ($d_6$-acetone) $\delta$: 9.24–7.84 (m, H, aromatic), 7.4–6.9 (m, 10H, diphenylphosphate), 5.52, 5.24 (ABq, J=14 Hz, 2H, benzylic), 5.15–4.80 (m, 4H), 4.45–3.05 (m, 7H), 1.35 (d, J=6.6 Hz, 3H, CHMe).

C. (5R,6S)-3-[2-(4-hydroxymethylpyridinio)ethylthio]-6-[1-(R)-1-hydroxyethyl]-7-oxo-1-azabicyclo[3.2.0]hept-2-ene-2-carboxylate

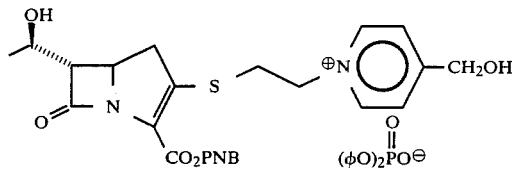

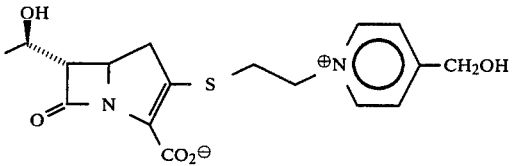

A mixture of p-nitrobenzyl (5R,6S)-3-[[2-(4-hydroxymethylpyridinio)ethylthio]-6-[1-(R)-1-hydroxyethyl]-7-oxo-1-azabicyclo[3.2.0]hept-2-ene-2-carboxylate diphenylphosphate (0.348 g, 0.465 mmol) and 10% palladium-on-charcoal (0.35 g) in 11 mL of phosphate buffer (0.05M, pH 7.4), 5 mL of THF and 10 mL of ether was hydrogenated at 40 psi for 1.25 h. The mixture was then filtered through a Celite pad and the aqueous phase was washed with ether (3 x). The pH of the aqueous solution was then adjusted to 7.0 using additional pH 7.4 buffer. After removing residual volatiles in vacuo the aqueous solution was applied to a $C_{18}$ reverse-phase column. Elution with 2% acetonitrile-$H_2O$ and subsequent lyophilization gave a yellow-brown solid. This material was rechromatographed (C18 reverse-phase/H2O) to give the desired product (0.060 g, 36%) as a light yellow solid. ir (KBr) ν$_{max}$: 3400 (br, OH), 1755 (β-lactam CO), 1590 (—CO$_2^-$) cm$^{-1}$; $^1$Hnmr (D$_2$O) δ: 8.73, 7.96 (ABq, J=6.8 Hz, 4H, aromatic), 4.93 (s, 2H, CH$_2$OH), 4.77 (t, J=6.0 Hz, 2H, N—CH$_2$), 4.15 (d of q, J=J'=6.3 Hz, 1H, H-1'), 3.96 (d of t, J=9.2 Hz, J'=2.6 Hz, 1H, H-5), 3.65–3.20 (m, 3H), 3.13–2.62 (m, 2H), 1.21 (d, J=6.3 Hz, 3H, CHMe); uv (H$_2$O) λ$_{max}$: 295 (ε6880), 256 (ε5595), 224 (ε8111) nm; t$_{½}$ (pH 7.4, 36.8° C.) 14.5 h.

EXAMPLE 7

Preparation of 3-[2-(1-(2-methylpyridinium))ethylthio]-6α-[1-(R)-hydroxyethyl]-7-oxo-1-azabicyclo(3.2.0)hept-2-ene-carboxylate

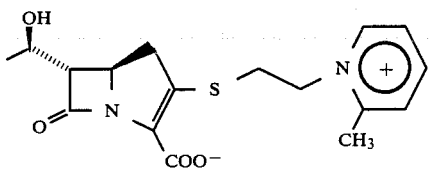

A. 1-(2-mercaptoethyl)-2-methylpyridinium methanesulfonate

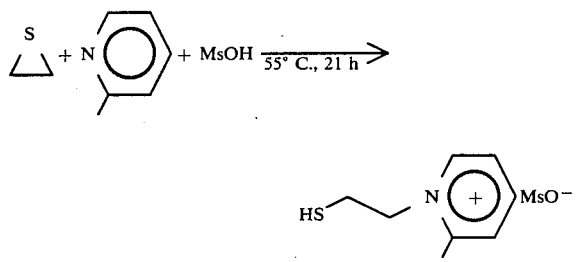

To a suspension of 2-methylpyridinium methanesulfonate in 2-methylpyridine prepared by the addition of methanesulfonic acid (0.65 mL, 0.010 mol) to cold 2-methylpyridine (2.17 mL, 0.022 mol) was added ethylene sulfide (0.655 mL, 0.011 mol). The reaction mixture was stirred under a nitrogen atmosphere at 55° C. for 21 h, cooled to 23° C. and diluted with water (5 mL). The aqueous solution was washed with ether (6×4 mL) pumped to remove traces of organic solvents and poured on top of a column (2.5×10.0 cm) of μ-bondapak C-18. The column was eluted with water and lyophilization of the appropriate fractions gave 2.13 g (85%) of the title compound, ir (film) ν$_{max}$: 2520 (SH), 1623 (pyridinium) 1574, 1512, 1485, 1412, 1195 (sulfonate), 1038 cm$^{-1}$, $^1$Hmr (DMSO-d$_6$+D$_2$O) δ: 2.37 (3H, s, CH$_3$SO$_3^-$), 2.83 (3H, s, CH$_3$ on pyridinium), 3.09 (2H, J=6.9 Hz, CH$_2$S), 4.71 (2H, t, J=6.9 Hz, CH$_2$N$^+$), 7.83 (2H, m, Hm of pyridinium), 8.44 (1H, m, Hp of pyridinium), 8.89 (1H, m, Ho of pyridinium), uv (H$_2$O) λ$_{max}$: 266 (ε3550) mμ.

B. Paranitrobenzyl 3-[2-(1-(2-methylpyridinium)ethylthio]-6α-[1-(R)-hydroxyethyl]-7-oxo-1-azabicyclo(8 3.2.0)hept-2-ene-2-carboxylate diphenylphosphate

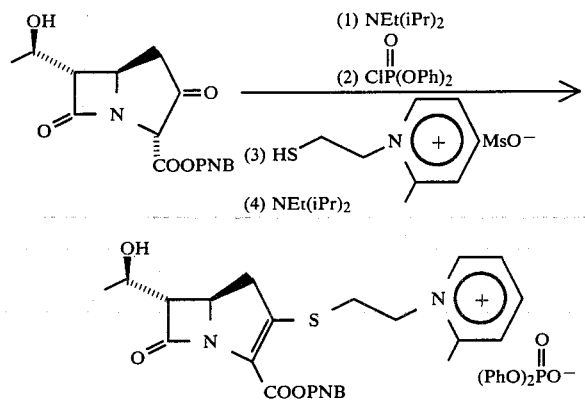

To a cold (0° C.) solution of p-nitrobenzyl 6α-[1-(R)-hydroxyethyl]-3,7-dioxo-1-azabicyclo[3.2.0]hept-2-ene-2-carboxylate (0.523 g, 1.50 mmol) in acetonitrile (6 mL) kept under a nitrogen atmosphere was added diisopropylethylamine (0.314 mL, 1.80 mmol) followed by diphenyl chlorophosphate (0.373 mL, 1.80 mmol). The reaction mixture was stirred for 30 min at 0° C. and treated with solution of 1-(2-mercaptoethyl)-2-methylpyridinium methanesulfonate (0.530 g, 2.16 mmol) in acetonitrile (18 mL) followed by diisopropylethylamine (0.314 mL, 1.8 mmol). The reaction mixture was stirred at 0° C. for 1 h diluted with cold (0° C.) water (26 mL) and poured on top of a column (3.5×7.0 cm) of μ-bondapak C-18. Elution of the column with 25% acetonitrile—75% water and with 50% acetonitrile—50% water gave after lyophilization of the appropriate fractions 1.06 g, (96%) of the title compound as a yellowish powder, ir (KBr) ν$_{max}$: 3650–3100 (OH), 1770 (C=O of β-lactam), 1695 and 1690 (C=O of PNB ester), 1630 (pyridinium), 1595 (phenyl), 1518 (NO$_2$), 1335 (NO$_2$), 890 cm$^{-1}$ (NO$_2$); $^1$Hmr (DMSO, d$_6$) δ: 1.15 (3H, d, J=6.1 Hz, CH$_3$CHOH), 2,87 (s, CH$_3$ on pyridinium), 3.6–4.4 (2H, m, H-5, CH$_3$CHOH), 4.75 (2H, m, CH$_2$N$^+$), 5.37 (center of ABq, J=14 Hz, CH$_2$ of PNB), 6.5–7.4 (10H, m, phenyl), 7.70 (2H, d, J=8.8 Hz, Ho of PNB), 8.0 (2H, m, Hm of pyridinium), 8.24 (2H, d, J=8.8 Hz, Hm of PNB), 8.50 (1H, m, Hp of pyridinium), 8.95 (1H, brd, J=6.1 Hz, Ho of pyridinium), uv (H$_2$O) λ$_{max}$: 265 (ε11990), 314 (ε8020)mμ.

C.

3-[2-(1-(2-methylpyridinium))ethylthio]-6α-[1-(R)-hydroxyethyl]-7-oxo-1-azabicyclo(3.2.0)hept-2-ene-carboxylate

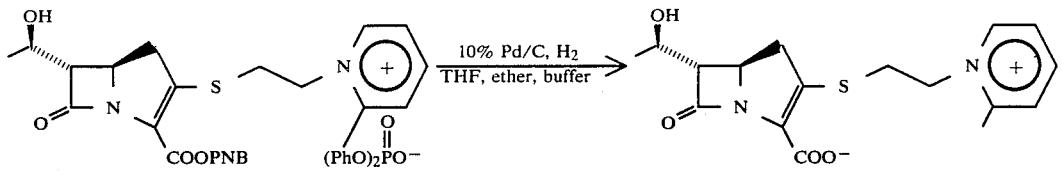

To a solution of p-nitrobenzyl 3-[2-(1-(2-methyl-pyridinium))ethylthio)-6α-[1-(R)-hydroxyethyl]-7-oxo-1-azabicyclo(3.2.0)hept-2-ene-2-carboxylate diphenylphosphate (0.66 g, 0.90 mmol) in wet tetrahydrofuran (34 mL) was added ether (34 mL), potassium phosphate monobasic-sodium hydroxide buffer (0.15M, 16.5 mL, pH 7.22) and 10% palladium on charcoal (0.66 g). The resulting mixture was hydrogenated under 40 psi at 23° C. for 1.25 h. The organic layer was separated and extracted with buffer (2×6 mL). Water layers were combined, filtered through a Celite pad, washed with ether (40 mL), pumped to eliminate traces of organic solvents and poured on top of a column (2.5×10 cm) of μ-bondapak C-18. Elution of the column with water and lyophylization of the appropriate fractions gave the title compound 0.098 g (31%) as a yellowish powder, ir (KBr) $\nu_{max}$: 3650–3100 (OH), 1755 (C=O of β-lactam), 1630 (pyridinium), 1595 cm$^{-1}$ (carboxylate), $^1$Hmr (D$_2$O) δ: 1.20 (3H, d, J=6.3 Hz, CH$_3$CHOH), 2.83 (s, CH$_3$ on pyridinium), 2.7–3.1 (5H, H-4, CH$_3$ on pyridinium), 3.1–3.7 (3H, m, CH$_2$S, H-6), 3.90 (dd, J=9.1 Hz, J=2.6 Hz, H-5), 3.1 (m, CH$_3$CHOH), 4.78 (t, J=6.2 Hz, CH$_2$N$^+$), 7.8 (2H, m, Hm of pyridinium), 8.3 (1H, m, Hp of pyridinium), 8.65 (1H, m, Ho of pyridinium), uv (H$_2$O) λ$_{max}$: 268 (ε9350), 296 (ε8840), mμ, [α]$_D^{23}$+41° [c 0.5, H$_2$O), τ$_\frac{1}{2}$=15.0 h (measured at a concentration of 10$^{-4}$M in phosphate buffer pH 7.4 at 36.8° C.).

EXAMPLE 8

Preparation of 3-[2-(1-(4-methylpyridinium))ethylthio]-6α-[1(R)-hydroxyethyl]-7-oxo-1-azabicyclo(3.2.0)hept-2-ene-2-carboxylate

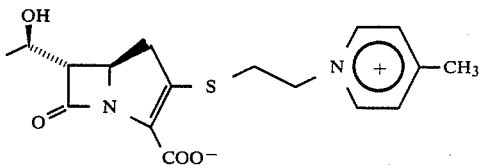

A.
1-(2-merceptoethyl)-4-methylpyridinium)methanesulfonate

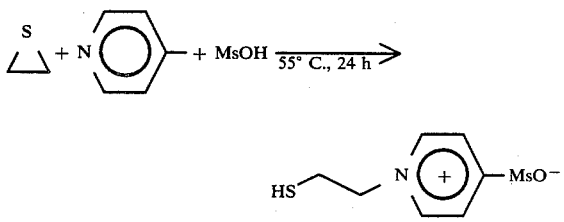

To a suspension of 4-picolinium methanesulfonate in 4-picoline prepared by the addition of methanesulfonic acid (0.65 mL, 0.010 mol) to 4-picoline (2.14 mL, 0.022 mol) in cooling was added ethylene sulfide (0.655 mL, 0.011 mol). The reaction mixture was stirred under a nitrogen atmosphere at 55° C. for 24 h, cooled to 23° C. and diluted with water (5 mL) and ether (10 mL). The organic layer was separated and the aqueous layer was washed with ether (5×5 mL) and applied on top of a column (2.5×10 cm) of μ-bondapak C-18 after traces of ether have been removed under reduced pressure. Elution of the column with 15% acetonitrile 85% water mixture gave after lyophylization of the appropriate fractions a colorless syrup 2.66 g (100%), ir (film) $\nu_{max}$: 2500 (SH), 1640 (pyridinium), 1572, 1520, 1478, 1200 (sulfonate), 1040, 833 and 768 cm$^{-1}$, $^1$Hmr (DMSO-d$_6$) δ: 2.31 (3H, s, CH$_3$SO$_3^-$), 2.62 (s, CH$_3$ on pyridinium), 2.2–2.9 (4H, SH, CH$_3$ on pyridinium), 3.04 (2H, m, CH$_2$S), 4.68 (2H,t, J=6.4 Hz, CH$_2$N$^+$), 8.01 (2H, d, J=6.6 Hz, Hm of pyridinium), 8.89 (2H, d, J=6.6 Hz, Ho of pyridinium), uv (H$_2$O) λ$_{max}$: 256 (ε4100), 221 (ε7544) mμ.

B. 1-(2-mercaptoethyl)-4-methylpyridinium p-toluenesulfonate

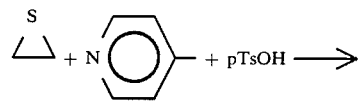

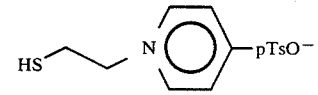

To a suspension of p-toluenesulfonic acid (1.72 g, 0.01 mol) in benzene (6.5 mL) was added 4-picoline (1.17 mL, 0.012 mL). The resulting mixture was stirred under a nitrogen atmosphere at 23° C. for 30 min, treated with ethylenesulfide (0.65 mL, 0.011 mol) and stirred at 75° for 24 h. More ethylenesulfide (0.65 mL, 0.011 mol) was added and the stirring was continued at 75° C. for 24 h more. The reaction mixture was cooled to 23° C. and diluted with water (5 mL) and ether (8 mL). The aqueous layer was separated and washed with ether (3×8 mL). The traces of organic solvents were removed under vacuum and the compound was chromatographed on μ-bondapak C-18 with water as eluting solvent to give 2.94 g (90%) of the title compound as a colorless syrup; ir (film) $\nu_{max}$: 2510 (SH) 1640 (pyridinium), 1595, 1582, 1475, 1200 (sulfonate), 1031, 1010, 818 cm$^{-1}$, $^1$Hmr (DMSO, d$_6$) δ: 2.29 (3H, s, CH$_3$ on pyridinium), 2.61 (s, CH$_3$ Ph), 2.4–2.8 (4H, SH, CH$_3$Ph), 3.03 (2H, m[addition of D$_2$O gave a t, J=6.4 Hz, at 3.04], CH$_2$S), 4.68 (2H, t, J=6.4 Hz, CH$_2$N$^+$), 7.11, 7.49 (4H, 2d, J=7.9 Hz, Phenyl), 8.00 (2H, d, J=6.5 Hz, Hm of pyridinium), 8.89 (2H, d, J=6.5 Hz, Ho of pyridinium), uv (H$_2$O) λ$_{max}$: 256 (ε4315), 222 (ε17045) mμ.

C. Paranitrobenzyl 3-[2-(1-(4-methylpyridinium)ethylthio]-6α-[1-(R)-hydroxyethyl]-7-oxo-1-azabicyclo(3.2.0)hept-2-ene-2-carboxylate diphenylphosphate

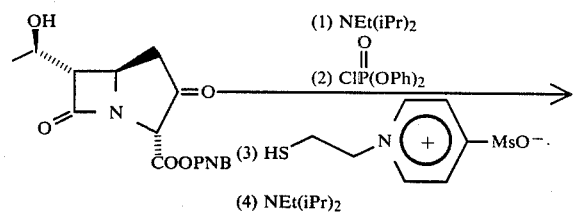

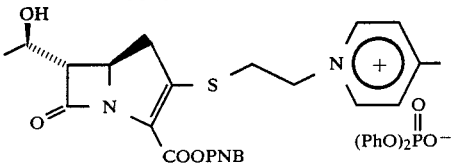

To a cold (0° C.) solution of p-nitrobenzyl 6α-[1-(R)-hydroxyethyl]-3,7-dioxo-1-azabicyclo(3.2.0)hept-2-ene-carboxylate (0.522, 1.5 mmol) in acetonitrile (6 mL) kept under a nitrogen atmosphere was added diisopropylethylamine (0.314 mL, 1.8 mmol) followed by diphenyl chlorophosphate (0.373 mL, 1.9 mmol). The reaction mixture was stirred for 45 min and treated dropwise with a solution of 1-(2-mercaptoethyl)-4-methylpyridinium methanesulfonate (0.539, 2.16 mmol) in acetonitrile (1.8 mL) followed by diisopropylethylamine (0.314 mL, 1.8 mmol). The reaction mixture was stirred at 0° C. for 1 h, diluted with cold (0° C.) water (24 mL) and poured on top of a column (2.5×8.5 cm) of μ-bondapak C-18. Elution of the column first with 25% acetonitrile —75% water mixture (100 mL) then with 50% acetonitrile 50% water mixture (100 mL) afforded after lyophilization of the appropriate fractions 0.91 g (83%) of the title compound as a yellowish powder, ir (KBr) $\nu_{max}$: 3700–2800 (OH), 1770 (C=O of β-lactam), 1700 (C=O of PNB ester), 1640 (pyridinium), 1595 (phenyl), 1520 (NO₂), 1340 (NO₂), 890 cm⁻¹ (NO₂), ¹Hmr (DMSO, d₆)δ: 1.16 (3H, d, J=6.2 Hz, CH₃CHOH), 2.61 (s, CH₃ on pyridinium), 3.1–3.7 (3H, m, H-6, CH₂S), 3.7–4.4 (2H, m, H-5, CH₃CHOH), 4.79 (2H, brt, J=6.3 Hz, CH₂N⁺), 5.17 (d, J=4.9 Hz, OH), 5.37 (center of ABq, J=14.1 Hz, CH₂ of PNB), 6.7–7.4 (10H, m, phenyl), 7.69 (2H, d, J=8.8 Hz, Ho of PNB), 8.00 (2H, d, J=6.5 Hz, Hm of pyridinium), 8.23 (2H, d, J=8.8 Hz, Hm of PNB), 8.92 (2H, d, J=6.5 Hz, Ho of pyridinium), uv (H₂O) $\lambda_{max}$: 262 (ε10835), 311 (ε9670) mμ. Anal. calcd. for C₃₆H₃₆N₃O₁₀SP.1.5H₂O: C 56.84, H 5.17, N 5.52, S 4.21; found: C 56.89; H 5.13, N 5.19, S 4.41.

D.
3-[2-(1-(4-methylpyridinium)ethylthio]-6α-[1-(R)-hydroxyethyl)-7-oxo-1-azabicyclo(3.2.0)hept-2-ene-2-carboxylate

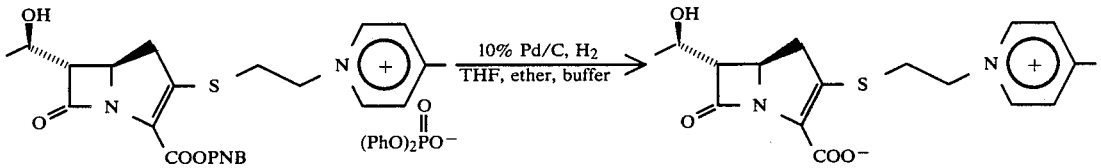

To a solution of p-nitrobenzyl 3-[2-(1-(4-methyl-pyridinium))ethylthio]-6α-[1-(R)-hydroxyethyl]-7-oxo-1-azabicyclo(3.2.0)hept-2-ene-2-carboxylate diphenyl-phosphate (0.587 g, 0.80 mmol) in wet tetrahydrofuran (30 mL) was added ether (30 mL), potassium phosphate mono basic-sodium hydroxide buffer (0.15M, 14.7 mL, pH 7.22) and 10% palladium on charcoal (0.59 g). The resulting mixture was hydrogenated under 40 psi at 23° C. for 1.25 h. The organic layer was separated and extracted with the buffer (2×6 mL). The aqueous extracts were combined, filtered through a Celite pad, washed with ether (3×20 mL), pumped to remove traces of organic solvents and poured on top of a column (2.5×10 cm) of μ-bondapak C-18. Elution of the column with water and lyophylization of the appropriate fractions gave 0.136 g (49%) of the title compound as a yellowish powder, ir (KBr) $\nu_{max}$: 3700–3000 (OH), 1770 (C=O of β-lactam), 1642 (pyridinium) 1592 cm⁻¹ (carboxylate), ¹Hmr (D₂O) δ: 1.19 (3H, t, J=6.3 Hz, CH₃CHOH), 2.59 (3H, s, CH₃ on pyridinium), 2.84 (d, J=9.1 Hz, H-4), 2.90 (d, J=9.1 Hz, H-4), 3.0–3.6 (3H, m, CH₂S, H-6), 3.86 (dd, J=9.1 Hz, J=2.6 Hz, H-5), 4.12 (m, CH₃CHOH), 4.5–4.9 (CH₂N⁺ masked by HOD), 7.80 (2H, d, J=6.6 Hz, Hm of pyridinium), 8.58 (2H, d, J=6.6 Hz, Ho of pyridinium), uv (H₂O) $\lambda_{max}$: 256 (ε5510), 262 (ε5360), 296 (ε7050) m, $[\alpha]_D^{23}$ +20.8° (C 0.48, H₂O), $\tau_{\frac{1}{2}}$ = 12.8 h (measured at a concentration of 10⁻⁴M in a phosphate buffer pH 7.4 at 36.8° C.).

EXAMPLE 9

Preparation of (5R) 3-[2-(4-methylthiopyridinio)ethylthio]-(6S)-[(1R)-hydroxyethyl]-7-oxo-1-azabicyclo[3.2.0]hept-2-ene-2-carboxylate

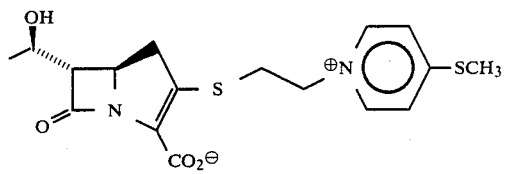

A. 4-Methylthiopyridine*

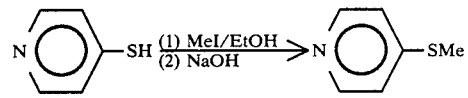

*Preparation of this compound was reported in King and Ware, J. Chem. Socl, 873(1939). The procedure, described in this reference was followed.

4-Mercaptopyridine (5.55 g, 50.0 mmol; Aldrich) was dissolved in boiling abs. EtOH (50 mL). The insoluble material was removed by filtration over Celite. The filtrate was heated to re-dissolve, and when it cooled to ca. 50° C., methyl iodide (3.17 mL, 51.0 mmol; Aldrich) was added at once. The mixture was cooled to crystallize. Filtration of the solid gave 6.77 g (26.7 mmol, y. 53.5%) of the title compound as the hydriodide: ¹Hmr (D₂O) δ: 2.70 (3H, s, —SCH₃) and 7.65–7.77–8.35–8.48 ppm (4H, A₂B₂ type, aromatic-Hs); ir (Nujol) $\nu_{max}$: 1615, 1585 (aromatic) and 780 cm⁻¹; uv (H₂O) $\lambda_{max}$: 227 (ε2.02×10⁴) and 298 nm (ε1.64×10⁴).

The hydriodide (6.33 g, 25.0 mmol) was dissolved in H₂O (40 mL) and the insoluble material was removed and washed with H₂O (10 mL). To the filtrate was added at 0°–5° NaOH pellet (5 g) and extracted with Et₂O (3×25 mL), saturating the aqueous layer with NaCl. The combined organic extracts were washed with brine (×2), dried (MgSO₄) and evaporated, yielding 2.92 g (23.4 mmol, overall yield 50%) of the title compound as an oil: ¹Hmr (CDCl₃) δ: 2.48 (3H, s, —SCH₃) and 7.03–7.13–8.38–8.48 ppm (4H, A₂B₂type, aromatic-Hs); ir (film) $v_{max}$: 1580 and 800 cm⁻¹.

B. 4-Methylthio-N-(2-mercaptoethyl)pyridinium methanesulfonate

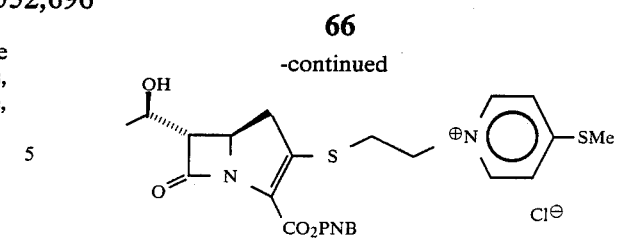

4-Methylthiopyridine (2.75 g, 22.0 mmol) was added slowly to methanesulfonic acid* (0.65 mL, 10.5 mmol) by cooling in an ice-bath. To this solid was added ethylene sulfide* (0.66 mL, 11.0 mmol, Aldrich) and the mixture was heated at 50°–60° C. for 21 h. As reaction proceeds the solid went to solution. After cooling, the reaction mixture was dissolved in H₂O (5 mL) and washed with Et₂O (5×4 mL). The cloudy aqueous layer was filtered over Celite and the filtrate was purified by reverse phase silica gel column chromatography (C₁₈ micro bondapack 10 g) eluting with H₂O. Each fraction of 10 mL was collected. Fractions 2 and 3 were combined and repurified by the reverse phase column. Fraction 2 gave 1.258 g (4.48 mmol, y. 42.6%) of the title compound as a viscous oil: ¹Hmr (DMSO-d₆, CFT-20) δ: 2.32 (3H, s, MeSO₃⊖), 2.72 (3H, s, —SMe), 2.68 (1H, m, SH), 2.9–3.2 (3H, m, —CH₂S—), 4.59 (2H, t, J=6.4 Hz, —CH₂N⊕), 7.97 (2H, "d", J=7.2 Hz, aromatic-Hs) and 8.72 ppm (2H, "d", J=7.2 Hz, aromatic-Hs); ir (neat) $v_{max}$: 1630, 1200 (br, —SO₃⊖), 785 and 770 cm⁻¹.

*These reagents were distilled prior to use.

C. (5R) p-Nitrobenzyl 3-[2-(4-Methylthiopyridino)ethylthio]-(6S)-[(1R)-hydroxyethyl]-7-oxo-1-azabicyclo[3.2.0]hept-2-ene-2-carboxylate chloride

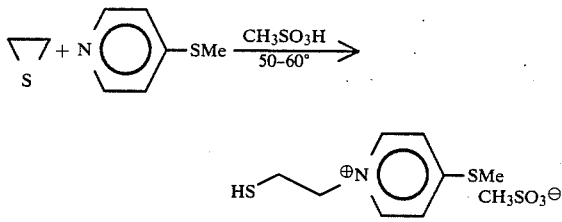

To a solution of (5R) p-nitrobenzyl 3,7-dioxo-(6S)-[(1R)-hydroxyethyl]-1-azabicyclo[3.2.0]heptane-(2R)-carboxylate (475 mg, 1.36 mmol) and diisopropylethylamine (0.24 mL, 1.4 mmol) in CH₃CN (5 mL) was added at 0°–5° C. under a nitrogen atmosphere diphenyl chlorophosphate (0.29 mL, 1.41 mmol). The mixture was stirred at 0°–5°, for 30 min. To this mixture was added an oily suspension of 4-methylthio-N-(2-mercaptoethyl)pyridinium methanesulfonate (678 mg, 1.45 mmol; 60% pure) in CH₃CN (1.5 mL) followed by diisopropylethylamine (0.24 mL, 1.4 mmol). The mixture was stirred at 0°–5° C. for 1 h. Immediately after addition of the base, yellowish precipitate formed. The precipitate was filtered and washed with cold CH₃CN (3 mL), yielding 314 mg of yellowish solid. This was triturated from 10% MeOH in H₂O (5 mL) to obtain 341 mg (0.618 mmol, y. 45.4%) of the title compound as white crystals: mp 118°–120° C.; ¹Hmr (DMSO-d₆, CFT-20) δ: 1.16 (3H, d, J=6.1 Hz, 1'-CH₃), 2.72 (3H, s, —CH₃), 3.1–3.7 (5H, m), 3.7–4.3 (2H, m), 4.71 (2H, t, J=6.3 Hz, —CH₂N⊕), 5.15 (1H, d, J=4.9 Hz, OH), 5.20–5.35–5.40–5.55 (2H, ABq, CO₂CH₂-Ar), 7.70 (2H, "d" J=8.8 Hz, nitrophenyl-Hs), 7.97 (2H, "d", J=7.0 Hz, pyridinio-Hs), 8.25 (2H, "d", J=8.8 Hz, nitrophenyl-Hs), and 8.76 ppm (2H, "d", J=7.1 Hz, pyridinio-Hs); ir (Nujol) $v_{max}$: 3250 (OH), 1775 (β-lactam), 1700 (ester) and 1625 cm⁻¹ (pyridinio); uv (abs, EtOH) $\lambda_{max}$: 308 nm (ε4.47×10); $[\alpha]_D^{23°}$ +24.8 (c 0.5, MeOH); Anal. calcd. for C₂₄H₂₆N₃O₆S₂Cl.H₂O: C 50.56, H 4.95, N 7.37; Found: C 50.63, H 4.72, N 6.89.

D. (5R) 3-[2-(4-Methylthiopyridinio)ethylthio]-(6S)-[(1R)-hydroxyethyl]-7-oxo-1-azabicyclo[3.2.0]hept-2-ene-2-carboxylate

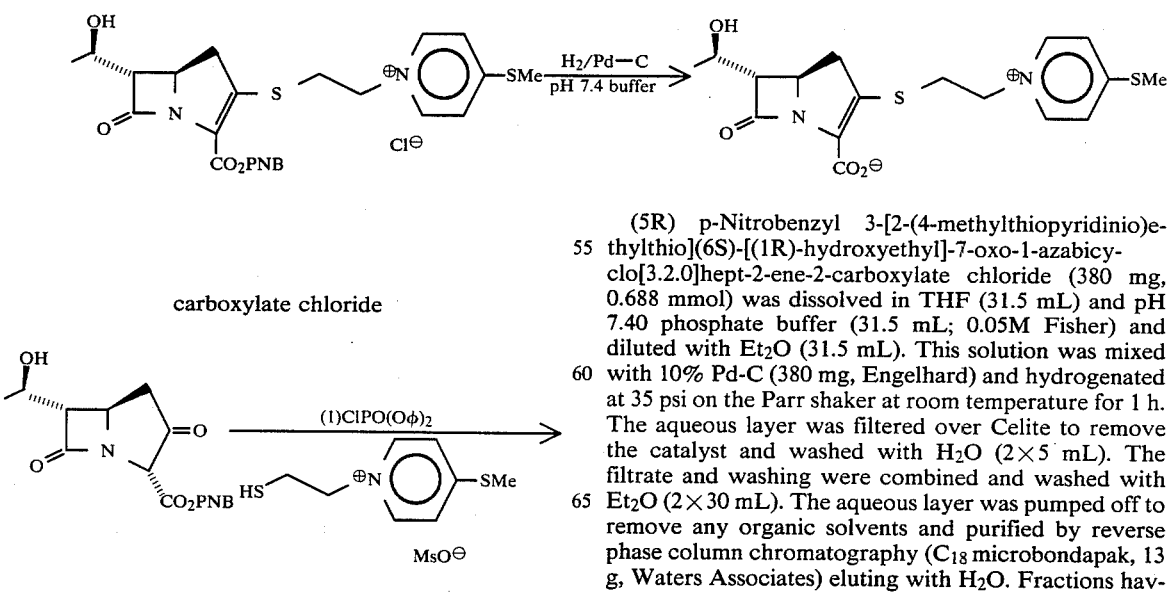

(5R) p-Nitrobenzyl 3-[2-(4-methylthiopyridinio)ethylthio](6S)-[(1R)-hydroxyethyl]-7-oxo-1-azabicyclo[3.2.0]hept-2-ene-2-carboxylate chloride (380 mg, 0.688 mmol) was dissolved in THF (31.5 mL) and pH 7.40 phosphate buffer (31.5 mL; 0.05M Fisher) and diluted with Et₂O (31.5 mL). This solution was mixed with 10% Pd-C (380 mg, Engelhard) and hydrogenated at 35 psi on the Parr shaker at room temperature for 1 h. The aqueous layer was filtered over Celite to remove the catalyst and washed with H₂O (2×5 mL). The filtrate and washing were combined and washed with Et₂O (2×30 mL). The aqueous layer was pumped off to remove any organic solvents and purified by reverse phase column chromatography (C₁₈ microbondapak, 13 g, Waters Associates) eluting with H₂O. Fractions having a uv absorption at 307 nm were collected (ca. 1 L) and lyophilized to obtain 127 mg (0.334 mmol, y. 48.5%) of the title compound as a yellowish powder: $^1$Hmr (D$_2$O, CFT-20)δ: 1.20 (3H, d, J=6.4 Hz, 1'-CH$_3$), 2.64 (3H, s, —SCH$_3$), 2.81 (2H, m, —SCH$_2$—), 3.19 (1H, dd, J$_{6-1'}$=6.1 Hz, J$_{6-5}$=2.6 Hz, 6-H), 3.32 (2H, dd, J=11 Hz, J=5.5 Hz, 4-Hs), 3.92 (1H, dt, J=9.2 Hz, J$_{5-6}$=2.6 Hz, 5-H), 4.1 (1H, m, 1'-H), 4.61 (2H, t, J=5.9 Hz, —CH$_2$N⊕), 7.70 (2H, "d", J=7.1 Hz, aromatic-Hs), and 8.40 ppm (2H, "d", J=7.1 Hz, aromatic-Hs); ir (KBr, disc) ‖$_{max}$: 3400 (OH), 1750 (β-lactam), 1630 (pyridinium) and 1590 cm$^{-1}$ (carboxylate); uv (H$_2$O) λ$_{max}$: 231 (ε9800) and 307 nm (ε25000); [α]$_D^{23°}$ +3.14 (c 0.5, H$_2$O).

EXAMPLE 10

Preparation of
3-[2-(3-methoxy-1-pyridinium)ethylthio]-6α-[1'-(R)-hydroxyethyl]-7-oxo-1-azabicyclo(3.2.0)hept-2-ene-2carboxylate

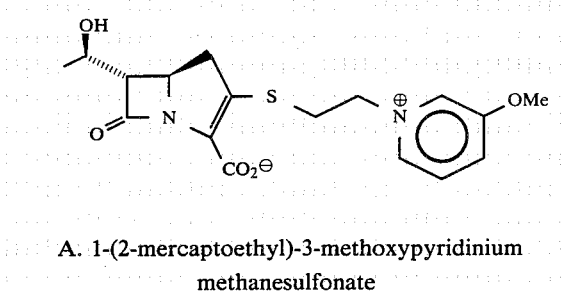

A. 1-(2-mercaptoethyl)-3-methoxypyridinium methanesulfonate

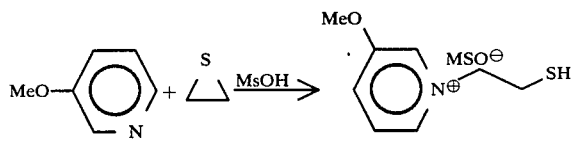

To precooled (5° C.) 3-methoxypyridine (698 mg, 6.4 mmol) was added dropwise methanesulfonic acid (0.216 mL, 3.05 mmol) and ethylene sulfide (0.19 mL, 3.2 mmol). The mixture was then heated at 60° C. for 18 h, cooled to 20° C., diluted with water (10 mL) and washed with ether (3×10 mL). The aqueous phase was pumped under high vacuum for 15 min and poured on a C$_{18}$ reverse phase column. The title compound was eluted with water. The appropriate fractions were combined and evaporated under high vacuum to give the desired thiol (61.6 mg, yield 76.3%); ir (CH$_2$Cl$_2$) ν$_{max}$:2550 (w, SH) and 1620, 1600, 1585 cm$^{-1}$ (m, aromatic); $^1$Hmr (DMSO d$_6$) δ: 8.90–7.90 (4H, m, aromatic C-H), 4.72 (2H, t, J=6.6 Hz, CH$_2$N$^+$), 4.01 (3H, s, OCH$_3$), 3.5–3.0 (m, hidden CH$_2$S), 2.66 (1H, dd, J=9.6 Hz, J=7.5 Hz, SH) and 2.31 ppm (3H, s, CH$_3$SO$_3$).

B. para-Nitrobenzyl 3[2-(3-methoxy-1-pyridinium chloride)ethylthio]-6α-[1'-(R)-hydroxyethyl]-7-oxo-1-azabicyclo(3.2.0)-hept-2-ene-2-carboxylate

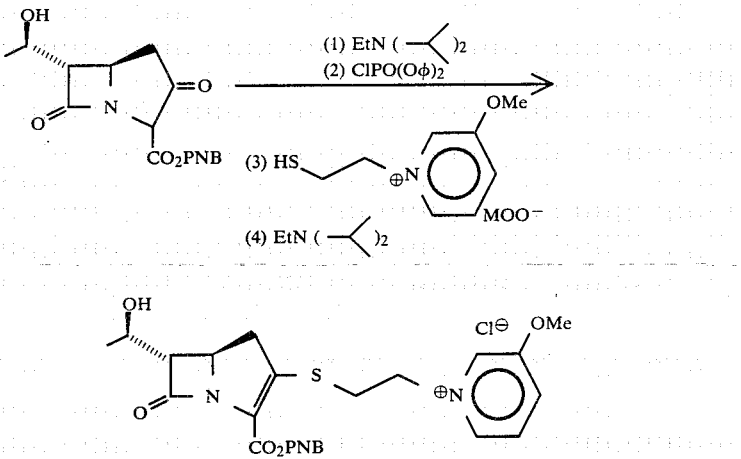

A cold (0° C.) solution of p-nitrobenzyl 6α-[1'-(R)-hydroxyethyl]-3,7-dioxo-1-azabicyclo-(3.2.0)-heptane-2-carboxylate (1.04 g, 3 mmol) in acetonitrile (12 mL) was treated dropwise with diisopropylethyl amine (0.63 mL, 3.6 mmol) and diphenylchlorophosphate (0.75 mL, 36 mmol) and stirred at 0° C. for 30 min. The resulting enol phosphate was treated with 1-(2-mercaptoethyl)-3-methoxypyridinium methanesulfonate (1.14 g, 4.30 mmol) in CH$_3$CN(7 mL), diisopropylethylamine (0.63 mL, 4.30 mmol), stirred for 30 min. and cooled at −10° C. for 30 min. The solid that precipitated out of the mixture was filtered, washed with cold acetonitrile (2 mL) and dried to give the title compound (1.32 g, yield 82%); ir (nujol) ν$_{max}$ 3320 (m, OH), 1780, 1765 (s, β-lactam C═O), 1700, 1695 (m, ester C═O) and 1520 cm$^{-1}$ (s, NO$_2$); $^1$Hmr (DMSO d$_6$) δ: 9.01 (1H, bs, H-3 aromatic), 8.75 (1H, bd, J=5.4 Hz, H-6 aromatic), 8.35–7.95 (4H, m, H-aromatic), 7.70 (2H, d, J=7.7 Hz, H-aromatic), 5.37 (2H, center of ABq, J=13 Hz, CH$_2$PNB), 5.17 (1H, d, J=4.9 Hz, OH), 4.87 (2H, t, J=6.3, CH$_2$-N⊕), 4.35–3.75 (2H, m, H-5 and H-1'), 4.00 (3H, s, OCH$_3$) 3.56 (part of a t, J=6.3 Hz, CH$_2$S), 3.5–3.20 (3H, m, H-6, H-3) and 1.16 ppm (3H, d, J=6.1 Hz, CH$_3$CHO).

C.
3-[2-(3-methoxy-1-pyridinium)ethylthio]-6α-[1'-(R)-hydroxyethyl]-7-oxo-1-azabicyclo(3.2.0)-hept-2-ene-2-carboxylate.

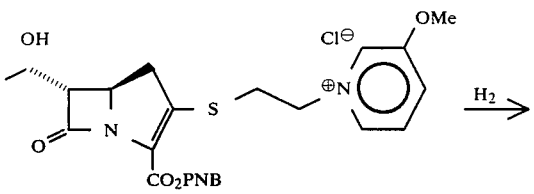

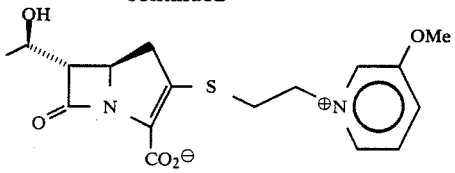

A solution of para-nitrobenzyl 3[2-(3-methoxy-1-pyridinium chloride)ethylthio]-6α-[1'-(R)-hydroxyethyl]-7-oxo-1-azabicyclo(3.2.0)-hept-2-ene-2-carboxylate (600 mg, 1.12 mmol) in THF (25 mL), ether (25 mL) and pH 7.4 phosphate buffer (0.1M, 25 mL) was hydrogenated in a Parr shaker over 10% Pd/C (1.1 g) for 1 h at 40 psi. The mixture was diluted with ether and the aqueous phase was filtered through a #52 hardened filter paper. The aqueous layer was washed with ether (2×20 mL) pumped under vacuum and poured on a silica gel reverse phase column. The title compound was eluted with water containing 2 and 5% acetonitrile. The appropriate fractions were combined and lyophilized to give a yellow solid that was repurified by hplc to give the penem carboxylate (150 mg, 38%); ir (nujol) $\nu_{max}$ 1750 (s, β-lactam C=O) and 1580 cm$^{-1}$ (s, carboxylate); $^1$Hmr (D$_2$O) δ: 8.55-8.30 (2H, m, H-2, H-6 aromatic), 8.17-7.75 (2H, m, H-3, H-4 aromatic), 4.77 (2H, t, J=5.9 Hz, CH$_2$N$^⊕$), 4.10 (1H, part of 5 lines, J=6.3 Hz, H-1'), 3.97 (3H, s, OCH$_3$), 3.85, 3.82 (2 lines, part of dt, J=2.6 Hz, part of H-5), 3.42 (2H, t, J=5.9 Hz, CH$_2$-S), 3.25 (1H, dd, J=6.1 Hz, J=2.6 Hz, H-6), 2.99-2.60 (2H, 6 lines, part of H-3) and 1.20 ppm (3H, d, J=6.4 Hz, CH$_3$); uv (H$_2$O, c 0.05) λ$_{max}$: 290 (ε10517), 223 (ε6643); T$_½$ (0.1M pH 7.4 phosphate buffer, 37° C.) 20 h.

EXAMPLE 11

Preparation of (5R,6S)-3-[[2-(3-methylthiopyridinio)ethyl]thio]-6-[1-(R)-hydroxyethyl]-7-oxo-1-azabicyclo[3.2.0]hept-2-ene-2-carboxylate

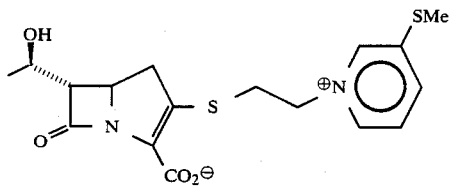

A. 3-Methylthio-1-(2-mercaptoethyl)pyridinium chloride

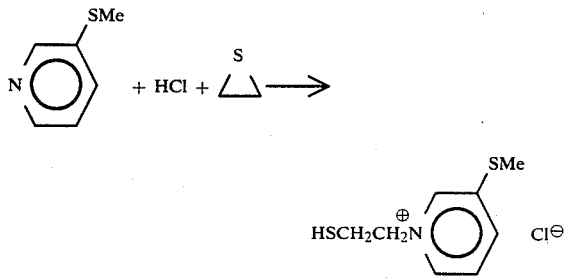

To a solution of 3-methylthiopyridine[1] (2.00 g, 0.016 mol) in 10 mL of ether was added 15 mL of 1N HCl and the mixture was well shaken. The aqueous phase was separated, washed with 10 mL of ether and then evaporated. The residual hydrochloride was then dried in vacuo (P$_2$O$_5$) to give a white solid. To this solid hydrochloride was added 3-methylthiopyridine (1.88 g, 0.015 mol) and ethylene sulfide (0.89 mL, 0.015 mol) and the resulting mixture was heated (oil bath) at 55°-65° C. under N$_2$ for 15 h. This gave a slightly turbid oil which was taken up in 125 mL of H$_2$O and washed with CH$_2$Cl$_2$. The aqueous solution was concentrated to about 25 mL and then a few drops of acetonitrile were added to make the mixture homogeneous. The resulting aqueous solution was applied to a C$_{18}$ reverse-phase column. Elution with H$_2$O and subsequent evaporation of the relevant fractions afforded the product (2.66 g 80%) as a pale yellow, viscous oil. ir (film) $\nu_{max}$: 2410 (br, —SH) cm$^{-1}$; $^1$Hnmr (d$_6$-DMSO+D$_2$O) δ: 8.88-7.88 (m, 4H, aromatic), 4.70 (t, J=6.5 Hz, 2H, N-CH$_2$), 3.08 (skewed t, J=6.5 Hz, 2H, S-CH$_2$), 2.64 (s, 3H, S-Me). [1]Prepared by the method of J. A. Zoltewiez and C. Nisi, J. Org. Chem. 34, 765 (1969).

B. p-Nitrobenzyl (5R,6S)-3-[2-(3-methylthiopyridinio)ethyl thio]-6-[1-(R)-hydroxyethyl]-7-oxo-1-azabicyclo[3.2.0-]hept-2-ene-2-carboxylate chloride

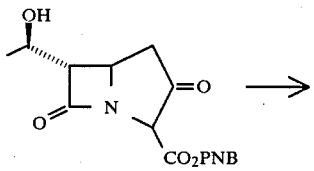

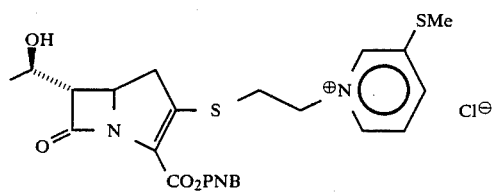

A solution of p-nitrobenzyl (5R,6S)-6-[1-(R)-hydroxyethyl]-3,7-dioxo-1-azabicyclo[3.2.0]heptane-2-carboxylate (0.522 g, 1.50 mmol) in 7 mL of dry acetonitrile was cooled at 0° C. and then diisopropylethylamine (0.287 mL, 1.65 mmol) was added dropwise. To the resulting yellow-brown solution was added dropwise diphenyl chlorophosphate (0.342 mL, 1.65 mmol) and the reaction mixture was kept at 0° C. for 30 min. Diisopropylethylamine (0.313 mL, 1.80 mmol) was then added, followed by a solution of 3-methylthio-1-(2-mercaptoethyl)pyridinium chloride (0.398 g, 1.80 mmol) in 0.70 mL of dry DMF. About a minute after the addition was complete a precipitate separated from the reaction mixture and further cooling at −10° C. for 10 min gave a solid orange-coloured mass. This solid was subsequently triturated with acetontrile and the residue was collected by filtration. The residue was washed with acetonitrile, then acetone and finally dried in vacuo to give the product (0.455 g, 55%) as a cream-coloured solid. The combined filtrate was evaporated to give a yellow oil which was taken up in a minimum volume of acetonitrile and cooled at 0° C. for 30 min. Filtration of this mixture afforded an additional 0.139 g of the product as a light yellow solid. The combined yield was 0.594 g (72%). ir (Kbr) $\nu_{max}$: 3345 (br, —GH), 1770 (β-lactam CO), 1680 (—CO$_2$PNB) cm$^{-1}$; $^1$Hnmr (d$_6$-

DMSO) δ: 8.98–7.96 (m, 4H, pyridinium aromatic), 8.20–7.65 (ABq, J=7.0 Hz, 4H, PNB aromatic), 5.53–4.80 (m, 4H), 4.3–3.7 (m, 2H), 3.6–3.25 (m, 6H), 2.66 (s, 3H, S-Me), 1.16 (d, J=6.0 Hz, 3H, CHMe).

C. (5R,6S)-3-[2-(3-methylthiopyridinio)ethyl thio]-6-[1-(R)-hydroxyethyl]-7-oxo-1-azabicyclo[3.2.0-]hept-2-ene-2-carboxylate

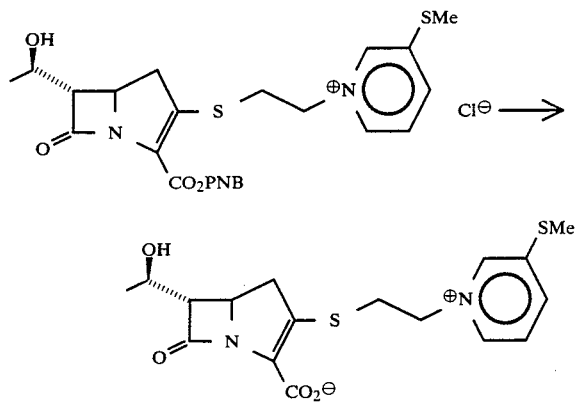

To a mixture of p-nitrobenzyl (5R,6S)-3-[2-(3-methyl-thiopyridinio)ethyl thio]-6-[1-(R)-hydroxyethyl]-7-oxo-1-azabicyclo[3.2.0]-hept-2-ene-2-carboxylate chloride (0.551 g, 1.0 mmol) and 10% palladium-on-charcoal (0.55 g) in 25 mL of phosphate buffer (0.05M, pH 7.4) was added 5 mL of THF and 25 mL of ether. This mixture was hydrogenated (Parr) at 40 psi for 1 h. The reaction mixture was then filtered through Celite and the filter cake was washed with H$_2$O and ether. The aqueous phase was separated and washed with additional ether (3×). After removing residual organic solvents in vacuo the aqueous solution was cooled at 0° C. and the pH was adjusted to 7.0 with saturated aqueous NaHCO$_3$. This solution was immediately applied to a C$_{18}$ reverse-phase column. Elution with H$_2$O and subsequent lyophilization of the relevant fractions afforded 0.25 g of a bright yellow solid. This material was repurified by reverse-phase hplc to give the product (0.210 g, 55%) as a light yellow solid. ir (KBr) ν$_{max}$: 3400 (br, —OH), 1755 (β-lactam CO), 1590 (—CO$_2$−) cm$^{-1}$; $^1$Hnmr (D$_2$O) δ: 8.60–7.76 (m, 4H, aromatic), 4.76 (t, J=5.8 Hz, N-CH$_2$), 4.13 (d of q, J=J′=6.3 Hz, 1H, H-1′), 3.95 (d of t, J=9.0 Hz, J′=2.8 Hz, 1H, H-5), 3.45–2.75 (m, 5H), 2.59 (s, 3H, S-Me), 1.20 (d, J=6.4 Hz, 3H, CHMe); uv (H$_2$O) λ$_{max}$: 296 (ε8509), 273 (ε13005), 231 (ε11576) nm; t$_½$ (pH 7.4, 36.8° C.) 20 h.

EXAMPLE 12

Preparation of 3-[2-(1-(2,6-dimethylpyridinium)ethylthio]-6α-[1-(R)-hydroxyethyl]-7-oxo-1-azabicyclo(3.2.0)hept-2-ene-2-carboxylate

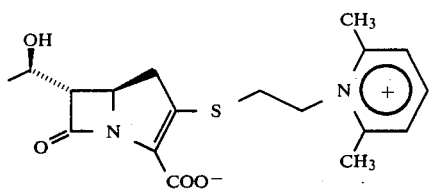

A. 1-(2-mercaptoethyl)-2,6-dimethylpyridinium methanesulfonate

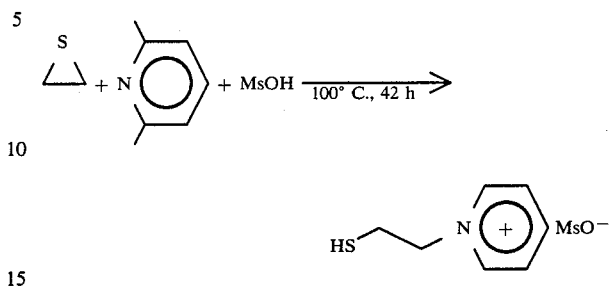

A mixture of 2,6-dimethylpyridine (19.2 mL, 0.165 mol) and methanesulfonic acid (3.27 mL, 0.050 mol) was stirred for 15 min, treated with ethylene sulfide (4.17 mL, 0.070 mol) and stirred at 100° C. for 42 h under a nitrogen atmosphere. After cooling to 25° C., the reaction mixture was diluted with ether (45 mL) and water (30 mL). The two layers were separated and the organic layer was extracted with water (2×5 mL). The aqueous layers were combined, filtered through a Celite pad, washed with ether (2×15 mL), pumped to remove the traces of organic solvents and poured on top of a column (3.0×12 cm) of μ-bondapak C-18. Elution with 3% acetonitrile 97% water mixture gave after lyophilization of the appropriate fractions 2.5 g of the impure title compound as a syrup. It was repurified by hplc (μ-bondapak C-18) to give 0.90 g (7%) of the title compound. ir (film) ν$_{max}$: 2520 (SH), 1640 and 1625 (pyridinium), 1585, 1490, 1200 cm$^{-1}$ (sulfonate), $^1$Hmr (DMSO-d$_6$+D$_2$O) δ: 2.36 (3H, s, CH$_3$SO$_3$−), 4.62 (2H, m, CH$_2$N+), 7.74 (2H, m, Hm of pyridinium), 8.24 (1H, m, Hp of pyridinium), uv (H$_2$O) $_{max}$: 272 (4080)mμ.

B. Paranitrobenzyl 3-[2-(1-(2,6-dimethylpyridinium)ethylthio]-6α-[1-(R)-hydroxyethyl]-7-oxo-1-azabicyclo(3.2.0)hept-2-ene-carboxylate diphenylphosphate

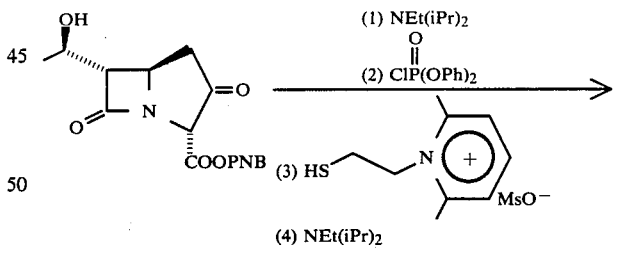

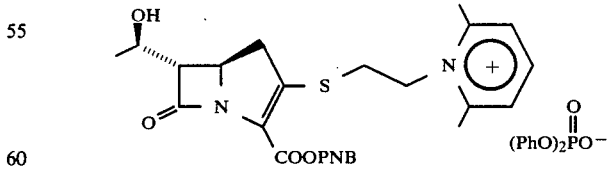

To a cold (0° C.) solution of p-nitrobenzyl 6α-[1-(R)-hydroxyethyl]-3,7-dioxo-1-azabicyclo(3.2.0)hept-2-ene-2-carboxylate (0.658 g, 1.89 mmol) in acetonitrile (6 mL) kept under a nitrogen atmosphere was added diisopropylethylamine (0.394 mL, 2.26 mmol) and diphenyl chlorophosphate (0.468 mL, 2.26 mmol). The reaction mixture was stirred 30 min and treated with a solution of 1-(2-mercaptoethyl)-2,6-dimethylpyridinium methanesulfonate (0.720 g, 2.73 mmol) in acetonitrile (3 mL) followed by diisopropylethylamine (0.394 mL, 2.26 mmol). The reaction mixture was stirred at 0° C. for 2 h, diluted with cold (0° C.) water (27 mL) and poured on top of a column (2.5×9.0 cm) of μ-bondapak C-18. Elution with acetonitrile-water mixtures and lyophylization of the appropriate fractions gave 0.92 g (65%) of the title compound, ir (KBr) $\nu_{max}$: 3700–3000 (OH), 1765 (C=O of β-lactam), 1690 (C=O of PNB ester), 1620 (pyridinium), 1590 (phenyl), 1517 ($NO_2$), 1330 ($NO_2$), 880 cm$^{-1}$ ($NO_2$), $^1$Hmr (DMSO, d$_6$) δ: 1.15 (3H, d, J=6.2 Hz, $CH_3$CHOH), 2.7–3.7 (11H, $CH_2$S, 2-$CH_3$ on pyridinium, H-4, H-6), 3.7–4.4 (2H, $CH_3CHOH$, H-5), 4.7 (2H, m, $CH_2N^+$), 5.14 (1H, d, J=4.5 Hz, OH), 5.37 (center of ABq, J=13.2 Hz, $CH_2$ of PNB), 6.7–7.5 (10H, m, phenyl), 7.5–8.7 (7H, pyridinium, H's of PNB), uv ($H_2O$) $\lambda_{max}$: 274 (ε14150), 319 (ε9445) mμ

C.
3-[2-(1-(2,6-dimethylpyridinium))ethylthio]-6α-[1-(R)-hydroxyethyl]-7-oxo-1-azabicyclo(3.2.0)hept-2-ene-2-carboxylate

EXAMPLE 13

Preparation of (5R, 6S)-3-[2-(2-methylthio-3-methylimidazolio)ethyl-thio]-6-[1-(R)-hydroxyethyl]-7-oxo-1-azabicyclo[3.2.0]hept-2-ene-2-carboxylate

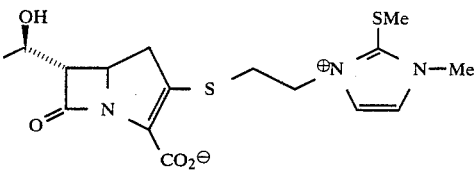

A.
2-Methylthio-3-methyl-1-(2-mercaptoethyl-)imidazolium trifluoromethanesulfonate

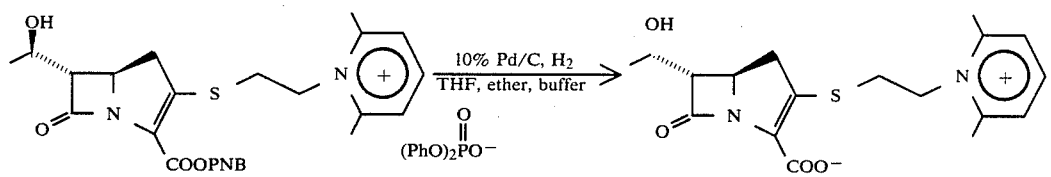

To a solution of p-nitrobenzyl 3-[2-(1-(2,6-dimethylpyridinium))ethylthio]-6α-[1-(R)-hydroxyethyl]-7-oxo-1-azabicyclo(3.2.0)hept-2-ene-2-carboxylate diphenylphosphate (0.80 g, 1.07 mmol) in wet tetrahydrofuran (42 mL) was added ether (42 mL), potassium phosphate monobasic-sodium hydroxide buffer (0.15M, pH 7.22, 21 mL) and 10% palladium on charcoal (0.80 g). The resulting mixture was hydrogenated for 1 h under 40 psi at 23° C. and filtered through a Celite pad. The two layers were separated and the organic layer was extracted with the buffer (3×8 mL). The aqueous phase were combined, washed with ether (50 mL), pumped to remove traces of organic solvent and poured on top of a column (3.0×10.2 cm) of μ-bondapak C-18. Elution of the column with 5% acetonitrile-95% water mixture and lyophylization of the appropriate fractions gave the title compound 0.246 g (63%) as a yellowish powder, ir (KBr) $\nu_{max}$: 3700–2800 (OH), 1750 (C=O of the β-lactam), 1620 (pyridinium), 1585 cm$^{-1}$ (carboxylate), $^1$Hmr ($D_2O$) δ: 1.23 (3H, d, J=6.4 Hz, $CH_3CHOH$), 2.5–3.5 (11H, H-4, H-6, $CH_2$S, 2$CH_3$ on pyridinium), 3.8–4.4 (2H, $CH_3CHOH$, H-5), 4.5–4.9 ($CH_2N^+$, HOD), 7.64 and 7.74 (2H, A part of $A_2B$ system, Hm of pyridinium), 8.07, 8.16, 8.18 and 8.27 (1H, B part of $A_2B$ system, Hp of pyridinium), uv ($H_2O$) $\lambda_{max}$: 277 (ε9733), 300 (ε8271) mμ, $[\alpha]_D^{23}$ +50.7° (C 0.48, $H_2O$), Anal. calcd. for $C_{18}H_{22}N_2O_4S \cdot 1.5H_2O$: C 55.51, H 6.47, N 7.19; found: C 55.14, H 6.23, N 6.46.

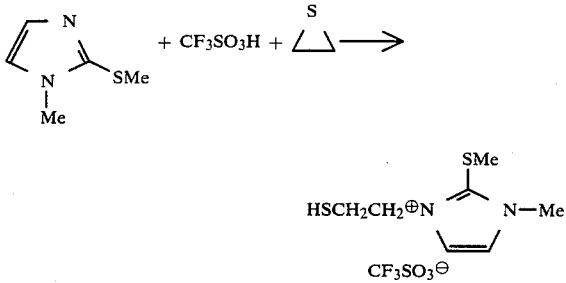

Trifluoromethanesulfonic acid (1.38 mL, 0.015 mol) was added dropwise to 2-methylthio-1-methylimidazole[1] (4.0 g, 0.03 mol) at 0° C. under $N_2$. Ethylene sulfide (0.9 mL, 0.015 mol) was then added and the mixture was heated at 55° C. under $N_2$ for 24 h. The reaction mixture was triturated with ether (3x) and the residue was taken up in acetone, filtered and evaporated. This gave the product (4.2 g, 82%) as a semicrystalline solid which was used as such without further purification. ir(film) $\nu_{max}$: 2550 (w, sh) cm$^{-1}$; 'Hnmr (d$_6$-acetone) δ: 7.97 (s, 2H), 4.66 (t, J=7 Hz, 2H, methylene), 4.17 (s, 3H, N-Me), 3.20 (d of t, J=7 Hz, J'=9 Hz, 2H, methylene), 2.72 (s, 3H, S-Me), 2.20 (t, J=9 Hz, 1H, —SH).

[1]. Prepared as per A. Wohl and W. Marckwald, Chem. Ber. 22, 1353 (1889).

B. p-Nitrobenzyl (5R, 6S)-3-[2-(2-methylthio-3-methylimidazolio)ethyl thio]-6-[1-(R)-hydroxyethyl]-7-oxo-1-azabicyclo[3.2.0-]hept-2-ene-2-carboxylate diphenylphosphate

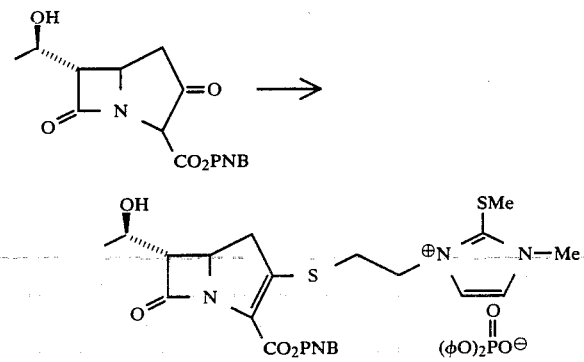

To a solution of p-nitrobenzyl (5R, 6S)-6-[1-(R)-hydroxyethyl]-3,7-dioxo-1-azabicyclo[3.2.0]heptane-2-carboxylate (1.40 g, 4.0 mmol) in 50 mL of dry acetonitrile, at 0° C. under $N_2$, was added dropwise diisopropylethylamine (0.76 mL, 4.4 mmol) followed by diphenyl chlorophosphate (0.91 mL, 4.1 mmol). After stirring the reaction mixture at room temperature for 1 h, diisopropylethylamine (0.76 mL, 4.4 mmol) was added and then a solution of 2-methylthio-3-methyl-1-(2-mercaptoethyl)imidazolium trifluoromethanesulfonate (2.0 g, 5.9 mmol) in 5 mL of acetonitrile was added dropwise. The reaction mixture was kept at room temperature for 1.5 h and was then concentrated in vacuo to give a gum. This gum was taken up in $H_2O$ and applied to a $C_{18}$ reverse-phase column. Elution with $H_2O$, then 20% acetonitrile-$H_2O$ and finally 30% acetonitrile-$H_2O$, followed by lyophilization of the appropriate fractions afforded the product (0.90 g, 30%) as a light yellow solid. ir(KBr) $\nu_{max}$: 3380 (br, OH), 1770 ($\beta$-lactam CO) cm$^{-1}$; 'Hnmr (d$_6$-acetone) $\delta$: 8.35 (br s, 1H), 8.24, 7.78 (AB q, J=8.8 Hz, 4H, aromatic), 7.89 (br s, 1H), 7.25-6.91 (m, 10H, diphenylphosphate), 5.50, 5.25 (AB$_q$, J=12 Hz, 2H, benzylic), 4.75-4.27 (m, 3H), 4.03 (s, 3H, N-Me), 4.15-2.75 (m, 8H), 2.53 (s, 3H, S-Me), 1.22 (d, J=6.2 Hz, 3H, —CHMe).

C. (5R, 6S)-3-[2-(2-Methylthio-3-methylimidazolio)ethylthio]-6-[1-(R)-hydroxyethyl]-7-oxo-1-azabicyclo[3.2.0]hept-2-ene-2-carboxylate

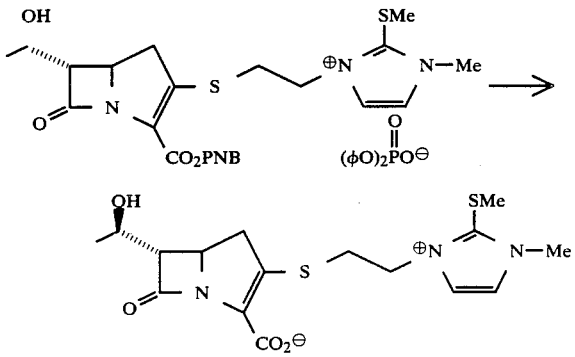

To a solution of p-nitrobenzyl (5R, 6S)-3-[2-(2-methylthio-3-methylimidazolio)ethyl thio]-6-[1-(R)-hydroxyethyl]-7-oxo-1-azabicyclo[3.2.0]hept-2-ene-2-carboxylate diphenylphosphate (1.20 g, 1.56 mmol) in a mixture of 70 mL of THF, 70 ml of ether and 31 mL of phosphate buffer (0.05M, pH 7.4) was added 1.2 g of 10% palladium-on-charcoal. This mixture was hydrogenated (Parr) at 35 psi for 55 min. The reaction mixture was then filtered through Celite and the filter cake was washed with $H_2O$ and ether. The aqueous phase was separated, cooled at 0° C. and the pH was adjusted to 7.0 with saturated aqueous NaHCO$_3$. After removing residual organic solvents in vacuo the aqueous solution was applied to a $C_{18}$ reverse-phase column. Elution with $H_2O$ and then 8% acetonitrile-$H_2O$ and subsequent lyophilization of the relevant fractions gave 0.25 g of a solid. This material was repurified by reverse-phase hplc to give the product (0.114 g, 19%) as an off-white solid. ir(KRr) $\nu_{max}$: 3420 (OH), 1750 ($\beta$-lactam CO), 1590 (—CO$_2\ominus$) cm$^{-1}$; 'Hnmr (D$_2$O) $\delta$: 7.58 (s, 2H), 4.52 (t, J=6 Hz, 2H), 4.28-3.82 (m, 2H), 3.90 (s, 3H, n-ME), 3.40-2.87 (m, 5H), 2.40 (s, 3H, S-Me), 1.20 (d, J=6.4 Hz, 3H, —CHMe); uv (H$_2$O) $\lambda_{max}$: 297 ($\epsilon$7572), 262 ($\epsilon$6259), 222 ($\epsilon$7955) nm.

EXAMPLE 14

Preparation of (5R, 6S)-3-[2-(3-aminopyridinio)ethylthio]-6-[1-(R)-hydroxyethyl]-7-oxo-1-azabicyclo[3.2.0]-hept-2-ene-2-carboxylate

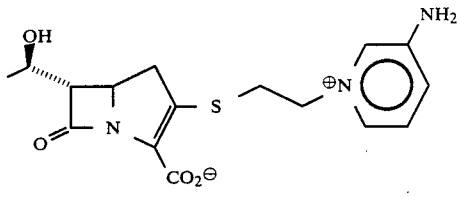

A. 3-Amino-1-(2-mercaptoethyl)pyridinium chloride

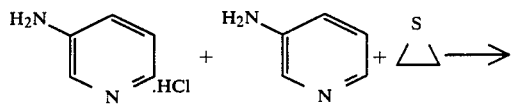

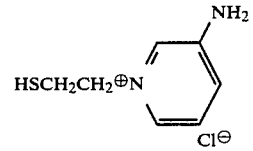

3-Aminopyridine (1.50 g, 0.016 mmol) was taken up in 15 mL of 1N methanolic HCl and the resulting solution was evaporated to give the hydrochloride as an oil. To this oil was added 3-aminopyridine (1.32 g, 0.015 mmol) and ethylene sulfide (0.89 ml, 0.015 mmol) and the resulting mixture was heated (oil bath) at 60°-65° C. under $N_2$ for 2 h. Another equivalent of ethylene sulfide (0.89 ml, 0.015 mmol) was added and heating was continued at 55°-65° C. for 65 h. The reaction mixture was washed with CH$_2$Cl$_2$ and then taken up in H$_2$O (25 ml). The aqueous solution was applied to a $C_{18}$ reverse-phase column which was eluted with H$_2$O. Evaporation of the relevant fractions gave the product (1.26 g, 44%) as a colorless, viscous oil. ir(film) $\nu_{max}$: 3180 (NH$_2$) cm$^{-1}$;

'Hnmr (d6-DMSO) δ: 8.19-7.59 (m, 4H, aromatic), 4.59 (t, J=6.2 Hz, 2H, N-CH2), 3.5 (brs, 2H, —NH2), 3.20-2.77 (m, 3H).

B. p-Nitrobenzyl (5R, 6S)-3-(2-(3-aminopyridinio)ethylthio)-6-(1-(R)-hydroxyethyl)-7-oxo-1-azabicyclo(3.2.0)hept-2-ene-2-carboxylate dihenylphosphate

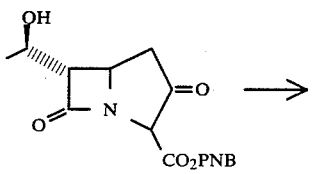

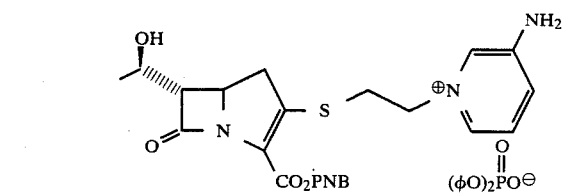

To a solution of p-nitrobenzyl (5R, 6S)-6-(1-(R)-hydroxyethyl)-3,7-dioxo-1-azabicyclo(3.2.0)heptane-2-carboxylate (0.696 g, 2.0 mmol) in 10 mL of dry acetonitrile, at 0° C. under N2, was added dropwise diisopyropylethylamine (0.382 mL, 2.2 mmol) followed by diphenyl chlorophosphate (0.457 mL, 2.2 mmol). After stirring at 0° C. for 30 min. a solution of 3-amino-1-(2-mercaptoethyl)pyridinium chloride (0.475 g, 2.5 mmol) in 1 ml of dry DMF was added, followed by additional diisopropylethylamine (0.435 mL, 2.5 mmol). The reaction mixture was kept at 0° C. for 1.5 h and was then concentrated in vacuo. The resulting gum was taken up in acetonitrile-H2O (1:1) and applied to a C18 reverse-phase column. Elution with H2O, followed by 20% acetonitrile-H2O and subsequent lyophilization of the relevant fractions afforded the product (0.730 g, 50%) as a beige-colored solid. ir(KBr) νmax: 3330 (br, OH), 3180 (br, NH2), 1770 (β-lactam CO), 1690 (—CO2PNB)cm$^{-1}$; 'Hnmr (d6-DMSO) δ: 8.29-7.63 (m, 8H, aromatic), 7.2-6.7 (m, 10H, diphenylphosphate), 5.47, 5.18 (ABq, J=14 Hz, 2H, benzylic), 4.73-4.45 (m, 3H), 4.2-3.8 (m, 1H), 3.6-2.6 (m, 8H), 1.15 (d, J=6.2 Hz, 3H, CHMe).

C. (5R, 6S)-3-((2-(3-Aminopyridinio)ethyl)thio)-6-1-(R)-hydroxyethyl)-7-oxo-1-azabicyclo(3.2.0)hept-2-ene-2-carboxylate

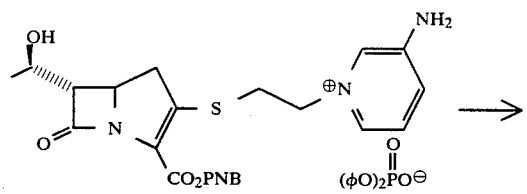

-continued

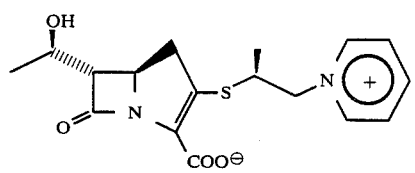

To a mixture of p-nitrobenzyl (5R, 6S)-3(2-(3-aminopyridinio)ethyl thio)-6-(1-(R)-hydroxyethyl)-7-oxo-1-azabicyclo(3.2.0)hept-2-ene-2-carboxylate diphenylphosphate (0.730 g, 1.0 mmol) and 10% palladium-on-charcoal (0.7 g) in 25 mL of a phosphate buffer (0.05 m, pH 7.4) was added 8 mL of THF and 20 mL of ether. This mixture was then hydrogenated (Parr) at 40 psi for 1 h. The resulting mixture was filtered through a pad of Celite and the filter cake was washed with H2O and ether. The aqueous phase was separated, washed with ether (2x) and then residual volatiles were removed in vacuo. The aqueous solution was immediately applied to a C18 reverse-phase column which was eluted with H2O. Lyophilization of the relevant fractions afforded 0.45 g of an off-white solid. This material was repurified by reverse-phase hplc to give the desired product (0.123 g, 35%) as an ivory-colored solid.

ir(KBr) νmax: 3340 (br), 1750 (br, β-lactam CO), 1580 (br, —CO2⊖) cm$^{-1}$; 'Hnmr (D2O) δ: 8.07-7.59 (m, 4H, aromatic), 4.61 (t, J=5.8 Hz, 2H, N-CH2), 4.14 (d of q, J=J'=6.3 Hz, 1H, H-1'), 3.97 (d of t, J=9.2 Hz, J'=2.6 Hz, 1H, H-5), 3.38 (t, J=5.8 Hz, 2H, S-CH2), 3.24 (d of d, J=6.0 Hz, J'=2.6 Hz, 1H, H-6), 3.17-2.57 (m, 2H, H-4), 1.21 (d, J=6.3 Hz, 3H, CHMe); uv(H2O) λmax: 299 (ε7949), 256 (ε8822) nm; t½ (pH 7.4, 36.8° C.) 18.5 h.

EXAMPLE 15

PREPARATION OF

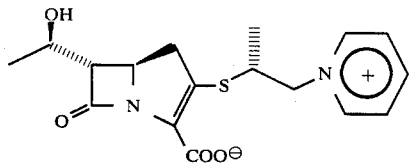

(5R,6S)3-[1-(S)-methyl-2-(1-pyridinium)ethylthio]-6-[1-(R)-hydroxyethyl]-7-oxo-1-azabicyclo(3.2.0)hept-2-ene-2-carboxylate and

(5R,6S)-3-[1-(R)-methyl-2-(1-pyridinium)ethylthio]-6-[1-(R)-hydroxyethyl]-7-oxo-1-azabicyclo(3.2.0)hept-2-ene-2-carboxylate

A. dl-1-(2-mercapto-2-methylethyl)pyridinium methanesulfonate
dl-1-(2-mercapto-1-methylethyl)pyridinium methanesulfonate

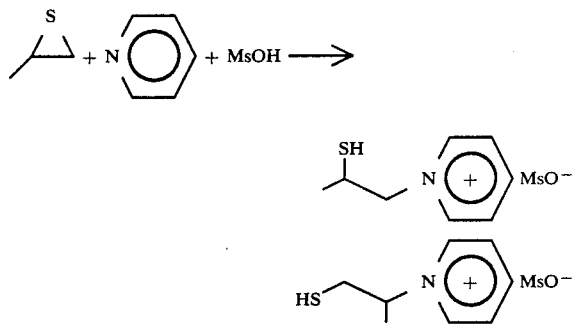

Methanesulfonic acid (1.95 mL, 0.030 mol) was added slowly to cold pyridine (7.83 mL, 0.097 mol) and the resulting mixture was stirred at 40° C. for 15 min, treated with dl-propylenesulfide (2.59 mL, 0.033 mol) and stirred at 60° C. under a nitrogen atmosphere for 90 h. Pyridine was removed under vacuum; the residue was mixed with water and purified by chromatography (hplc, Prep. Bondapak C-18). The appropriate fractions were combined and lyophilized giving dl-1-(2-mercapto-2-methylethyl)pyridinium methanesulfonate 1.14 g (15%) as a colorless syrup; ir (film) $\nu_{max}$: 2520 (SH), 1640 (pyridinium), 1180 (s, $CH_3SO_3^-$), 1040 ($CH_3SO_3^-$)cm$^{-1}$, $^1$Hmr (DMSO d$_6$) δ: 1.35 (d, J=6.8 Hz, 3H, $CH_3CHS$), 2.30 (s, 3H, $CH_3SO_3^-$), 2.90 (d, J=8.5 Hz, 1H, SH), 3.2-3.7 (m, CHSH), 4.52 (dd, $J_{gem}$=12.9 Hz, J=8.4 Hz, $CHCH_2N^+$), 4.87 (dd, $J_{gem}$=12.9 Hz, J=6.0 Hz, $CHCH_2N^+$), 8.0-8.4 (m, 2H, Hm of pyridinium), 8.5-8.8 (m, 1H, Hp of pyridinium), 9.04 (dd, J=1.4 Hz, J=6.7 Hz, 2H, Ho of pyridinium), uv (H$_2$O) λ$_{max}$: 208 (ε5267), 259 (ε3338), Anal. calcd. for $C_9H_{15}NO_3S_2.2H_2O$; C 37.88, H 6.71, N 4.91, S 22.47; found: C 37.49, H 6.85, N 4.86, S 22.09 and dl-1-(2-mercapto-1-methylethyl) pyridinium methanesulfonate 0.82 g (11%) as a colourless syrup: ir (film) $\nu_{max}$: 2500 (SH), 1628 (pyridinium), 1180 (sulfonate, 1035 (sulfonate) cm$^{-1}$, $^1$Hmr (DMSO d$_6$) δ: 1.69 (d, J=6.8 Hz, 3H, $CH_3CHN^{30}$), 2.31 (s, 3H, $CH_3SO_3^-$), 3.0-3.3 (m, 2H, $CH_2S$), 4.2-5.2 (m, 1H, CHN$^+$), 8.0-8.4 (m, 2H, Hm of pyridinium), 8.5-8.8 (m, 1H, Hp of pyridinium), 9.0-9.2 (m, 2H, Ho of pyridinium), uv (H$_2$O) λ$_{max}$: 209 (ε4987), 258 (ε3838). Anal. calcd. for $C_9H_{15}NO_3S_2.1.5H_2O$: C 39.11, H 6.56, N, 5.07; found: C 39.13, H, 5.92, N 5.20.

B. (5R,6S) paranitrobenzyl 3-[1-(R,S)methyl-2-(1-pyridinium)ethylthio]-6-[1-(R)-hydroxyethyl]-7-oxo-1-azabicyclo(3.2.0)hept-2-ene-2-carboxylate diphenylphosphate

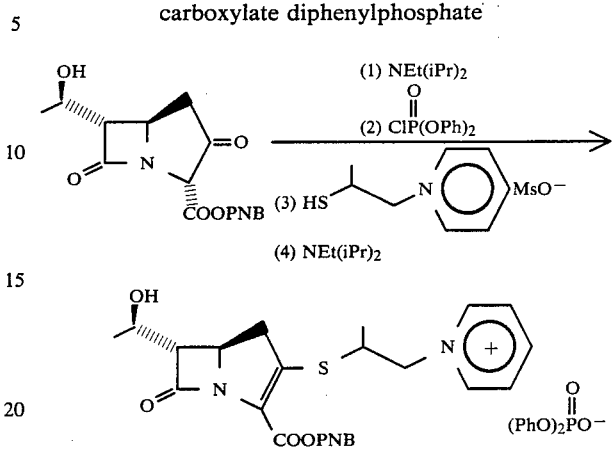

To a cold (0° C.) solution of (5R,6S)paranitrobenzyl-6-[1-(R)-hydroxyethyl]-3,7-dioxo-1-azabicyclo(3.2.0)hept-2-ene-2-carboxylate (0.523 g, 1.5 mmol) in acetonitrile (6 mL) kept under a nitrogen atmosphere was added diisopropylethylamine (0.314 mL, 1.8 mmol) followed by diphenyl chlorophosphate (0.373 mL, 1.8 mmol). The reaction mixture was stirred for 30 min and treated with a solution of dl-1-(2-mercapto-2-methylethyl)pyridinium methanesulfonate (0.539 g, 2.16 mmol) in acetonitrile (2 mL) and diisopropylethylamine (0.314 mL, 1.8 mmol). The reaction mixture was stirred at 0° C. for 1 h, diluted with cold (0° C.) water (24 mL) and chromatographed over prep bondapak C-18 column (2.5×8.5 cm) with 25–50% acetonitrile in water as eluting solvents to give 1.07 g (97%) of the title compound as a yellowish powder after lyophilization; ir (KBr) $\nu_{max}$: 3700-3100 (OH), 1770 (C=O of β-lactam), 1695 (C=O of PNB ester), 1630 (pyridinium), 1590 (phenyl), 1518 (NO$_2$), 1348 (NO$_2$), 885 (NO$_2$) cm$^{-1}$, $^1$Hmr (DMSO d$_6$) δ: 1.14 (d, J=6.1 Hz, 3H, $CH_3CHO$), 1.33 (d, J=6.3 Hz, 3H, $CH_3CHS$), 4.6-5.0 (m, $CH_2N^+$), 5.14 (d, J=5.2 Hz, 1H, OH), 5.37 (center of ABq, J=12.4 Hz, 2H, $CH_2$ of PNB), 6.6-7.5 (m, 10H, phenyl of phosphate), 7.69 (d, J=8.7 Hz, 2H, Ho of PNB), 8.0-8.4 (m, 4H, Hm of PNB, Hm of pyridinium), 8.4-8.8 -(m, 1H, Hp of pyridinium), 9.08 (d, J=5.6 Hz, 2H, Ho of pyridinium), uv (H$_2$O) λ$_{max}$: 263 (ε13325), 308 (ε8915). Anal. calcd. for $C_{36}H_{36}N_3O_{10}SP.H_2O$: C57.52, H 5.10, H 5.10, N 5.59, S 4.27; found: C 57.76, H 4.96, N 5.36, S 4.35.

C. (5R,6S)3-[1-(R and S)-methyl-2-(1-pyridinium)ethylthio]-6-[1-(R)-hydroxyethyl]-7-oxo-1-azabicyclo(3.2.0)hept-2-ene-2-carboxylate

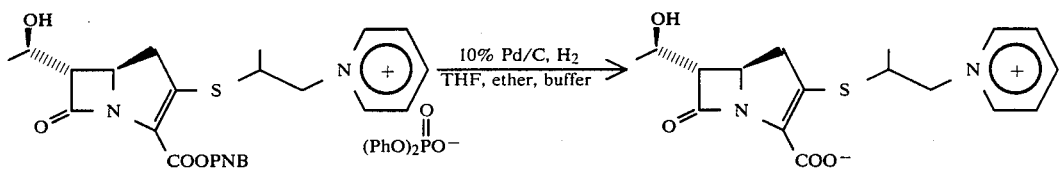

To a solution of (5R,6S)paranitrobenzyl 3-[1-(R,S)methyl-2-(1-pyridinium)ethylthio]-6-[1-(R)- hydroxyethyl]-7-oxo-1-azabicyclo(3.2.0)hept-2-ene-2-carboxylate diphenylphosphate (0.60 g, 0.82 mmol) in wet tetrahydrofuran (33 mL) was added ether (33 mL), potassium phosphate mono basic-sodium hydroxide buffer (17 mL, 0.15N, pH 7.22) and 10% palladium on charcoal (0.60 g). The resulting mixture was hydrogenated for 1 h under 40 psi at 23° C. The two layers were separated and the organic layer was extracted with water (3×7 mL). The aqueous layers were combined, filtered through a Celite pad, washed with ether (3×20 mL) and chromatographed on prep bondapak C-18 column (2.5×9.5 cm) with water as eluting solvent to give 0.18 g (63%) of mixture of diastereoisomers. The two diastereoisomers were separated by hplc (prep bondapak C-18) with water as eluting solvent: isomer with lower retention time, 0.068 g (23%) compound "B", ir (KBr) $\nu_{max}$: 1770 (C=O of β-lactam), 1633 (pyridinium), 1593 (carboxylate)cm$^{-1}$, $^1$Hmr (D$_2$O) δ: 1.20 (d, J=6.3 Hz, 3H, C$\underline{H}_3$CHO), 1.42 (d, J=6.9 Hz, 3H, C$\underline{H}_3$CHS), 2.3-3.2 (m, 3H, H-4, H-6), 3.5-3.9 (m, 1H, SCH), 3.9-4.2 (m, 2H, H-5, CH$_3$C$\underline{H}$O), 4.3-5.1 (m, CH$_2$N$^+$), 7.8-8.2 (m, 2H, Hm of pyridinium), 8.4-8.7 (m, 1H, Hp of pyridinium), 8.7-9.0 (m, 2H, Ho of pyridinium), uv (H$_2$O) $\lambda_{max}$: 260 (ε6727), 300 (ε8245), [α]$_D^{23}$-39.3° (c, H$_2$O), $\tau_{\frac{1}{2}}$=12.6 h (measured at a concentration of 10$^{-4}$M in phosphate buffer pH 7.4 at 36.8° C.); isomer with higher retention time, 0.081 g (28%), compound "A", ir (KBr) $\nu_{max}$: 1755 (C=O of β-lactam), 1630 (pyridinium), 1590 (carboxylate) cm$^{-1}$, $^1$Hmr (D$_2$O) δ: 1.18 (d, J=6.3 Hz, 3H, C$\underline{H}_3$CHO), 1.40 (d, J=7.0 Hz, 3H, C$\underline{H}_3$CHS), 2.84 (d, J=9.3 Hz, 2H, H-4), 3.26 (dd, J=2.7 Hz, J=5.9 Hz, 1H, H-6), 3.4-4.2 (m, 3H, SCH, CH$_3$C$\underline{H}$O, H-5), 4.2-5.1 (m, CH$_2$N$^+$), 7.7-8.1 (m, 2H, Hm of pyridinium), 8.3-8.65 (m, 1H, Hp of pyridinium), 8.65-8.9 (m, 2H, Ho of pyridinium), uv (H$_2$O) $\lambda_{max}$: 259 (ε5694), 296 (ε6936), [α]$_D^{23}$ +96.9° (c 0.56, H$_2$O), $\tau_{\frac{1}{2}}$=15.6 h (measured at a concentration of 10$^{-4}$M in phosphate buffer pH 7.4 at 36.8° C.).

EXAMPLE 16

PREPARATION OF

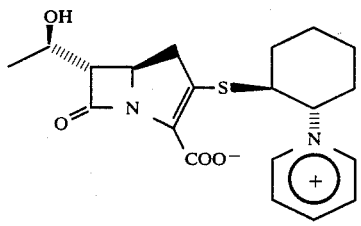

(5R,6S)3-[2-[(S)-(1-pyridinium)]-1-(S)-cyclohexylthio]-6-[1-(R)-hydroxyethyl]-7-oxo-1-azabicyclo(3.2.0)hept-2-ene-2-carboxylate and

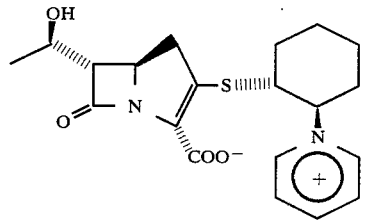

(5R,6S)3-[2-[(R)-(1-pyridinium)]-1-(R)-cyclohexylthio]-6-[1-(R)-hydroxyethyl]-7-oxo-1-azabicyclo(3.2.0)hept-2-ene-2-carboxylate.

A. dl-1-[2-mercapto-1-cyclohexyl]pyridinium methanesulfonate

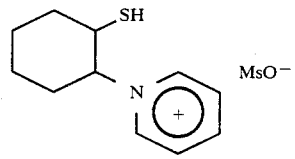

Methanesulfonic acid (0.65 mL, 0.01 mol) was added dropwise to pyridine (2.42 mL, 0.03 mol) with cooling. The mixture was stirred under a nitrogen atmosphere for 10 min, treated with dl-cyclohexenesulfide [1.377 g (85% pure), 0.0102 mol] and stirred at 72° C. for 25 h. The excess of pyridine was removed under vacuum and the traces were codistilled with water. The residue was mixed with water and chromatographed through prep-bondapak C-18 column (5×13 cm) with 0-2% acetonitrile in water as eluting solvent giving after lyophilization a colourless syrup 1.57 g (53%), ir (film) $\nu_{max}$: 2500 (SH), 1625 (pyridinium), 1190 (SO$_3^-$), $^1$Hmr (DMSO d$_6$) δ: 1.2-2.5 (m, 8H, cyclohexyl H), 2.32 (s, 3H, CH$_3$SO$_3^-$), 2.82 (d, J=9.8 Hz, SH), 3.0-3.5 (m, 1H, CHSH), 4.2-4.9 (m, 1H, CHN$^+$), 8.0-8.3 (m, 2H, Hm of pyridinium), 8.4-8.8 (m, 1H, Hp of pyridinium), 8.9-9.3 (m, 2H, Ho of pyridinium), uv (H$_2$O) $\lambda_{max}$: 214 (ε5365), 258 (ε3500). Anal. calcd. for C$_{12}$H$_{19}$NO$_3$S$_2$.H$_2$O: C 46.88, H 6.88, N 4.56; found: C 46.61, H 6.46, N 4.65.

B. (5R,6S)paranitrobenzyl 3-[2-[(R or S)-(1-pyridinium)]-1-(R or S)-cyclohexylthio]-6-(1-(R)-hydroxyethyl]-7-oxo-1-azabicyclo(3.2.0)hept-2-ene-2-carboxylate diphenylphosphate

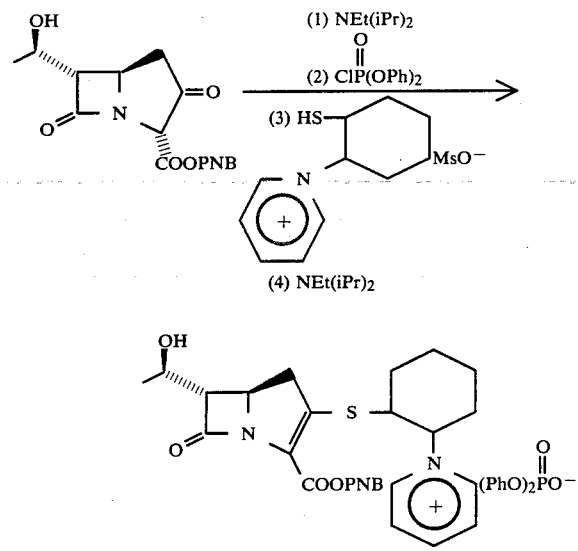

To a cold (0° C.) solution of (5R,6S)paranitrobenzyl 6-[1-(R)-hydroxyethyl]-3,7-dioxo-1-azabicyclo(3.2.0-)hept-2-ene-2-carboxylate (1.37 g, 3.93 mmol) in acetonitrile (15 mL) kept under a nitrogein atmosphere was added diisopropylethylamine (0.822 mL, 4.7 mmol) and diphenyl chlorophosphate (0.979 mL, 4.7 mmol). The resulting solution was stirred for 30 min and treated with a solution of dl-1-(2-mercapto-1-cyclohexyl)-pyridinium methanesulfonate (1.64 g, 5.66 mmol) in acetonitrile (4.7 mL) followed by diisopropylethylamine (0.822 mL, 4.7 mmol). The reaction mixture was stirred at 0° C. for 1 h, diluted with cold (0° C.) water (75 mL) and chromatographed on prepbondapak C-18 with 25–50% acetonitrile in water as eluting solvent giving after lyophilization of the appropriate fractions 1.9 g (35%) of the title compound, ir (KBr) $\nu_{max}$: 3700–3000 (OH), 1770 (C=O of β-lactam), 1700 (C=O of PNB ester), 1628 (pyridinium), 1590 (phenyl), 1515 ($NO_2$), 1345 ($NO_2$), 880 ($NO_2$) $cm^{-1}$, $^1$Hmr ($D_2O$) δ: 1.13 (d, J=6.1 Hz, 3H, C$\underline{H}_3$CHO), 1.25–2.5 (m, 8H, cyclohexyl H), 2.7–3.5 (m, 4H, H-4, H-6, CHS), 3.5–4.4 (m, 2H, CH$_3$C$\underline{H}$O , H-5), 4.4–5.0 (m, 1H, CHN+), 5.30 (center of ABq, J=12.8 Hz, $CH_2$ of PNB), 6.7–7.4 (m, 10H, phenyl), 7.65 (d, J=8.6 Hz, 2H, Ho of PNB), 7.9–8.4 (m, 4H, Hm of PNB, Hm of pyridinium), 8.4–8.8 (m, 1H, Hp of pyridinium), 9.0–9.4 (m, 2H, Ho of pyridinium), uv ($H_2O$) $\lambda_{max}$: 263 (ϵ9038), 309 (ϵ6394). Anal. calcd for $C_{39}H_{40}N_3O_{10}SP \cdot H_2O$: C 59.16, H, 5.35, N, 5.31; found: C 58.95, H 5.15, N 5.57.

C. (5R,6S) 3-[2-[(R or S)-(1-pyridinium)-1-(R or S)-cyclohexylthio]-6-[1-(R)-hydroxyethyl]-7-oxo-1-azabicyclo(3.2.0)hept-2-ene-2-carboxylate

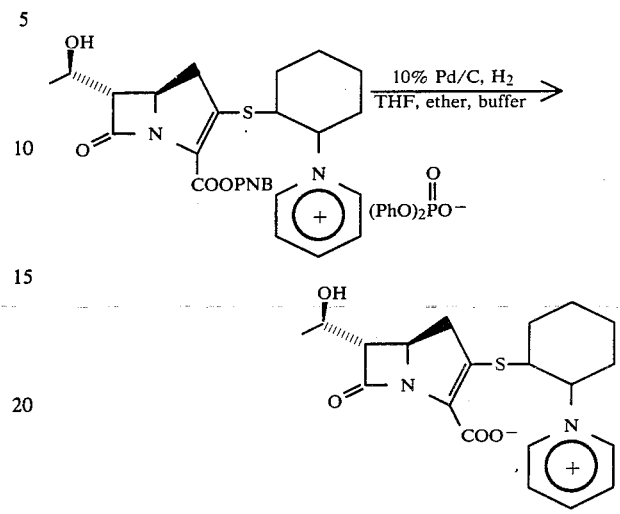

To a solution of (5R,6S) paranitrobenzyl 3-[2-[(R or S)-(1-pyridinium)-1-(R or S)-cyclohexylthio]-6-[1-(R)-hydroxyethyl]-7-oxo-1-azabicyclo(3.2.0)hept-2-ene-2-carboxylate diphenylphosphate (1.85 g, 2.34 mmol) in wet tetrahydrofuran (96 mL) was added ether (96 mL), potassium phosphate monobasic-sodium hydroxide buffer (0.15M, pH 7.22, 50 mL) and 10% palladium on charcoal (1.9 g). The resulting mixture was hydrogenated at 23° under 40 psi for 1.25 h. The organic layer was separated and washed with water (3×20 mL). The aqueous solutions were filtered through a Celite pad, washed with ether (2×60 mL), pumped to remove the traces of organic solvents and chromatographed on prepbondapak C-18 column (4.5×9 cm) with 0–5% acetonitrile in water as eluting solvent giving after lyophilization 0.705 g (76%) of a mixture of diastereoisomers. The separation of the diastereoisomers was done by hplc (prepbondapak C-18) with 4% acetonitrile in water as eluting solvent; diastereoisomer with lower retention time, compound "A", (0.29 g, 31%), ir (KBr) $\nu_{max}$: 1750 (C=O of β-lactam), 1620 (sh, pyridinium), 1685 (carboxylate) $cm^{-1}$, $^1$Hmr ($D_2O$) δ: 1.21 (d, J=6.3 Hz, 3H, C$\underline{H}_3$CHO), 1.4–2.5 (m, 8H, cyclohexyl H), 2.5–3.05 (m, 2H, H-4), 3.05–3.25 (m, 1H, H-6), 3.3–3.7 (m, 1H, CHS), 3.9–4.3 (m, 2H, H-5, CH$_3$C$\underline{H}$O), 4.3–4.8 (m, CHN+), 7.8–8.2 (m, 2H, Hm of pyridinium), 8.3–8.7 (m, 1H, Hp of pyridinium), 8.8–9.1 (m, 2H, Ho of pyridinium), uv ($H_2O$) $\lambda_{max}$: 260 (ϵ7123), 300 (ϵ8685), $[\alpha]_D^{23}$ +6.2° (c 0.63, $H_2O$), $\tau_{\frac{1}{2}}$=16.6 h (measured at a concentration of $10^{-4}M$ in phosphate buffer pH 7.4 at 36.8° C.); Anal. calcd. for $C_{20}H_{24}N_2O_4S \cdot 2H_2O$: C 56.59, H 6.65, N 6.60, S 7.55; found: C 56.83, H 6.47, N 6.59, S 7.43; diastereoisomer with higher retention time, compound "B", (0.35 g, 38%) ir (KBr) $\nu_{max}$: 1750 (C=O of β-lactam), 1622 (sh, pyridinium), 1588 (carboxylate) $cm^{-1}$, $^1$Hmr ($D_2O$) δ: 1.19 (d, J=6.4 Hz, 3H, C$\underline{H}_3$CHO), 1.3–2.5 (m, 8H, cyclohexyl H), 2.5–3.1 (m, 2H, H-4), 3.1–3.3 (m, 1H, H-6), 3.3–3.8 (m, 2H, H-b 5, CHS), 4.1 (center of m, 1H, CH$_3$C$\underline{H}$O), 4.25–4.7 (m, 1H, CHN+), 7.8–8.1 (m, 2H, Hm of pyridinium), 8.3–8.7 (m, 1H, Hp of pyridinium), 8.75–9.0 (m, 2H, Ho of pyridinium), uv ($H_2O$) $\lambda_{max}$: 259 (ϵ5992), 296 (ϵ7646), $[\alpha]_D^{23}$ +65.3° (c 0.43, $H_2O$), $\tau_{\frac{1}{2}}$=20.2 H (measured at a concentration of $10^{-4}$M in phosphate buffer pH 7.4 at 36.8° C.).

EXAMPLE 17

B. (5R) 3-[(2-pyridinioethyl)thio]-(6S)-[(1R)-hydroxyethyl]-7-oxo-1-azabicyclo[3.2.0]hept-2-ene-2-carboxylate

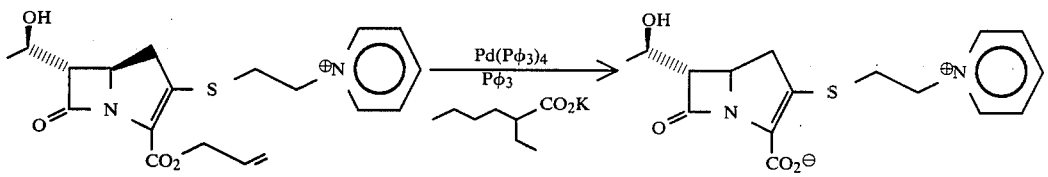

A. (5R) Allyl-3-[(2-pyridinioethyl)thio]-(6S)-[(1R)-hydroxyethyl]-7-oxo-1-azabicyclo[3.2.0]hept-2-ene-2-carboxylate diphenylphosphate

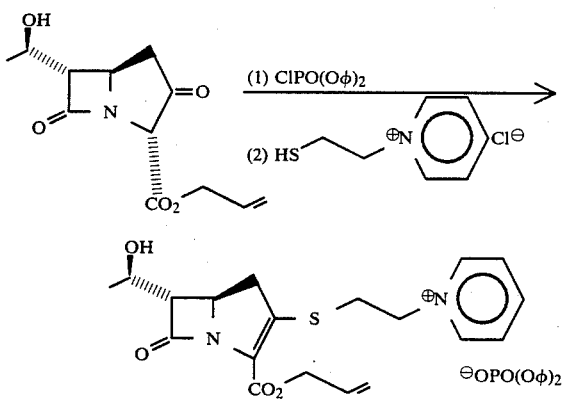

To a solution of (5R) allyl 3,7-dioxo-(6S)-[(1R)-hydroxyethyl]1-azabicyclo[3.2.0]heptane-(2R)-carboxylate (473 mg, 1.87 mmol) in CH$_3$CN (6 mL) was added at ca. $-10°$ C. under a nitrogen atmosphere diisopropylethylamine (0.42 mL, 2.4 mmol) followed by diphenyl chlorophosphate (0.50 mL, 2.4 mmol). The mixture was stirred at 0° C. for 30 min, and then cooled to $-15°$ C. To this was added an oily suspension of N-(2-mercaptoethyl)pyridinium chloride (527 mg, 3.00 mmol) in CH$_3$CN (1 mL) containing 5 drops of DMF, followed by diisopropylethylamine (0.42 mL, 2.4 mmol). The mixture was stirred at $-15°$ C. for 30 min and then diluted with H$_2$O (20 mL). This mixture was directly purified on a reverse phase silica gel (C$_{18}$ Prep-PAK, 12 g, Water Associates) eluting with H$_2$O (200 mL), 10% CH$_3$CN/H$_2$O (100 mL), 20% CH$_3$CN/H$_2$O (100 mL), 30% CH$_3$CN/H$_2$O (100 mL) and then 40% CH$_3$CN/H$_2$O (100 mL). Appropriate fractions were collected, the organic solvent removed by a vacuum pump and lyophilized to obtain 786 mg (1.26 mmol, y. 67.3) of the title compound as brownish powder: $^1$Hmr (DMSO-d$_6$, CFT-20) δ: 1.16 (3H, d, J=6 Hz, 1'-CH$_3$), 2.6–3.7 (m), 3.75–4.3 (2H, m, 5-H and 1'-H), 4.65 (2H, m, —CO$_2$CH$_2$—), 4.87 (2H, t, J=6 Hz, —CH$_2$—N+), 5–6.2 (3H, m, olefinic protons), 6.6–7.4 (m, aromatic protons), 8.15 (2H, "t", J≃7 Hz, aromatic protons meta to the nitrogen), 8.63 (1H, "t", J≃7 Hz, aromatic proton para to the nitrogen) and 9.07 ppm (2H, "d", J≃7 Hz, aromatic protons ortho to the nitrogen); ir (film) v: 3400 (OH), 1770 (β-lactam), 1690 (ester), 1625 (pyridinio).

To a solution of (5R) allyl 3-[(2-pyridinioethyl)thio]-(6R)-[(1R)-hydroxyethyl]-7-oxo-1-azabicyclo[3.2.0-]hept-2-ene-2-carboxylate diphenylphosphate (156 mg, 0.25 mmol) in CH$_3$CN (2 mL) was successively added at ca. 22° C. a solution of potassium 2-ethylhexanoate in EtOAc (0.5M, 0.6 mL; 0.3 mmol), triphenylphosphine (15 mg, 0.057 mmol) and tetrakistriphenylphosphine palladium (15 mg, 0.013 mmol). The mixture was stirred at ca. 22° C. under a nitrogen atmosphere for 2 h. After addition of anhydrous Et$_2$O (7 mL), the precipitate was filtered, washed with anhydrous Et$_2$O (7 mL) and dried in vacuo to yield 101 mg of brownish solid. This was purified by reverse phase column chromatography (C$_{18}$ PrepPAK, 12 g, Waters Associates) eluting with H$_2$O. Appropriate fractions (fr. 7–12, each 20 mL) were collected and lyophilized to obtain 53 mg (0.16 mmol, y. 64%) of the title compound as yellowish powder. This material was contaminated with potassium diphenylphosphate and potassium 2-ethylhexanoate: $^1$Hmr (D$_2$O, CFT-20) δ: 0.80 (t, J=6.4 Hz, Me from ethylhexanoate), 1.21 (3H, d, J=6.3 Hz, 1'-Me), 2.93 (2H, dd, J$_{1-4}$=9 Hz, J$_{gem}$=4 Hz, 1-Hs), 3.28 (1H, dd, J$_{6-1'}$→6.2 Hz, J$_{6-5}$=2.5 Hz, 6-H), 3.42 (2H, t, J=6 Hz, —CH$_2$S), 3.98 (1H, td, J$_{5-1}$=9 Hz, J$_{5-6}$=2.5 Hz, 5-H), 4.15 (1H, q, J=6.2 Hz, 1'-H), 4.80 (2H, t, J=6.0 Hz, —CH$_2$N+), 7–7.5 (m, phenyl protons from diphenyl phosphate), 8.03 (2H, m, Hm of pyridinium), 8.56 (1H, m, Hp of pyridinium) and 8.81 ppm (2H, "d", J≃6.5 Hz, Ho of pyridinium).

EXAMPLE 18

The compounds of Examples 4–17 may also be prepared by the procedure of Example 1 or 2 by reacting the appropriate intermediate of the formula

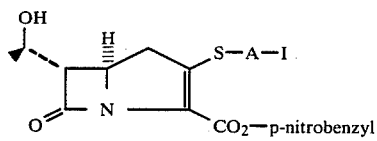

with the appropriate heteroaromatic nucleophile

and then removing the p-nitrobenzyl carboxyl-protecting group by catalytic hydrogenation.

We claim:
1. A compound of the formula

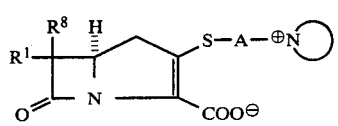

wherein $R^8$ is hydrogen and $R^1$ is hydrogen, $CH_3CH_2—$,

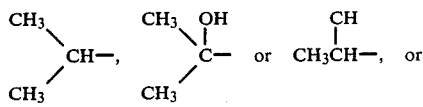

$R^1$ and $R^8$ taken together represent

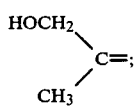

A is cyclopentylene, cyclohexylene or $C_2$–$C_6$ alkylene optionally substituted by one or more $C_1$–$C_4$ alkyl groups; and

represents a radical selected from

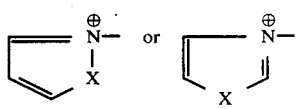 (a)

wherein X is O, S or NR in which R is $C_1$–$C_4$ alkyl or phenyl, said radical being optionally substituted on a carbon atom by one or more substituents independently selected from $C_1$–$C_4$ alkyl; $C_1$–$C_4$ alkyl substituted by hydroxy; amino, carboxy or halogen; $C_3$–$C_6$ cycloalkyl; $C_1$–$C_4$ alkoxy; $C_1$–$C_4$ alkylthio; amino; $C_1$–$C_4$ alkylamino; di($C_1$–$C_4$ alkyl)amino; halo; $C_1$–$C_4$ alkanoylamino; $C_1$–$C_4$ alkanoyloxy; carboxy;

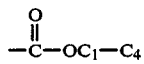

alkyl; hydroxy; amidino; guanidino, trifluoromethyl; phenyl; phenyl substituted by one, two or three amino, halo, hydroxyl, trifluoromethyl, $C_1$–$C_4$ alkyl or $C_1$–$C_4$ alkoxy groups; and heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms;

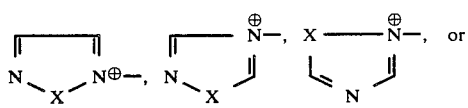 (b)

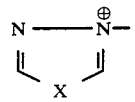

wherein X is O, S or NR in which R is $C_1$–$C_4$ alkyl or phenyl, said radical being optionally substituted on a carbon atom by one or more substituents independently selected from $C_1$–$C_4$ alkyl; $C_1$–$C_4$ alkyl substituted by hydroxy; amino, carboxy or halogen; $C_3$–$C_6$ cycloalkyl; $C_1$–$C_4$ alkoxy; $C_1$–$C_4$ alkylthio; amino; $C_1$–$C_4$ alkylamino; di($C_1$–$C_4$ alkyl)amino; halo; $C_1$–$C_4$ alkanoylamino; $C_1$–$C_4$ alkanoyloxy; carboxy;

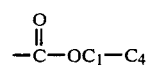

alkyl; hydroxy; amidino; guanidino, trifluoromethyl; phenyl; phenyl substituted by one, two or three amino, halo, hydroxyl, trifluoromethyl, $C_1$–$C_4$ alkyl or $C_1$–$C_4$ alkoxy groups; and heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms; and

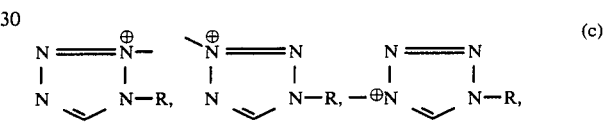 (c)

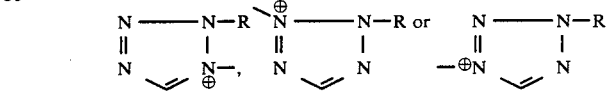

wherein R is $C_1$–$C_4$ alkyl or phenyl, said radical being optionally substituted on the carbon atom by a substituent selected from $C_1$–$C_4$ alkyl; $C_1$–$C_4$ alkyl substituted by hydroxy, amino, carboxy or halogen; $C_3$–$C_6$ cycloalkyl; $C_1$–$C_4$ alkylthio; amino; $C_1$–$C_4$ alkylamino; di($C_1$–$C_4$ alkyl)amino; halo; $C_1$–$C_4$ alkanoylamino; $C_1$–$C_4$ alkanoyloxy; carboxy;

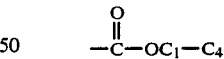

alkyl; hydroxy; amidino; guanidino; trifluoromethyl; phenyl; phenyl substituted by one, two or three amino, halo, hydroxyl, trifluoromethyl, $C_1$–$C_4$ alkyl or $C_1$–$C_4$ alkoxy groups; and heteroaryl or heteroaralkyl in which the hetero atom or atoms in the above-named heterocyclic moieties are selected from the group consisting of 1–4 oxygen, nitrogen or sulfur atoms and the alkyl moiety associated with said heteroaralkyl moiety has 1–6 carbon atoms, or a pharmaceutically acceptable salt or ester thereof.

2. A compound according to claim 1 wherein $R^1$ is

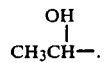

3. A compound according to claim 1 wherein $R^1$ is

and the absolute configuration is 5R, 6S, 8R.
4. A compound according to claim 1, 2 or 3 wherein A is —CH$_2$CH$_2$—, —CH$_2$CH$_2$CH$_2$—,
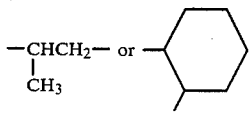
5. A compound of the formula
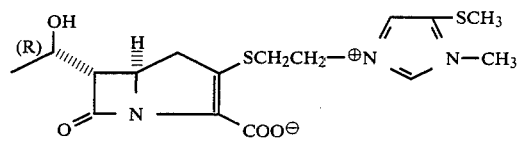
or a pharmaceutically acceptable salt or ester thereof.
* * * * *